United States Patent
Wrobel et al.

(12) 
(10) Patent No.: US 6,251,936 B1
(45) Date of Patent: Jun. 26, 2001

(54) BENZOTHIOPHENES, BENZOFURANS, AND INDOLES USEFUL IN THE TREATMENT OF INSULIN RESISTANCE AND HYPERGLYCEMIA

(75) Inventors: Jay E. Wrobel, Lawrenceville; Arlene J. Dietrich, Delran; Madelene M. Antane, Lawrenceville, all of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/307,687

(22) Filed: May 10, 1999

Related U.S. Application Data
(60) Provisional application No. 60/109,813, filed on May 12, 1998, now abandoned.

(51) Int. Cl.[7] .................. C07D 333/74; A61K 31/381
(52) U.S. Cl. .................. 514/443; 514/232.8; 514/468; 514/410; 544/146; 548/427; 549/43; 549/48; 549/458
(58) Field of Search .................. 548/427; 549/43, 549/48, 458; 544/146; 514/443, 410, 468, 232.8

(56) References Cited

U.S. PATENT DOCUMENTS

| | | |
|---|---|---|
| 3,558,655 | 1/1971 | Kaltenbronn . |
| 3,639,422 | 2/1972 | Blankley . |
| 3,682,976 | 8/1972 | Kaltenbronn et al. . |
| 4,808,599 | 2/1989 | Dubroeucq et al. . |
| 5,698,574 | 12/1997 | Riedl et al. . |
| 5,861,266 | 1/1999 | Ullrich et al. . |

FOREIGN PATENT DOCUMENTS

| | | |
|---|---|---|
| 0169012 | 1/1986 | (EP) . |
| 0316939 | 5/1989 | (EP) . |
| 0435322 | 7/1991 | (EP) . |
| 0568289 | 11/1993 | (EP) . |
| 4016854 | 1/1992 | (JP) . |

OTHER PUBLICATIONS

Demerseman , Bull. de la Soc.Chim. de France (1970), (6) 2253–61.*
Napolitano, A. et al., Tetrahedron, 45:21, 1989, pp. 6749–6760.
Schuster, I. I., et al., J. Org. Chem., 53, 1988, pp. 5819–5825.
d'Ischia, M. et al., Tetrahedron, 43:2, 1987, pp. 431–434.
Dryhurst, G. et al., J. Am. Chem. Soc., 111, 1989, pp. 719–726.
Guirguis, N. R. et al., J. Prakt. Chemie, 332:3, 1990, pp. 414–418.
Guirguis, N. R. et al., Liebigs Ann. Chem., 1986, pp. 1003–1011.
Han, B. H. et al., Tetrahedron Leter, 31:8, 1990, pp. 1181–1182.
Hashem, A. I., J. Prakt. Chemie, 319:4, 1977, pp. 689–692.
Ahmad, F. et al., Biochemica et Biophysica Acta, 1248, 1995, pp. 57–69.
Chang, A.Y. et al., Diabetes, 32, 1983, pp. 830–838.
Coleman, D. L., Diabetologia, 14, 1978, pp. 141–148.
DeFronzo, R. A. et al., Diabetes Care, 14:3, 1991, pp. 173–194.
Goldstein, B. J., Receptor 3, 1993, pp. 1–15.
Goldstein, B. J. et al., Mol. and Cell. Biochem., 109, 1992, pp. 107–113.
Goldstein, B. J., J. Cell. Biochem., 48, 1992, pp. 33–42.
Haring, H. U., Diabetologia, 34, 1991, pp. 848–861.

(List continued on next page.)

Primary Examiner—Robert Gerstl
(74) Attorney, Agent, or Firm—Arnold S. Milowsky

(57) ABSTRACT

This invention provides compounds of Formula I having the structure

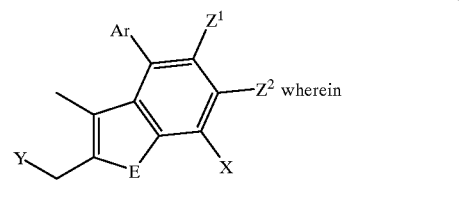

(I)

wherein

Ar is

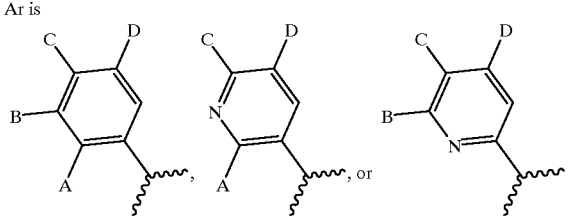

E is S, SO, $SO_2$, O, or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyaralkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, —$OCH_2CO_2R^{2b}$ or —$COR^{2c}$;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —CH=$CR^9$—$CR^{10}$=$CR^{11}$—;

or a pharmaceutically acceptable salt thereof, which are useful in treating metabolic disorders related to insulin resistance or hyperglycemia.

44 Claims, No Drawings

OTHER PUBLICATIONS

Harris, M. I., et al., Diabetes in America, 1985, Chapter 29, pp. 1–48.
Jarrett, R. J., Diabetes/Metabolism Reviews, 5:7, 1989, pp. 547–558.
Lanzetta, P. A. et al., Analytical Biochem. 100, 1979, pp. 95–97.
McGuire, M. C. et al., Diabetes, 40, Jul. 1991, pp. 939–942.
Meyerovitch, J. et al., J. Clin. Invest., 87, Apr. 1991, pp. 1286–1294.
Meyerovitch, J. et al., J. Clin. Invest. 84, Sep. 1989, pp. 976–983.
Mitsunobu, O., Synthesis, Jan. 1981, pp. 1–28.
Nutaitis, C. F., Organic Preparations and Procedures Int., 23(4), 1991, pp. 403–411.
Perich, J. W. et al., Synthesis, Feb. 1988, pp. 142–144.
Phillion, D.P. et al., Tetrahedron, 27:13, 1986, pp. 1477–1480.
Pyorala, K. et al., Diabetes/Metabolism Reviews, 3:2, 1987, pp. 463–524.
Reaven, G. M. et al., Amer. J. Med., 60, 1976, pp. 80–88.
Sredy, J. et al., Metabolism, 44:8, 1995, pp. 1074–1081.
Stout, R. W., Metabolism, 34:12 (Suppl 1), Dec. 1985, pp. 7–12.
Zask, A. et al., J. Med. Chem., 33, 1990, pp. 1418–1423.
Chen, H.–M. et al., Indian J. Chem., 35B, Dec. 1996, pp. 1304–1307.
Demerseman, Bull. de la Soc.Chim. de France (1970), (6) 2253–61, 1970.*
Katritzky, Tetrahedron Lett. 37 (32) 5641–4, 1970.*

* cited by examiner

BENZOTHIOPHENES, BENZOFURANS, AND INDOLES USEFUL IN THE TREATMENT OF INSULIN RESISTANCE AND HYPERGLYCEMIA

This application claims the benefit of U.S. Provisional Application No. 60/109,813, which was converted from U.S. patent application Ser. No. 09/076,712, filed May 12, 1998, pursuant to a petition filed under 37 C.F.R. 1.53(c)(2)(i) on Aug. 17, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, Receptor 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

B. Reidl, et al. (EP 693491A1) disclosed the oxazolodinone A as an antibacterial agent.

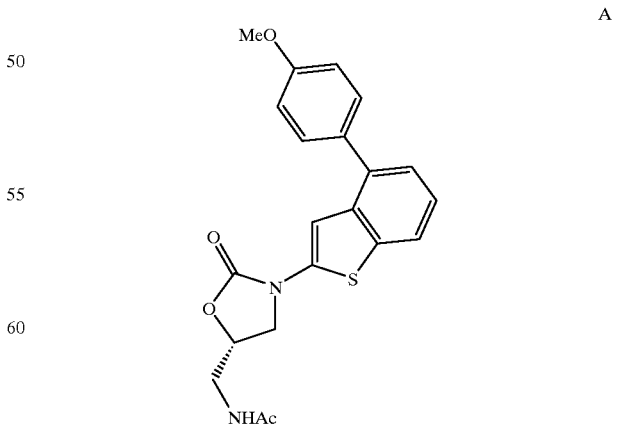

A. Bridges, et al. (EP 568289A2) disclosed the thienothiopheneamidine B as a urokinase inhibitor.

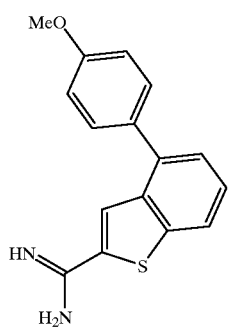

B

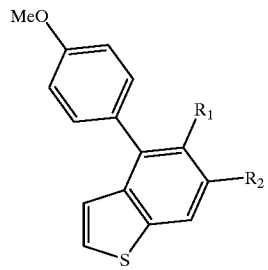

E

R1, R2 = CO2R3 or H
R3 = H, alkyl

H.-M. Chen, et al., *Indian J. Chem.,Sect. B: Org. Chem. Include. Med. Chem.* 1996, 35B(12), 1304–1307 disclosed compound C.

T. Kuroda, et al., *J. Org. Chem.* 1994, 59, 7353–7357 and *J. Chem. Soc., Chem. Commun.* 1991, 1635–1636 disclosed benzothiophenes F.

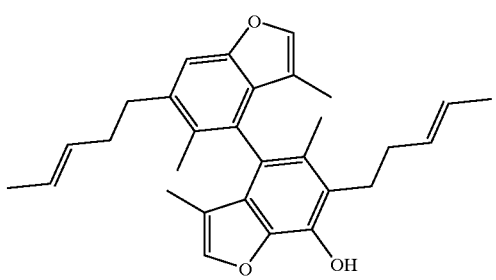

C

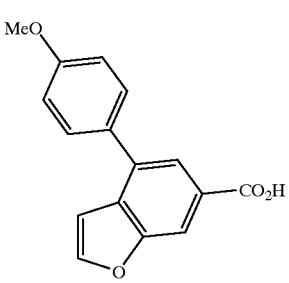

F

N. R. Guirguis, et al., *J. Prakt. Chem.* 1990, 332(3), 414–418 disclosed compound D.

A. I. Hashem, *J. Prakt. Chem.* 1977, 319, 689–692 disclosed benzofuran G.

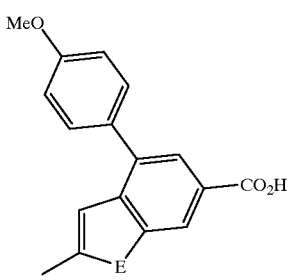

D

E = O, S

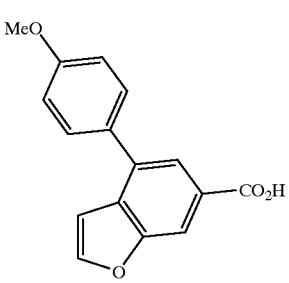

G

N. R. Guirguis, et al., *Liebigs Ann. Chem.* 1986, 1003–1011 disclosed benzothiophenes E. Also M. C. Dubroeucq et al., (EP 248734A1) dosclosed E (R1=CO$_2$H) as an anxiolytic.

Y. Akao, et al., Jpn. Kokai Tokkyo Koho JP 04016854 A2(Japanese patent, CA: 117:36570) disclosed six compounds containing the 4-aryl-naphtho[2,3-b]thiophene ring system. These compounds were cyclobutenediylium dimers of that ring system made as electrophotographic photoreceptors. One typical example is shown by structure H below.

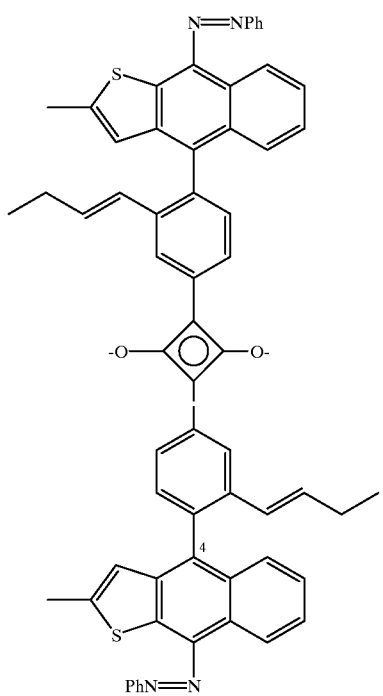

J. P. Konopelski, et al., *Synlett* 1996, 609–611 disclosed indole I.

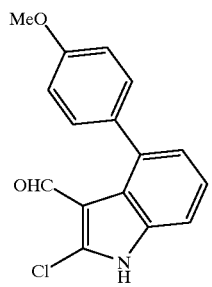

P. Molina, et al, *Tetrahedron,* 1994, 50, 5027–36 and *Tetrahedron Lett.,* 1993, 34, 2809–2812 disclosed indole derivatives J.

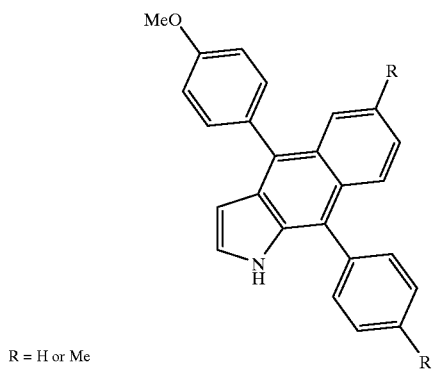

A. Napolitano, et al., *Tetrahedron* 1989, 45, 6749–60 disclosed indole K.

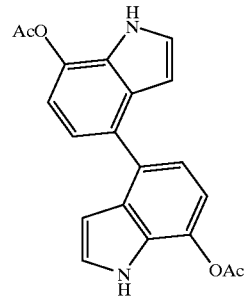

G. Dryhurst, et al., *J. Am. Chem. Soc.* 1989, 111, 719–726 disclosed compound L.

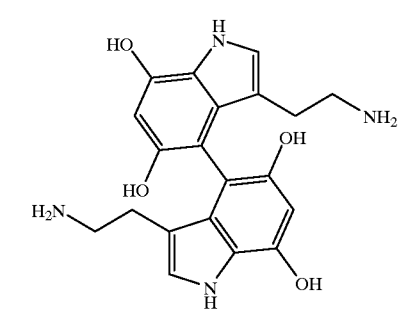

M. d'Ischia, et al., *Tetrahedron* 1987, 43, 431–434 disclosed compound M.

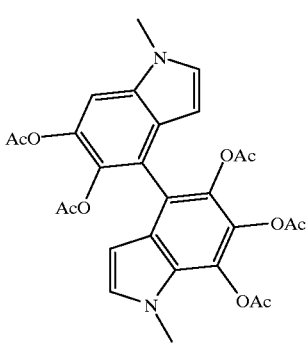

DESCRIPTION OF THE INVENTION

This invention provides a compound of formula I having the structure

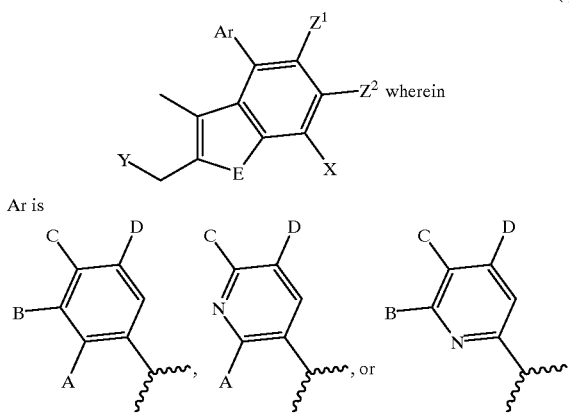

(I) wherein

Ar is

A is hydrogen, halogen, or OH;

B and D are each, independently, hydrogen, halogen, CN, alkyl of 1–6 carbon atoms, aryl, aralkyl of 6–12 carbon atoms, hydroxyalkyl of 1–6 carbon atoms, hydroxyaralkyl of 6–12 carbon atoms, cycloalkyl of 3–8 carbon atoms, nitro, amino, $-NR^1R^{1a}$, $-NR^1COR^{1a}$, $-NR^1CO_2R^{1a}$, cycloalkylamino of 3–8 carbon atoms, morpholino, furan-2-yl, furan-3-yl, thiophen-2-yl, thiophen-3-yl, $-COR^{1b}$ or OR;

R is hydrogen, alkyl of 1–6 carbon atoms, $-COR^1$, $-(CH_2)_nCO_2R^1$, $-CH(R^{1a})CO_2R^1$, $-SO_2R^1$, $-(CH_2)_mCH(OH)CO_2R^1$, $-(CH_2)_mCOCO_2R^1$, $-(CH_2)_mCH=CHCO_2R^1$, or $-(CH_2)_mO(CH_2)_oCO_2R^1$;

$R^1$ is hydrogen, alkyl of 1–6 carbon atoms, aralkyl of 6–12 carbon atoms, aryl, or $CH_2CO_2R^{1'}$;

$R^{1'}$ is hydrogen or alkyl of 1–6 carbon atoms

E is S, SO, $SO_2$, O, or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyaralkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, $-OCH_2CO_2R^{2b}$ or $-COR^{2c}$;

Y is hydrogen, halogen, alkyl of 1–6 carbon atoms, aryl, aralkyl of 6–12 carbon atoms, hydroxyalkyl of 1–6 carbon atoms, hydroxyaralkyl of 6–12 carbon atoms, $-OR^3$, $SR^3$, $NR^3R^{3a}$, $-COR^{3b}$, morpholine or piperidine;

$R^{1a}$, $R^{1c}$, $R^2$, $R^{2a}$ $R^3$, $R^{3a}$ are each, independently, hydrogen, alkyl of 1–6 carbon atoms, aralkyl of 6–12 carbon atoms, or aryl;

$R^{1b}$ is alkyl of 1–6 carbon atoms or aryl;

$R^{2b}$ is hydrogen, alkyl of 1–6 carbon atoms;

$R^{2c}$ and $R^{3b}$ are each, independently, alkyl of 1–6 carbon atoms, aryl, or aralkyl of 6–12 carbon atoms;

C is hydrogen, halogen or $OR^4$;

$R^4$ is hydrogen, alkyl of 1–6 carbon atoms, $-CH(R_5)W$, $-C(CH_3)_2CO_2R^6$, 5-thiazolidine-2,4-dione, $-CH(R^7)(CH_2)_mCO_2R^6$, $-COR^6$, $-PO_3(R^6)_2$, $-SO_2R^6$, $-(CH_2)_pCH(OH)CO_2R^6$, $-(CH_2)_pCOCO_2R^6$, $-(CH_2)_pCH=CHCO_2R^6$, or $-(CH_2)_pO(CH_2)_qCO_2R^6$;

$R^5$ is hydrogen, alkyl of 1–6 carbon atoms, aralkyl of 6–12 carbon atoms, aryl, $-CH_2(1H-imidazol-4-yl)$, $-CH_2(3-1H-indolyl)$, $-CH_2CH_2(1,3-dioxo-1,3-dihydro-isoindol-2-yl)$, $-CH_2CH_2(1-oxo-1,3-dihydro-isoindol-2-yl)$, $-CH_2(3-pyridyl)$, $-CH_2CO_2H$, or $-(CH_2)_nG$;

G is $NR^{6a}R^{7a}$, $NR^{6a}COR^{7a}$,

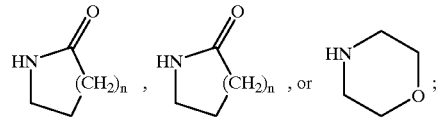

W is $CO_2R^6$, $CONH_2$, CONHOH, CN, $CONH(CH_2)_2CN$, 5-tetrazole, $-PO_3(R^6)_2$, $-CH_2OH$, $-CONR^{6b}CHR^{7b}$, $-CH_2NR^{6b}CHR^{7b}CO_2R^6$, $-CH_2OCHR^{7b}CO_2R^6$ $-CH_2Br$, or $-CONR^{6b}CHR^{7b}CO_2R^6$;

$R^6$, $R^{6a}$, $R^7$, $R^{7a}$ are each, independently, is hydrogen, alkyl of 1–6 carbon atoms, or aryl;

$R^{6b}$ is hydrogen or $-COR^{6c}$;

$R^{6c}$ is alkyl of 1–6 carbon atoms or aryl;

$R^{7b}$ is hydrogen, alkyl of 1–6 carbon atoms, or hydroxyalkyl of 1–6 carbon atoms;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, $-NR^1R^{1a}$, $-NR^1COR^{1a}$, cycloalkylamino of 3–8 carbon atoms, morpholino, or $OR^8$, or $Z^1$ and $Z^2$ may be taken together as a diene unit having the formula $-CH=CR^9-CR^{10}=CR^{11}-$;

$R^8$ is hydrogen, alkyl of 1–6 carbon atoms, or aryl;

$R^9$, $R^{10}$, and $R^{11}$ are each, independently, hydrogen, alkyl of 1–6 carbon atoms, aryl, halogen, hydroxy, or alkoxy of 1–6 carbon atoms m is 1 to 4 n is 1 or 2;

p is 1 to 4;

q is 1 to 4;

or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety, such as when $R^5$ is CH2(3-pyridyl), or Y is morpholine or contains similar basic moieties. Salts may also be formed from organic and inorganic bases, preferably alkali metal salts, for example, sodium, lithium, or potassium, when a compound of this invention contains a carboxylate or phenolic moiety.

Alkyl includes both straight chain as well as branched moieties. Halogen means bromine, chlorine, fluorine, and iodine. It is preferred that the aryl portion of the aryl or aralkyl substituent is a phenyl or naphthyl; with phenyl being most preferred. The aryl moiety may be optionally mono-, di-, or tri- substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The compounds of this invention may be atropisomers by virtue of possible restricted or slow rotation about the aryl-tricyclic or aryl-bicyle single bond. This restricted rotation creates additional chirality and leads to enantiomeric forms. If there is an additional chiral center in the molecule, diasteriomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixutures of diasteomers) and pharmaceutically acceptable salts thereof.

Preferred compounds of this invention include compounds of formula (I), having the structure

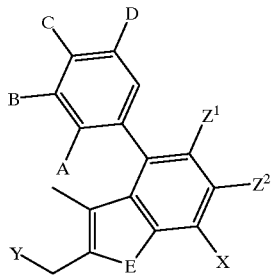

(I)

wherein
A is hydrogen or halogen
B and D are each, independently, hydrogen, halogen, CN, alkyl of 1–6 carbon atoms, aryl, aralkyl of 6–12 carbon atoms, branched alkyl, cycloalkyl of 3–8 carbon atoms, nitro or OR;
R is hydrogen or alkyl of 1–6 carbon atoms;
E is S, or O;
X is hydrogen, halogen, alkyl of 1–6 carbon atoms, CN, perfluoroalkyl of 1–6 carbon atoms, alkoxy of 1–6 carbon atoms, aryloxy; arylalkoxy, nitro, amino, NR$^2$R$^{2a}$, NR$^2$COR$^{2a}$, cycloalkylamino, morpholino, alkylsulfanyl of 1–6 carbon atoms, arylsulfanyl, pyridylsulfanyl, 2-N,N-dimethylaminoethylsulfanyl;
R$^1$, R$^{1a}$, R$^2$, R$^{2a}$, R$^3$, and R$^{3a}$ are each, independently, hydrogen, alkyl of 1–6 carbon atoms, aralkyl of 6–12 carbon atoms, or aryl;
Y is hydrogen, halogen, OR$^3$, SR$^3$, NR$^3$R$^{3a}$ or morpholine;
C is hydrogen, halogen, or OR$^4$;
R$^4$ is hydrogen, alkyl of 1–6 carbon atoms, —CH(R$^5$)W, —C(CH$_3$)$_2$CO$_2$R$^6$, 5-thiazolidine-2,4dione, —CH(R$^7$)(CH$_2$)$_m$CO$_2$R$^6$, —COR$^6$, —PO$_3$(R$^6$)$_2$, —SO$_2$R$^6$, —(CH$_2$)$_p$CH(OH)CO$_2$R$^6$, —(CH$_2$)$_p$COCO$_2$R$^6$, —(CH$_2$)$_p$CH=CHCO$_2$R$^6$, or —(CH$_2$)$_p$O(CH$_2$)$_q$CO$_2$R$^6$;
R$^5$ is hydrogen, alkyl of 1–6 carbon atoms, aralkyl of 6–12 carbon atoms, aryl, —CH$_2$(1H-imidazol-4-yl), —CH$_2$(3-1H-indolyl), —CH$_2$CH$_2$(1,3-dioxo-1,3-dihydro-isoindol-2-yl), —CH$_2$CH$_2$(1-oxo-1,3-dihydro-isoindol-2-yl), or —CH$_2$(3-pyridyl);
W is CO$_2$R$^6$, —CONH$_2$, —CONHOH, or 5-tetrazole, or —CONR$^{6b}$CHR$^{7b}$CO$_2$R$^6$;
R$^6$, R$^{6a}$, R$^{6b}$, R$^7$, R$^{7a}$, and R$^{7b}$ are each, independently, hydrogen, alkyl of 1–6 carbon atoms, or aryl;
Z$^1$ and Z$^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —NR$^1$R$^{1a}$, —NR$^1$COR$^{1a}$, cycloalkylamino of 3–8 carbon atoms, morpholino, or OR$^8$, or Z$^1$ and Z$^2$ may be taken together as a diene unit having the formula —CH=CR$^9$—CR$^{10}$=CH—;
R$^9$ and R$^{10}$ are independently, hydrogen, or alkyl of 1–6 carbon atoms;
p is 1 to 4;
q is 1 to 4;
or a pharmaceutically acceptable salt thereof.

More preferred compounds of this invention include compounds of formula (I), having the structure

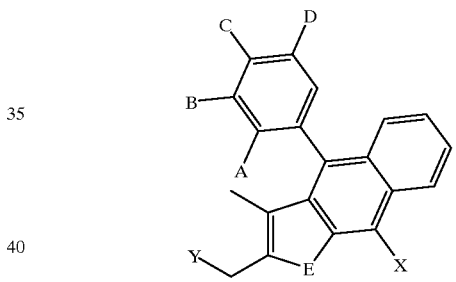

(I)

wherein
A is hydrogen;
B and D are each, independently, halogen, alkyl of 1–6 carbon atoms, aryl, aralkyl of 6–12 carbon atoms, or cycloalkyl of 3–8 carbon atoms;
E is S or O;
X is hydrogen, halogen, alkyl of 1–6 carbon atoms, perfluoroalkyl of 1–6 carbon atoms, CN, alkoxy of 1–6 carbon atoms, aryloxy, arylalkoxy of 6–12 carbon atoms, arylsulfanyl;
Y is hydrogen or —NR$^1$R$^2$, or morpholine;
R$^1$ and R$^2$ are each, independently, hydrogen or alkyl of 1–6 carbon atoms, aralkyl of 6–12 carbon atoms, or aryl;
C is OR$^4$;
R$^4$ is hydrogen, alkyl of 1–6 carbon atoms, —CH(R$^5$)W, or 5-thiazolidine-2,4-dione;
R$^5$ is hydrogen, alkyl of 1–6 carbon atoms, aralkyl of 6–12 carbon atoms, aryl, —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl);
W is —CO$_2$R$^6$, —CONH$_2$, —CONHOH, 5-tetrazole, —PO$_3$(R$^6$)$_2$, or —CONR$^6$CHR$^6$CO$_2$R$^6$ R⁶ is hydrogen or alkyl of 1–6 carbon atoms;

Z¹ and Z² are taken together as a diene unit having the formula —CH=CH—H=CH—;

or a pharmaceutically acceptable salt thereof.

Even more preferred compounds of this invention include:

(R)-2-[2,6-dibromo-4-(9-bromo-2,3-dimethyl-naphtho[2,3-b]thiophen-4-yl)-phenoxy]-3-phenyl-propionic acid;

(R)-2-[2-bromo-4-(9-bromo-2,3-dimethyl-naphtho[2,3-b]thiophen-4-yl)-6-ethyl-phenoxy]-3-phenyl-propionic acid;

(R)-2-[4-(9-bromo-2,3-dimethyl-naphtho[2,3-b]thiophen-4-yl)-2,6-dimethyl-phenoxy]-3-phenyl-propionic acid;

(R)-2-[4-(9-bromo-2,3-dimethyl-naphtho[2,3-b]thiophen-4-yl)-2-fluoro-phenoxy]-3-phenyl-propionic acid;

[4-(9-bromo-2,3-dimethyl-naphtho[2,3-b]thiophen-4-yl)-2,6-diisopropyl-phenoxy]-acetic acid;

(R)-2-[2-bromo-4-(9-bromo-2,3-dimethyl-naphtho[2,3-b]thiophen-4-yl)-6-sec-butyl-phenoxy]-3-phenyl-propionic acid;

(R)-2-[2-bromo-4-(9-bromo-2,3-dimethyl-naphtho[2,3-b]thiophen-4-yl)-6-isopropyl-phenoxy]-3-phenyl-propionic acid;

(R)-2-[2-bromo-4-(9-bromo-2,3-dimethyl-naphtho[2,3-b]thiophen-4-yl)-2-cyclopentyl-phenoxy]-3-phenyl-propionic acid (R)-2-[4-(9-bromo-2,3-dimethyl-naphtho[2,3-b]thiophen-4-yl)-6-isopropyl-phenoxy]-3-phenyl-propionic acid;

(R)-2-[4-(9-bromo-2,3-dimethyl-naphtho[2,3-b]thiophen-4-yl)-2-cyclopentyl-phenoxy]-3-phenyl-propionic acid;

(R)-2-[2,6-dibromo-4-(2,3-dimethyl-9-phenylsulfanyl-naphtho[2,3-b]thiophen-4-yl)-phenoxy]-3-phenyl-propionic acid;

(R)-2-[2,6-dibromo-4-(9-bromo-2,3-dimethyl-naphtho[2,3-b]thiophen-4-yl)-phenoxy]-4-phenyl-butyric acid;

(S)-2-[2,6-dibromo-4-(9-bromo-2,3-dimethyl-naphtho[2,3-b]thiophen-4-yl)-phenoxy]-4-phenyl-butyric acid;

2-[2,6-dibromo-4-(9-bromo-3-methyl-2-morpholin-4-ylmethyl-naphtho[2,3-b]thiophen-4-yl)-phenoxy]-3-phenyl-propionic acid;

(R)-2-[2,6-dibromo-4-(2,3-dimethyl-9-phenylsulfanyl-naphtho[2,3-b]thiophen-4-yl)-phenoxy]-propionic acid;

[2-bromo-4-(9-bromo-2,3-dimethyl-naphtho[2,3-b]thiophen-4-yl)-2-nitro-phenoxy]-3-phenyl-propionic acid;

2,6-dibromo-4-(9-bromo-2,3-dimethyl-naphtho[2,3-b]thiophen-4-yl)-phenol;

2-bromo-4-(9-bromo-2,3-dimethyl-naphtho[2,3-b]thiophen-4-yl)-2-nitro-phenol;

(R)-2-[2,6-dibromo-4-(9-bromo-2-diethylaminomethyl-3-methyl-naphtho[2,3-b]thiophen-4-yl)-phenoxy]-3-phenyl-propionic acid;

(R)-2-[2,6-dibromo-4-(2,3-dimethyl-naphtho[2,3-b]furan-4-yl)-phenoxy]-3-phenyl-propionic acid, (2R)-2-[4-(9-bromo-2,3-dimethyl-naphtho[2,3-b]thiophen-4-yl)-2,6-diisopropyl-phenoxy]-3-phenyl-propionic acid, (R)-2-[4-(9-bromo-2,3-dimethyl-naphtho[2,3-b]thiophen-4-yl)-2,6-diethyl-phenoxy]-3-phenyl-propionic acid, {(2R)-2-[4-(9-bromo-2,3-dimethyl-naphtho[2,3-b]thiophen-4-yl)-2,6-dimethyl-phenoxy]-3-phenyl-propionylamino}-acetic acid;

{(2R)-2-[4-(9-bromo-2,3-dimethyl-naphtho[2,3-b]thiophen-4-yl)-2,6-diethyl-phenoxy]-3-phenyl-propionylamino}-acetic acid or pharmaceutically acceptable salts thereof.

The compounds of this invention can be prepared according to the following schemes from commercially available starting materials or starting materials which can be prepared using to literature procedures. These schemes show the preparation of representative compounds of this invention.

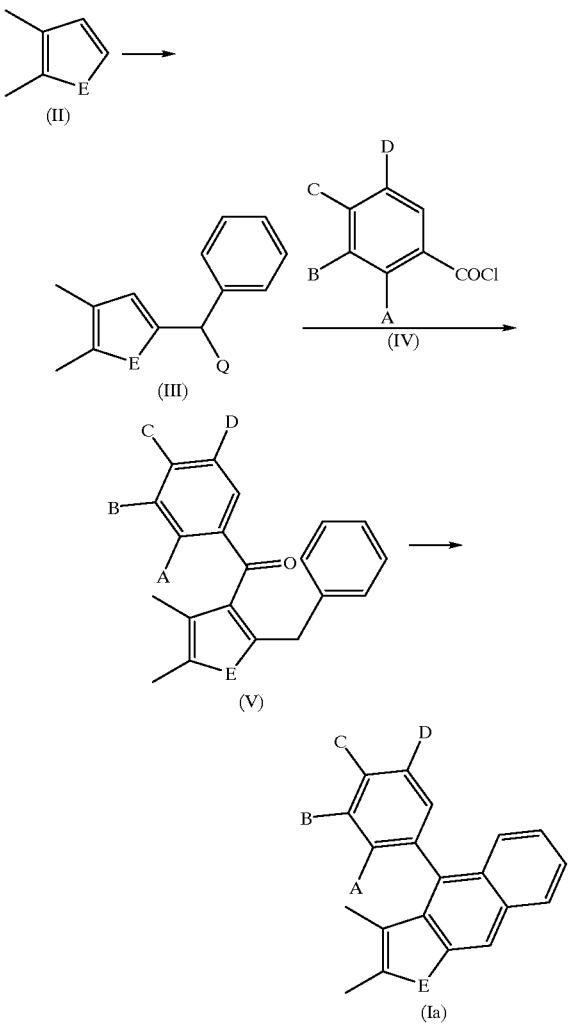

In Scheme 1,2,3-dimethylthiophene (II: E is S) is prepared from commercially available 3-methyl-thiophene-carboxaldehyde using Wolff-Kishner conditions (hydrazine followed by KOH/ethylene glycol reflux). Compound (II: E is S or O) is treated with one to 1.3 molar equivalents of an alkyl lithium reagent such as N-butyl lithium most preferably in a nonprotic solvent such as THF at temperatures ranging from −78° C. to room temperature under an inert atmosphere such as nitrogen or argon to provide the 2-lithiated-thiophene or furan derivative. This lithiated analog is reacted in situ with one or more molar equivalents of benzaldehyde, generally at −78° C. to room temperature for 5 min to 3 h to provide the compound of formula (III: Q=OH; E is S or O). The hydroxy group (Q=OH) of (III) can be removed by a number of reduction procedures such as hydrogenation using palladium catalysts to produce the compound of formula (III: Q=H; E is S or O) but is most conveniently removed using the method of Nutaitis, et. al. (*Org. Prep. and Proceed. Int.* 1991, 23, 403–411) in which (III: Q=OH; E is S or O) is stirred with one to ten molar equivalents of sodium borohydride in a suitable solvent such as ether, THF or dichloromethane at 0° C. to room temperature and one to fifty molar equivalents of trifluoroacetic acid is slowly added over a 15 min to 3 h period to produce the compound of formula (III: Q=H; E is S or O). Alternatively, the 2-lithiated analog of compound (II: E is S or O) in a nonprotic solvent such as THF can be reacted with one or more molar equivalents of a benzyl halide such as benzyl bromide (PhCH₂Br) at −78° C. to room temperature to directly provide the compound of formula (III: Q=H; E is S or O).

The compounds of formula (III: Q=H; E is S or O) can be acylated with one or more molar equivalents of a commercially available benzoic acid chloride of formula (IV: A, B, C, D is H or OMe; with the A, B, C, D, combination of substituents having at least one OMe group but not more than three OMe groups) to produce the acylated derivative of formula (V: A, B, C, D is H or OMe; with the A, B, C, D, combination of substituents having at least one OMe group but not more than three OMe groups; E is S or O). This acylation is accomplished most readily using a one to five molar equivalents of a Lewis acid catalyst such as tin tetrachloride or aluminum chloride in an inert solvent such as dichloromethane, 1,2-dichloroethane or carbon disulfide, generally at temperatures such as −78° C. to room temperature.

Cyclization of the compounds of formula (V: A, B, C, D is H or OMe; with the A, B, C, D, combination of substituents having at least one OMe group but not more than three OMe groups; E is S or O) is generally best accomplished using one to ten molar equivalents of a strong Lewis acid such as a trihaloborane, most conveniently tribromoborane. The reaction is best performed at −78° C. with warming to room temperature or heating to 50° C. in a halocarbon solvent such as dichloromethane under an inert atmosphere such as nitrogen or argon. These procedures not only effect cyclization and aromatization with concomitant loss of water, but also result in demethylation of any pendant methoxy moieties and result in the production of compounds of formula (Ia: A, B, C, D is H or OH; with the A, B, C, D, combination of substituents having at least one OH group but not more than three OH groups; E is S or O).

In an analogous fashion to the reactions above in Scheme 1, the compounds of formula (Ia: A is H; B, D is alkyl of 1–6 carbon atoms or fluoro; C is OH; E is S or O) can be prepared starting from the compound of formula (III: Q is H; E is S or O) and the appropriate benzoic acid chloride (IV: A is H; B, D is alkyl of 1–6 carbon atoms or fluoro; C is OMe). The benzoic acid chloride (IV: A is H; B, D is alkyl of 1–6 carbon atoms or fluoro; C is OMe). is prepared from the corresponding benzoic acid by standard procedures using reagents such as oxalyl chloride and thionyl chloride. The starting benzoic acid of the benzoic acid chloride (IV: A is H; B, D is alkyl of 1–6 carbon atoms or fluoro; C is OMe) is commercially available or can be easily prepared by known procedures. For example, the acid starting material for benzoic acid chloride (IV: A is H; B, D is isopropyl; C is OMe) can be prepared using a modification of the method of Schuster, et al., *J. Org. Chem.* 1988, 53, 5819. Thus commercially available 2,6-diisopropyl phenol is brominated in the 4-position (bromine/acetic acid), methylated (iodomethane/potassium carbonate/DMF), reacted with n-butyl lithium to effect lithium halogen exchange and the resultant organolithium species is reacted with carbon dioxide to provide 3,5-diisopropyl, 4-methoxy benzoic acid.

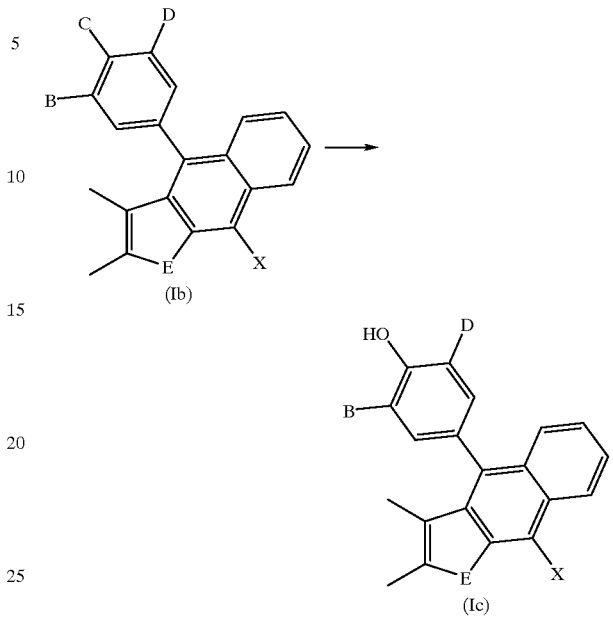

Scheme 2

Further derivatives of the compounds of formula (I) in Scheme 2 can be prepared by the following methods. The phenol of formula (Ib: B, D, X is H; C is OH; E is S or O) (Scheme 2) can be conveniently iodinated to the diiodophenol of formula (Ib: B, D is I; X is H; C is OH; E is S or O) using at least two molar equivalents of iodine in the presence of two or more molar equivalents of an alkali metal hydroxide such as NaOH in a alcohol solvent such as methanol at −20° C. to room temperature. Similarly the monoiodophenol (Ib: B is I; X, D is H; C is OH; E is S or O) can be prepared from the phenol of formula (Ib: B, D, X is H; C is OH; E is S or O) (Scheme 2) using one to 1.5 molar equivalents of iodine in the presence of at least one equivalent of an alkali metal hydroxide such as NaOH in a alcohol solvent such as methanol at −20° C. to room temperature. Either the monoiodophenol (Ib: B is I; X, D is H; C is OH; E is S or O) or the diiodophenol (Ib: B, D is I; X is H; C is OH; E is S or O) can be converted to the respective methyl ether derivatives of formula (Ib: B is I; X, D is H; C is OMe; E is S or O) or (Ib: B, D is I; X is H; C is OMe; E is S or O) by reacting the phenol moiety with a suitable methylating agent such as one or more molar equivalents of methyl iodide or dimethylsulfate employing a base such an alkali methyl carbonate or hydroxide such as potassium carbonate or sodium hydroxide in a suitable solvent such as THF, DMF or DMSO. The reaction is generally performed at temperatures ranging from 0° C. to 60° C.

The monoiodo methylether derivative of formula (Ib: B is I; X, D is H; C is OMe; E is S or O) or the diiodo methylether of formula (Ib: B, D is I; X is H; C is OMe; E is S or O) can be reacted with one or more molar equivalents of copper (I) cyanide for the monoiodo analog or two or more molar equivalents of copper (I) cyanide for the diiodo derivative to produce the monocyanomethyl ether of formula (Ib: B is CN; X, D is H; C is OMe; E is S or O) or the dicyanomethyl ether of formula (Ib: B, D is CN; X is H; C is OMe; E is S or O). The cyanation reaction is generally performed at temperatures ranging from 100° C. to 250° C. employing polar aprotic solvents such as DMF, 1-methyl-2-pyrrolidinone or HMPA. Quinoline or pyridine can also be used. The mono or dicyano methoxy analogs of formula (Ib: B is CN; D is H or CN; X is H; C is OMe; E is S or O); can be converted to the corresponding mono or dicyano phenol analogs of formula (Ic: B is CN; D is H or CN; X is H; E is S or O) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

The monoiodo methylether derivative of formula (Ib: B is I; X, D is H; C is OMe; E is S or O) or the diiodo methylether of formula (Ib: B, D is I; X is H; C is OMe; E is S or O) (Scheme 2) can be reacted with one or more molar equivalents of copper (I) bromide for the monoiodo analog or two or more molar equivalents of copper (I) bromide for the diiodo derivative to produce the monobromo methyl ether of formula (Ib: B is Br; X, D is H; C is OMe; E is S or O) or the dibromo-methyl ether of formula (Ib: B, D is Br; X is H; C is OMe; E is S or O). The bromine/iodine exchange reaction is generally performed at temperatures ranging from 100° C. to 250° C. employing polar aprotic solvents such as DMF, 1-methyl-2-pyrrolidinone or HMPA. Quinoline or pyridine can also be used. The mono or dibromo methoxy analogs of formula (Ib: B is Br; D is H or Br X is H; C is OMe; E is S or O) can be converted to the corresponding mono or dibromo phenol analogs of formula (Ic: B is Br; D is H or Br; X is H; E is S or O) (Scheme 2) using standard demethylation procedures including one or more molar equivalents of boron tribromide or boron trichloride in dichloromethane at −78° C. to room temperature; excess neat pyridinium hydrochloride at 190 to 280° C.; hydrobromic acid in acetic acid at 0° C. to 50° C.; excess trimethylsilylbromide or trimethylsilyliodide in dichloromethane, carbon tetrachloride or acetonitrile at −78° C. to 50° C.; lithium iodide in pyridine or quinoline at temperatures from 100° to 250° C. and one or more molar equivalents of ethyl, methyl or isopropyl mercaptan in the presence of one or more molar equivalents of a Lewis acid such as aluminum trichloride or boron trifluoride in a solvent such as dichloromethane at temperatures ranging from −78° C. to 50° C.

Scheme 3

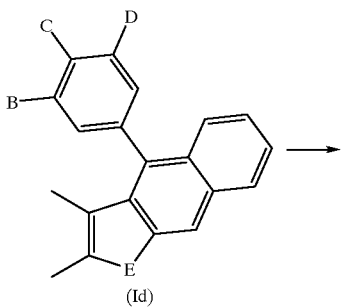

(Id)

-continued

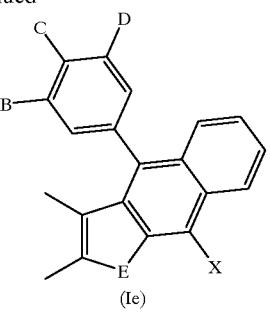

(Ie)

Further derivatives of the compounds of formula (I) in Scheme 3 can be prepared by the following methods. The compounds of formula (Id: B, C, D is H or OH; with the B, C, D combination having at least one OH group; E is S or O) (Scheme 3) can be acylated on the phenolic oxygen using one or more molar equivalents of suitable acylating agent to provide the compounds of formula (Id: B, C, D is H or OCOR; with the B, C, D combination having at least one OCOR group; R is alkyl of 1–6 carbon atoms, aryl; E is S or O). The acylating agent is generally alkyl of 1–6 carbon atoms or aryl carboxylic acid anhydride or alkyl of 1–6 carbon atoms or aryl carboxylic acid chloride. The reaction is run under standard conditions, for example the use of pyridine as solvent with or without a co-solvent such as dichloromethane at 0° C. to room temperature. The acylated phenols of formula (Id: B, C, D is H or OCOR; with the B, C, D combination having at least one OCOR group; R is alkyl of 1–6 carbon atoms, aryl; E is S or O) can then be brominated in the 9-position of the naphtho[2,3-b]thiophene or the naphtho[2,3-b]furan ring to form the acylated bromophenols of formula (Ie: B, C, D is H or OCOR; with the B, C, D combination having at least one OCOR group; R is alkyl of 1–6 carbon atoms, aryl; X is Br; E is S or O) (Scheme 3). This bromination reaction is generally done using 1 to 1.3 molar equivalents of molecular bromine in the dark with a catalytic amount of iron (III) chloride in an inert solvent such as dichloromethane or carbon tetrachloride at temperatures ranging from −78° C. to room temperature.

Using a similar bromination reaction, the phenols of formula (Id: B, D is alkyl of 1–6 carbon atoms, C is OH; E is S or O) can then be brominated in the 9-position of the naphtho[2,3-b]thiophene hene or the naphtho[2,3-b]furan ring to form the bromophenols of formula (Ie: B, D is alkyl of 1–6 carbon atoms, C is OH; X is Br; E is S or O) (Scheme 3). This bromination reaction is generally done using 1 to 1.3 molar equivalents of molecular bromine in the dark with a catalytic amount of iron (III) chloride in an inert solvent such as dichloromethane or carbon tetrachloride at temperatures ranging from −78° C. to room temperature.

The acyl group can then be removed from the acylated bromophenols of formula (Ie: B, C, D is H or OCOR; with the B, C, D combination having at least one OCOR group; R is alkyl of 1–6 carbon atoms, aryl; X is Br; E is S or O) to provide the bromophenols of formula (Ie: B, C, D is H or OH; with the B, C, D combination having at least one OH group; X is Br; E is S or O) (Scheme 3) using standard conditions. These conditions include aqueous base in which one or more molar equivalents of alkali metal hydroxide such as sodium hydroxide is used in water with a co-solvent such as THF, dioxane or a 1–6 carbon alcohol such as methanol or mixtures of THF and a 1–6 carbon atom alcohol at temperatures ranging from 0° C. to 40° C. Acid conditions may also be employed in which the compound is reacted with one or more molar equivalents of a mineral acid such as HCl or sulfuric acid in water with or without a co-solvent such as THF at temperatures ranging from room temperature to 80° C.

The acylated phenols of formula (Id: B, C, D is H or OCOR; with the B, C, D combination having at least one OCOR group; R is alkyl of 1–6 carbon atoms, aryl; E is S or O) can be nitrated to provide the nitro compounds of formula (Ie: B, C, D is H or OCOR; with the B, C, D combination having at least one OCOR group; R is alkyl of 1–6 carbon atoms, aryl; X is $NO_2$; E is S or O) (Scheme 3). Dilute nitric acid at temperatures ranging from 0° C. to room temperature is suitable to effect this transformation. The nitro compounds of formula (Ie: B, C, D is H or OCOR; C, D cannot both be H; R is alkyl fo 1–6 carbon atoms, aryl; X is $NO_2$; E is S or O) can be further reduced to the primary amine of formula (Ie: B, C, D is H or OCOR; with the B, C, D combination having at least one OCOR group; R is alkyl fo 1–6 carbon atoms, aryl; X is $NH_2$; E is S or O) using a suitable reducing agent such as catalytic hydrogenation with a palladium or platinum catalyst, tin dichloride in aqueous HCl or in ethyl acetate. The acyl group of the compounds of formula (Ie: B, C, D is H or OCOR; with the B, C, D combination having at least one OCOR group; R is alkyl of 1–6 carbon atoms, aryl; X is $NO_2$ or $NH_2$; E is S or O) can be removed using standard conditions.

The acylated bromophenols of formula (Ie: B, C, D is H or OCOR; with the B, C, D combination having at least one OCOR group; R is alkyl of 1–6 carbon atoms, aryl; X is Br; E is S or O) (Scheme 3) can be converted to the acylated cyanophenols of formula (Ie: B, C, D is H or OCOR; with the B, C, D combination having at least one OCOR group; R is alkyl of 1–6 carbon atoms, aryl; X is CN; E is S or O) by reaction with one or more molar equivalents of copper (I) cyanide. The cyanation reaction is generally performed at temperatures ranging from 100° C. to 250° C. employing polar aprotic solvents such as DMF, 1-methyl-2-pyrrolidinone or HMPA. Quinoline or pyridine can also be used. Often the acyl group of (Ie: B, C, D is H or OCOR; with the B, C, D combination having at least one OCOR group; R is alkyl of 1–6 carbon atoms, aryl; X is CN; E is S or O) is liberated under the cyanation reaction conditions to afford the cyanophenols of formula (Ie: B, C, D is H or OH; with the B, C, D combination having at least one OH group; X is CN; E is S or O). This liberation of the acyl group to afford the cyanophenols of formula (Ie: B, C, D is H or OH; with the B, C, D combination having at least one OH group; X is CN; E is S or O) can be effected most readily by addition of one or more molar equivalents of alkali metal hydroxide in water to the reaction mixture containing (Ie: B, C, D is H or OCOR; with the B, C, D combination having at least one OCOR group; R is alkyl of 1–6 carbon atoms, aryl; X is CN; E is S or O) prior to workup. The acyl group can also be removed from the isolated acylated cyanophenols of formula (Ie: B, C, D is H or OCOR; with the B, C, D combination having at least one OCOR group; R is alkyl of 1–6 carbon atoms, aryl; X is CN; E is S or O) to provide the cyanophenols of formula (Ie: B, C, D is H or OH; with the B, C, D combination having at least one OH group; R is alkyl of 1–6 carbon atoms, aryl; X is CN; E is S or O) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acid conditions may also be employed in which the compound is reacted with one or more molar equivalents of a mineral acid such as HCl or sulfuric acid in water with or without a co-solvent such as THF at temperatures ranging from room temperature to 80° C.

The compounds of formula (Id: B, C, D is H or OH; with the B, C, D combination having at least one OH group; E is S or O) (Scheme 3) can be sulfonylated on the phenolic oxygen using one or more molar equivalents of suitable sulfonylating agent to provide the sulfonic acid esters of formula (Id: B, C, D is H or $OSO_2R$; with the B, C, D combination having at least one $OSO_2R$ group; R is alkyl of 1–6 carbon atoms, aryl; E is S or O). The sulfonylating agent is generally a alkyl of 1–6 carbon atoms or aryl sulfonic acid anhydride or a alkyl of 1–6 carbon atoms or aryl sulfonic acid chloride. The reaction is run under standard conditions such as using pyridine as solvent with or without a co-solvent such as dichloromethane at 0° C. to room temperature.

The sulfonic acid esters of formula (Id: B, C, D is H or $OSO_2R$; with the B, C, D combination having at least one $OSO_2R$ group; R is alkyl of 1–6 carbon atoms, aryl; E is S or O) can be treated with iodinating reagents to effect iodination at the 9-position of the naphtho[2,3-d]thiophene or the naphtho[2,3-d]furan ring to afford the iodo sulfonic acid esters of formula (Ie: B, C, D is H or $OSO_2R$; with the B, C, D combination having at least one $OSO_2R$ group; R is alkyl of 1–6 carbon atoms, aryl; X is I; E is S or O). A suitable iodinating reagent includes a mixture of 0.7 or more molar equivalents of molecular iodine and 0.25 or more molar equivalents of iodic acid in a mixture of THF and 80% aqueous acetic acid with a small amount of concentrated sulfuric acid at temperatures ranging from room temperature to 80° C. The sulfonic ester group can then be removed from the iodo-sulfonic acid esters of formula (Ie: B, C, D is H or $OSO_2R$; with the B, C, D combination having at least one $OSO_2R$ group; R is alkyl of 1–6 carbon atoms, aryl; X is I; E is S or O) to provide the iodophenols of formula (Ie: B, C, D is H or OH; with the B, C, D combination having at least one OH group; X is I; E is S or O) (Scheme 3) using standard conditions. These conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from room temperature to 110° C.

Scheme 4

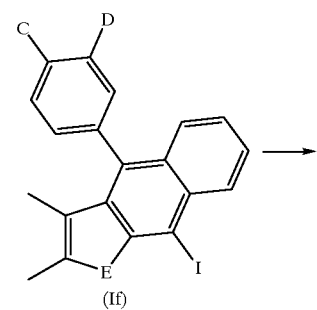

(If)

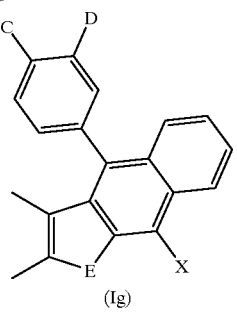

(Ig)

The iodo sulfonic acid esters of formula (If: C, D is H or OSO$_2$R; C, D cannot both be H; R is alkyl of 1–6 carbon atoms, aryl); E is S or O are a convenient starting point for further derivatives of the compounds of formula (I) as shown in Scheme 4 and the methods below. The compounds (If: C, D is H or OSO$_2$R; C, D cannot both be H; R is alkyl of 1–6 carbon atoms, aryl; E is S or O) can be reacted with a reagent that catalyzes the exchange of the iodine atom in (If) with a lower perfluoroalkyl group to afford the compound of formula (Ig: C, D is H or OSO$_2$R; C, D cannot both be H; R is alkyl of 1–6 carbon atoms, aryl; X is lower perfluoroalkyl; E is S or O) (Scheme 4). The reagent and conditions to effect this exchange include reacting (If) under anhydrous conditions with one to ten molar equivalents of a sodium perfluorocarboxylate (RCO$_2$Na: R is perfluoroalkyl) and one to five molar equivalents of copper (I) iodide in a high boiling inert solvent such as DMF, DMA or 1-methyl-2-pyrrolidinone at temperatures ranging from 140° C. to 200° C. Alternatively, the compound of formula (Ig: C, D is H or OSO$_2$R; C, D cannot both be H; R is alkyl of 1–6 carbon atoms, aryl; X is lower perfluoroalkyl; E is S or O) can be prepared from the compound of formula (If: C, D is H or OSO$_2$R; C, D cannot both be H; R is alkyl of 1–6 carbon atoms, aryl; E is S or O) by reacting the former with one to ten molar molar equivalents of a perfluoroalkyl iodide and one to five molar molar equivalents of activated Cu$^0$ in a high boiling inert solvent such as DMF, DMA or 1-methyl-2-pyrrolidinone at temperatures ranging from 140° C. to 200° C. Still, alternatively, the compound of formula (If: C, D is H or OSO$_2$R; C, D cannot both be H; R is alkyl of 1–6 carbon atoms, aryl; E is S or O) can be reacted with 0.5 to two molar equivalents of bis(trifluoromethyl)mercury and two to four molar equivalents of activated Cu$^0$ in a high boiling inert solvent such as DMF, DMA or 1-methyl-2-pyrrolidinone at temperatures ranging from 140° C. to 200° C. to produce the compound of (Ig: C, D is H or OSO$_2$R; C, D cannot both be H; R is alkyl of 1–6 carbon atoms, aryl; X is CF$_3$; E is S or O).

9-alkyl derivatives of the compound of formula (Ig: C, D is H or OSO$_2$R; C, D cannot both be H; R is alkyl of 1–6 carbon atoms, aryl; X is alkyl of 1–6 carbon atoms; E is S or O) (Scheme 4) can be prepared by reaction of (If: C, D is H or OSO$_2$R; C, D cannot both be H; R is alkyl of 1–6 carbon atoms, aryl; E is S or O) with three or more molar equivalents of lower tetra-alkyltin in the presence of a palladium catalyst such as 1 to 10 mole % of bis (triphenylphosphine)palladium II chloride in a suitable solvent such as DMF, DMA or 1-methyl-2-pyrrolidinone at temperatures ranging from 140° C. to 200° C.

The sulfonic ester group can then be removed from the sulfonic acid esters of formula (Ig: C, D is H or OSO$_2$R; C, D cannot both be H; R is alkyl of 1–6 carbon atoms, aryl; X is alkyl of 1–6 carbon atoms or lower perfluoroalkyl; E is S or O) to provide the phenols of formula (Ig: C, D is H or OH; C, D cannot both be H; X is alkyl of 1–6 carbon atoms or lower perfluoroalkyl; E is S or O) using standard conditions. These conditions include aqueous base in which one or more molar equivalents of alkali metal hydroxide such as sodium hydroxide is used in water with a co-solvent such as HF, dioxane or a lower alcohol such as methanol or mixtures of THF and a lower alcohol at temperatures ranging from room temperature to 110° C.

9-Alkoxy derivatives of the compound of formula (Ig: C, D is H, OH; C, D cannot both be H; X is alkoxy of 1–6 carbon atoms; E is S or O) can be prepared by reaction of (If: C, D is H or OSO$_2$R; C, D cannot both be H; R is alkyl of 1–6 carbon atoms, aryl; E is S or O) with three or more molar equivalents of lower alkali metal alkoxide such as sodium methoxide in the presence of a copper (I) or copper (II) catalyst such as 1 to 10 mole % copper (II) chloride in a suitable solvent such as DMF, DMA or 1-methyl-2-pyrrolidinone at temperatures ranging from 80° C. to 180° C. Under the reaction conditions, the sulfonic acid group of formula (If: C, D is H or OSO$_2$R; C, D cannot both be H; R is alkyl of 1–6 carbon atoms, aryl; E is S or O) is removed.

9-Sulfanyl derivatives of the compound of formula (Ig: C, D is H or OH; C, D cannot both be H; X is alkyl of 1–6 carbon atomssulfanyl, arylsulfanyl, pyridylsulfanyl, 2-N,N-dimethylaminoethylsulfanyl; E is S or O) can be prepared by reaction of formula (If: C, D is H or OSO$_2$R; C, D cannot both be H; R is alkyl of 1–6 carbon atoms, aryl; E is S or O) with one or more molar equivalents of the appropriate alkyl of 1–6 carbon atomsthiol, arylthiol, thiopyridine or 2-N,N-dimethylaminoethyl-mercaptan, one or more molar equivalents of an alkali metal hydroxide such as sodium hydroxide, one or more molar equivalents of a copper (I) or copper (II) catalyst such as copper (I) oxide in a suitable solvent such as DMF, DMA or 1-methyl-2-pyrrolidinone at temperatures ranging from 100° C. to 180° C. Under the reaction conditions, the sulfonic acid group of formula (If: C, D is H or OSO$_2$R; C, D cannot both be H; R is alkyl of 1–6 carbon atoms, aryl; E is S or O) is removed.

Scheme 5

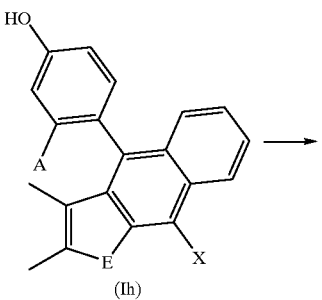

(Ih)

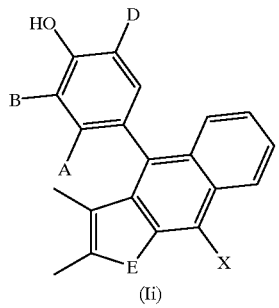

(Ii)

Further derivatives of the compounds of formula (I) in Scheme 5 can be prepared by the following methods. The phenols of formula (Ih: A is H or OH; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be brominated in two positions to afford the dibromphenols of formula (Ii: A is H or OH; B, D is Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) using at least 2 molar equivalents of molecular bromine in an appropriate solvent such as acetic acid. One to fifty molar equivalents of a salt of acetic acid such as potassium or sodium acetate can also be used as a co-reagent in this reaction although it is not absolutely required.

The phenols of formula (Ih: A is H; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be mononitrated to the phenols of formula (Ii: A is H; B is $NO_2$; D is H; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S or O) most conveniently using iron (III) trinitrate in a lower alcohol solvent.

The nitro compounds of formula (Ii: A is H; B is $NO_2$; D is H; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S or O) can be reduced to the amino compounds of formula (Ii: A is H; B is $NH_2$; D is H; X is H, halogen, alkyl of 1–6 carbon atoms, CN, lower perfluoroalkyl, alkoxy of 1–6 carbon atoms, aralkoxy, amino, alkylsulfanyl of 1–6 carbon atoms, arylsulfanyl, pyridylsulfanyl, 2-N,N-dimethylamino-ethylsulfanyl; E is S or O) most readily using tin dichloride in ethylacetate at 40 to 100° C. or with hydrazine and Montmorillinite clay in ethanol at 40 to 100° C.

The nitro compounds of formula (Ii: A is H; B is $NO_2$; D is H; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can also be brominated to the compounds of formula (Ii: A is H; B is $NO_2$; D is Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) using at least 2 molar equivalents of molecular bromine in an appropriate solvent such as acetic acid. One to fifty molar equivalents of a salt of acetic acid such as potassium or sodium acetate can also be used as a co-reagent in this reaction although it is not absolutely required. The bromo nitro compounds of formula (Ii: A is H; B is $NO_2$; D is Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be reduced to the bromo amino compounds of formula (Ii: A is H; B is $NH_2$; D is Br; X is H, halogen, alkyl of 1–6 carbon atoms, CN, lower perfluoroalkyl, alkoxy of 1–6 carbon atoms, aralkoxy, amino, alkylsulfanyl of 1–6 carbon atoms, arylsulfanyl, pyridylsulfanyl, 2-N,N-dimethylaminoethylsulfanyl; E is S or O) most readily using tin dichloride in ethylacetate at 40 to 100° C. or with hydrazine and Montmorillinite clay in ethanol at 40 to 100° C.

The amino compounds of formula (Ii: A is H; B is $NH_2$; D is H or Br; X is H, halogen, alkyl of 1–6 carbon atoms, CN, lower perfluoroalkyl, alkoxy of 1–6 carbon atoms, aralkoxy, amino, alkylsulfanyl of 1–6 carbon atoms, arylsulfanyl, pyridylsulfanyl, 2-N,N-dimethylaminoethylsulfanyl; E is S or O) can be acylated with one or more equivalents of a suitable acylating agent of formula (LG)$COR^{1a}$ or (LG)$CO_2R^{1a}$ (wherein LG is a leaving group such as Cl for an acyl halide or chloroformate or $OCOR^{1a}$ or $OCO_2R^{1a}$ for an anhydride or mixed anyhdride, etc.; $R^{1a}$ is alkyl of 1–6 carbon atoms, aralkyl and aryl) to produce the compounds of formula (Ii: A is H; B is $NHCOR^{1a}$ or $NHCO_2R^{1a}$; D is H or Br; X is H, halogen, alkyl of 1–6 carbon atoms, CN, lower perfluoroalkyl, alkoxy of 1–6 carbon atoms, aralkoxy, amino, alkylsulfanyl of 1–6 carbon atoms, arylsulfanyl, pyridylsulfanyl, 2-N,N-dimethylaminoethylsulfanyl; E is S or O; $R^{1a}$ is $R^{1a}$ is alkyl of 1–6 carbon atoms aralkyl and aryl). These acylations can be performed in the presence of one or more equivalents of a suitable base such as an alkali metal hydroxide, carbonate or bicarbonate or an organic amine base such as triethylamine or pyridine and with or without a suitable solvent such a chloroform, dichloromethane, THF, dioxane and water or mixtures of these solvents and with or without the presence of a catalyst such as 4-N,N-dimethylpyridine.

The dibromo-bisphenols of formula (Ii: A is OH; B, D is Br; X is H; E is S or O) can be further brominated in the 9-position of the naphtho[2,3-b]thiophene or the naphtho[2,3-b]furan ring to form the bisphenols of formula (Ii: A is OH; B, D, X is Br; E is S or O). This bromination reaction is generally done using 1 to 1.3 molar equivalents of molecular bromine in the dark with a catalytic amount of iron (III) chloride in an inert solvent such as dichloromethane or carbon tetrachloride at temperatures ranging from −78° C. to room temperature.

Scheme 6

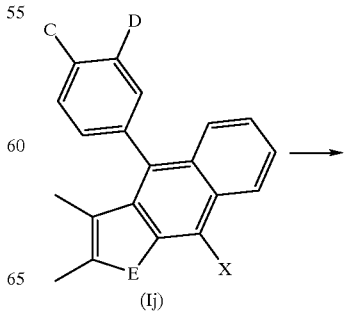

(Ij)

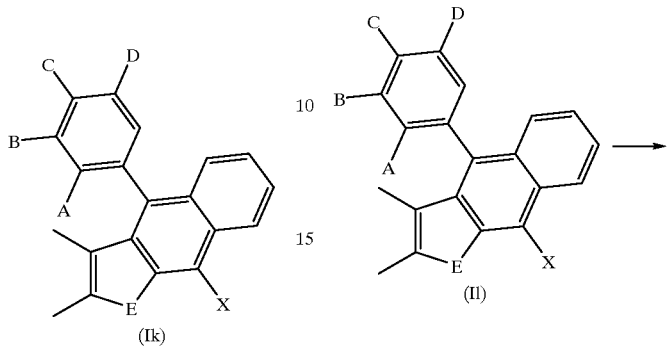

(Ik)

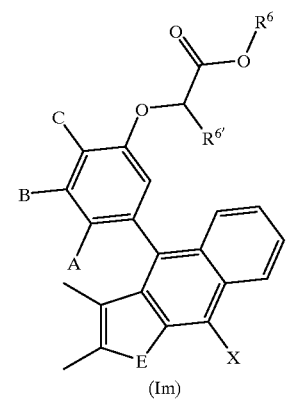

(Im)

Further derivatives of the compounds of formula (I) in Scheme 6 can be prepared by the following methods. The phenols of formula (Ij: C is H; D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be monobrominated to provide the provide the bromophenols of formula (Ik: A, B is H; C is Br; D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) using at least 1 molar equivalent of molecular bromine in an appropriate solvent such as acetic acid or dibrominated to provide the bromophenols of formula (Ik: B is H; A, C is Br; D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) using at least 2 molar equivalents of molecular bromine in an appropriate solvent such as acetic acid. Similarly, the bisphenols of formula (Ij: C, D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be monobrominated to provide a mixture of the bromobisphenols of formula (Ik: A is H; B is Br; C, D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S or O) and (Ik: A is Br; B is H; C, D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; E is S or O) using at least 1 molar equivalents of molecular bromine in an appropriate solvent such as acetic acid. This mixture can be separated into pure monobromo products by conventional means.

Further derivatives of the compounds of formula (I) in Scheme 7 can be prepared by the following methods. The phenols of formula (Il: B is H; A, C is H or Br; D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be alkylated with one or more molar equivalents of an alkyl haloacetate of formula ($X^2CHR^{6a}CO_2R^6$ where $X^2$ is Cl, Br or I and $R^6$ is alkyl of 1–6 carbon atoms, $R^{6a}$ is H) and with one or more molar equivalents of an alkali metal carbonate such as potassium carbonate in a polar aprotic solvent such as DMF to afford the alkylated product of formula (Im: B is H; A, C is H or Br; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms, $R^{6a}$ is H; E is S or O).

Alternatively the bisphenols of formula (Il: A, B is H or Br; C, D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be diaklylated with two or more molar equivalents of an alkyl haloacetate of formula ($X^2CHR^{6a}CO_2R^6$ where $X^2$ is Cl, Br or I and $R^6$ is alkyl of 1–6 carbon atoms, $R^{6a}$ is H) and with two or more molar equivalents of an alkali metal carbonate such as potassium carbonate in a polar aprotic solvent such as DMF to afford the dialkylated esters of formula (Im: A, B is H or Br; C is $OCH_2CO_2R^6$; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$ is alkyl of 1–6 carbon atoms, $R^{6a}$ is H; E is S or O).

Still alternatively, the phenols of formula (II: B is H or halogen; A is H or halogen; C is H, Br or alkoxy of 1–6 carbon atoms; D is OH; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; E is S or O) can be reacted with a 2-hydroxy carboxylic acid ester of formula CH(OH)($R^{6a}$)$CO_2R^6$ ($R^6$, $R^{6a}$ is alkyl of 1–6 carbon atoms, aralkyl, aryl) to afford the esters of formula (Im: B is H or halogen; A is H or halogen; C is H, Br or alkoxy of 1–6 carbon atoms; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$, $R^{6a}$ is alkyl of 1–6 carbon atoms, aralkyl, aryl; E is S or O) under the conditions of the Mitsunobu Reactions (for a review see Oyo Mitsunobu *Synthesis.* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from –20° C. to 120° C.

The monoesters of formula (Im: A, B is H or halogen; C is H, Br or alkoxy of 1–6 carbon atoms; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$, $R^{6a}$ is alkyl of 1–6 carbon atoms, aralkyl, aryl; E is S or O) as well as the diesters of formula (Im: A, B is H or Br; C is $OCH_2CO_2R^6$, X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$ is alkyl of 1–6 carbon atoms, $R^{6a}$ is H; E is S or O) can be transformed into their carboxylic acid analogs using standard conditions to afford the moncarboxylic acids of formula (Im: A, B is H or halogen; C is H, Br or alkoxy of 1–6 carbon atoms; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; $R^6$ is H; $R^{6a}$ is alkyl of 1–6 carbon atoms, aralkyl, aryl; E is S or O) and the dicarboxylic acids of formula (Im: A, B is H or Br; C is $OCH_2CO_2H$, X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; $R^6$, $R^{6a}$ is H; E is S or O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

Scheme 8

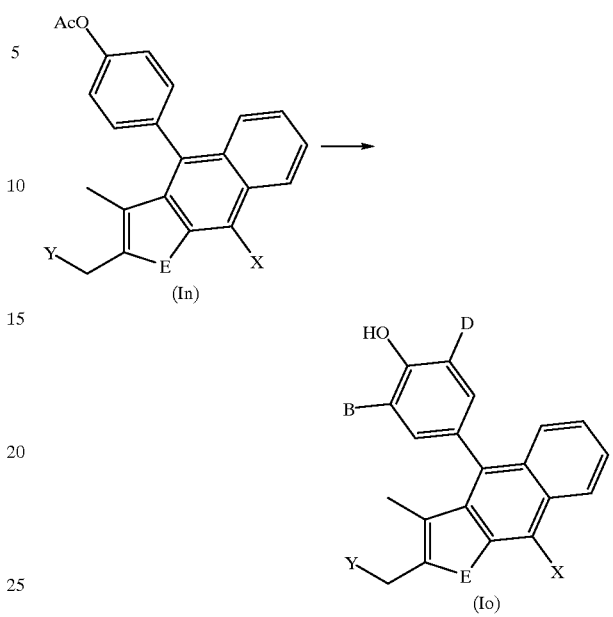

Further derivatives of the compounds of formula (I) in Scheme 8 can be prepared by the following methods. The acetates of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H; E is S or O) can be reacted with a halogenating agent, specifically one that causes benzylic type bromination or chlorination such as one or more molar equivalents of N-bromosuccinimide, N-chlorosuccinimide or sulfuryl chloride to provide the halo acetates of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br; E is S or O). This reaction is conveniently done in a suitable solvent such as dichloromethane or carbontetrachloride at temperatures ranging from 0° C. to room temperature.

The halo acetates of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br; E is S or O) can be reacted with one or more equivalents of nucleophiles such as alkoxides ($MOR^1$), sulfides ($MSR^1$) or amines ($NHR^1R^2$) (wherein M is a alkali metal such as Na, Li or K; $R^1$, $R^2$ is H, alkyl of 1–6 carbon atoms, aryl or aralkyl) in a suitable solvent such as THF, DMF or dichloromethane to provide the compounds of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is $OR^1$, $SR^1$, $NR^1R^2$, where $R^1$, $R^2$ is H, alkyl of 1–6 carbon atoms, aryl or aralkyl; E is S or O). During reaction of the compounds of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br; E is S or O) with nucleophiles there can be concomitent loss of the acetyl group to afford the compounds of formula (Io: B, D is H; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is $OR^1$, $SR^1$, $NR^1R^2$, where $R^1$, $R^2$ is H, alkyl of 1–6 carbon atoms, aryl or aralkyl; E is S or O).

The compounds of formula (In: X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is $OR^1$, $SR^1$, $NR^1R^2$, where $R^1$, $R^2$ is H, alkyl of 1–6 carbon atoms, aryl or aralkyl; E is S or O) can be deacylated to produce the compounds of formula (Io: B, D is H; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br, $OR^1$, $SR^1$, $NR^1R^2$, where $R^1$, $R^2$ is H, alkyl of 1–6 carbon atoms, aryl or aralkyl; E is S or O). The deacylation conditions include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acid conditions may also be employed in which the compound is reacted with one or more molar equivalents of a mineral acid such as HCl or sulfuric acid in water with or without a co-solvent such as THF at temperatures ranging from room temperature to 80° C.

The compounds of formula (Io: B, D is H; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br, $OR^1$, $SR^1$, $NR^1R^2$, where $R^1$, $R^2$ is H, alkyl of 1–6 carbon atoms, aryl or aralkyl; E is S or O) can be brominated in two positions to afford the dibromphenols of formula (Io: B, D is Br; X is halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is Cl, Br, $OR^1$, $SR^1$, $NR^1R^2$, where $R^1$, $R^2$ is H, alkyl of 1–6 carbon atoms, aryl or aralkyl; E is S or O) using at least 2 molar equivalents of molecular bromine in an appropriate solvent such as acetic acid. One to fifty molar equivalents of a salt of acetic acid such as potassium or sodium acetate can also be used reagent in this reaction although it is not absolutely required.

Scheme 9

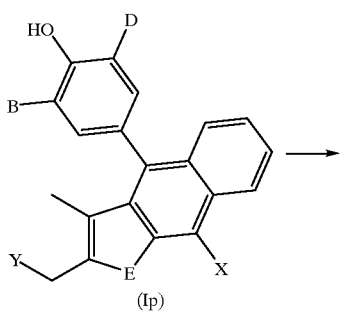

(Ip)

-continued

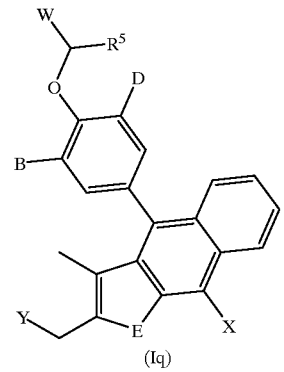

(Iq)

Further derivatives of the compounds of formula (I) in Scheme 9 can be prepared by the following methods. The phenols of formula (Ip: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be alkylated with one or more molar equivalents of an alkyl haloacetate of formula ($X^2CH_2CO_2R^6$ where $X^2$ is Cl, Br or I and $R^6$ is alkyl of 1–6 carbon atoms) and with one or more molar equivalents of an alkali metal carbonate such as potassium carbonate in a polar aprotic solvent such as DMF to afford the alkylated product of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2R^6$; $R^5$ is H; $R^6$ is alkyl of 1–6 carbon atoms; E is S or O).

The phenols of formula (Ip: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be reacted with a 2-hydroxy carboxylic acid ester of formula $CH(OH)(R^5)CO_2R^6$ ($R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms) to afford the esters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms; E is S or O) under the conditions of the Mitsunobu Reactions (for a review see Oyo Mitsunobu *Synthesis*. 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The 2-hydroxy carboxylic acid ester of formula $CH(OH)(R^5)CO_2R^6$ ($R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms) are commercially available or can be prepared from commercially available carboxylic acid precursors under standard esterification conditions. (S)-(+)-2-Hydroxy-1-oxo-3-dihydro-2-isoindolinebutyric acid, methyl ester can be prepared from (S)-(+)-2-hydroxy-1,3-dioxo-2-isoindolinebutyric acid, methyl ester via sequential treatment with 1) sodium borohydride in THF-water; 2) trifluoroacetic acid/chloroform; 3) triethylsilane/trifluoroacetic acid and 4) aqueous sodium bicarbonate. 3-(Pyridin-3-yl)-phenyllactic acid, ethyl ester can be prepared according to the two step procedure of B. A. Lefker, W. A. Hada, P. J. McGarry *Tetrahedron Lett.* 1994, 35, 5205–5208, from commericially available 3-pyridinecarboxaldehyde and ethyl chloroacetate.

The esters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2tBu$; $R^5$ is H; E is S or O) can be treated with one or more molar equivalents of a strong base such as lithium diisopropyl amide in a suitable solvent such as THF at temperatures ranging from −78° C. to room temperature. This procedure produces an anion alpha to the ester carbonyl. The resultant anion is treated with one or more molar equivalents of an alkyl halide of formula $X^2R^5$ (where $X^2$ is halogen; $R^5$ is alkyl and aralkyl) and warmed to room temperature to produce the alkylated ester of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2tBu$; $R^5$ is alkyl and aralkyl; E is S or O).

The esters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2R^6$, $R^6$ is alkyl of 1–6 carbon atoms; E is S or O) can be transformed into their carboxylic acid analogs using standard conditions to afford the carboxylic acids of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2H$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl), $CH_2CO_2H$; E is S or O). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Alternatively, acid conditions may also be employed in which the aboved mentioned carboxylic acid ester of formula (Iq) is reacted with one or more molar equivalents of a mineral acid such as HCl or sulfuric acid in water with or without a co-solvent such as THF at temperatures ranging from room temperature to 80° C. Still alternatively, many other conditions may be employed to effect the above mentioned ester to acid transformation leading to (Iq). These include reacting the carboxylic acid ester of formula (Iq) with one or more molar equivalents of boron tribromide or boron trichloride in dichloromethane at −78° C. to room temperature; one or more molar equivalents hydrobromic acid in acetic acid at 0° C. to 50° C.; one or more molar equivalents trimethylsilylbromide or trimethylsilyliodide in dichloromethane, carbon tetrachloride or acetonitrile at −78° C. to 50° C.; one or more molar equivalents lithium iodide in pyridine or quinoline at temperatures from 100° to 250° C.

The phenols of formula (Ip: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be alkylated with one or more molar equivalents of diethyl trifluoromethylsulfonyloxymethylphosphanate (D. P. Phillion and S. S. Andrew *Tet. Lett.* 1986, 1477–1480) and with one or more molar equivalents of an alkali metal hydride such as sodium hydride in a suitable solvent such as THF or DMF to afford the diethylphosphonate product of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $PO_3Et_2$; $R^5$ is H; $R^6$ is alkyl of 1–6 carbon atoms; E is S or O).

The phenols of formula (Ip: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be reacted with a 2-hydroxy phosphonic acid diester of formula $CH(OH)(R^5)PO_3(R^6)_2$, ($R^5$ is H, alkyl of 1–6 carbon atoms, aralkyl, aryl, $R^6$ is alkyl of 1–6 carbon atoms) to afford the phosphonic acid diesters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $PO_3(R^6)_2$; $R^5$ is H, alkyl of 1–6 carbon atoms, aralkyl, aryl, $R^6$ is alkyl of 1–6 carbon atoms; E is S or O) under the conditions of the Mitsunobu Reactions (for a review see Oyo Mitsunobu *Synthesis* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C.

The 2-hydroxy phosphonic acid diester of formula $CH(OH)(R^5)PO_3R^6$ ($R^5$ is H, alkyl of 1–6 carbon atoms, aralkyl, aryl, $R^6$ is alkyl of 1–6 carbon atoms) can be prepared by reacting a dialklylphosphonate of formula $HP(O)(OR^6)_2$ ($R^6$ is alkyl of 1–6 carbon atoms) with an aldehyde of formula $R^5CHO$ ($R^5$ is H, alkyl of 1–6 carbon atoms, aryl, aralkyl) under standard conditions.

The phosphonic acid diesters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $PO_3(R^6)_2$; $R^5$ is H, alkyl of 1–6 carbon atoms, aralkyl, aryl, $R^6$ is alkyl of 1–6 carbon atoms; E is S or O) can be transformed into their phosphonic acid analogs using standard conditions to afford the phosphonic acids of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $PO_3H_2$; $R^5$ is H, alkyl of 1–6 carbon atoms, aralkyl, aryl, $R^6$ is H, alkyl of 1–6 carbon atoms; E is S or O). The conditions that may also be employed in which the above mentioned phosphonic acid diester of formula (Iq) is reacted with two or more molar equivalents of a mineral acid such as HCl or sulfuric acid in water with or without a co-solvent such as THF at temperatures ranging from 40 to 100° C. Still alternatively, many other conditions may be employed to effect the above mentioned diester to acid transformation leading to (Iq). These include reacting the phosphonic acid diester of formula (Iq) with two or more molar equivalents of boron tribromide or boron trichloride in dichloromethane at −78° C. to room temperature; two or more molar equivalents hydrobromic acid in acetic acid at 0° C. to 50° C.; two or more molar equivalents trimethylsilylbromide or trimethylsilyliodide in dichloromethane, carbon tetrachloride or acetonitrile at −78° C. to 50° C.; two or more molar equivalents lithium iodide in pyridine or quinoline at temperatures from 60° to 250° C.

The esters of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2R^6$; $R^5$ is H, alkyl of 1–6 carbon atoms, aralkyl, aryl, $CH_2$(1H-imidazol-4-yl), $CH_2$(3-1H-indolyl), $CH_2CH_2$(1-oxo-1,3-dihydro-isoindol-2-yl), $CH_2$(3-pyridyl), $R^6$ is alkyl of 1–6 carbon atoms; E is S or O) can be transformed into their primary carboxylic acid amide analogs of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CONH_2$; $R^5$ is H, alkyl of 1–6 carbon atoms, aralkyl, aryl, $CH_2$(1H-imidazol-4-yl), $CH_2$(3-1H-indolyl), $CH_2CH_2$(1-oxo-1,3-dihydro-isoindol-2-yl), $CH_2$(3-pyridyl); E is S or O) by reacting the ester starting material with ammonia gas dissolved in a lower alcohol solvent such as methanol or ethanol at temperatures ranging from 0° C. to 100° C.

Alternatively, the carboxylic acids of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CO_2H$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S or O) can be transformed into their carboxylic acid amide analogs of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CONH_2$, CONHOH, $CONH(CH_2)_2CN$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S or O). This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C.

The phenols of formula (Ip: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Br, $OR^1$, $SR^1$, $NR^1R^2$, where $R^1$, $R^2$ is H, alkyl of 1–6 carbon atoms, aryl or aralkyl; E is S or O) can be alkylated with one or more molar equivalents of a haloacetonitrile of formula ($X^2CH_2CN$ where $X^2$ is Cl, Br or I) and with one or more molar equivalents of an alkali metal carbonate such as potassium carbonate in a polar aprotic solvent such as DMF to afford the nitriles of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is CN; R is H; E is S or O).

Alternatively, the carboxylic acid amide analogs of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is $CONH_2$; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S or O) can be converted to their nitrile analogs of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is CN; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3dihydro-isoindol-2-yl), $CH_2CH_2$(1-oxo-1,3-dihydro-isoindol-2-yl), $CH_2$(3-pyridyl); E is S or O) by using reagents that dehydrate the primary carboxamide function to the nitrile function. One set of conditions to effect this transformation include reacting the said primary carboxylic acid amide with one or more molar equivalents of trifluoroacetic anhydride and two or more molar equivalents of pyridine in a suitable solvent such as dioxane at temperatures ranging from 60° C. to 120° C.

The nitriles analogs of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is CN; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S or O) can be converted to the tetrazoles of formula (Iq: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; W is 5-tetrazole; $R^5$ is H, alkyl of 1–6 carbon atoms, aralkyl, aryl, $CH_2$(1H-imidazol-4-yl), $CH_2$(3-1H-indolyl), $CH_2CH_2$(1,3-dioxo-1,3-dihydro-isoindol-2-yl), $CH_2CH_2$(1-oxo-1,3-dihydro-isoindol-2-yl), $CH_2$(3-pyridyl); E is S or O) by reacting the nitrile function with one or more molar equivalents of trimethylaluminum and one or more molar equivalents of trimethylsilyl azide in a suitable solvent such as benzene or toluene at temperatures ranging from 60° C. to 120° C. Alternatively, the nitrile fuction can be reacted with one or more molar equivalents of ammonium azide in a suitable solvent such as dimethylformamide at temperatures ranging from 60° C. to 160° C.

Scheme 10

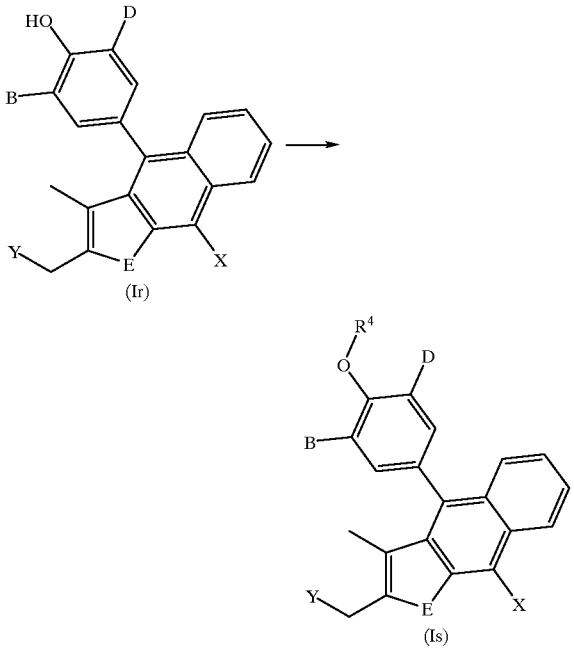

Further derivatives of the compounds of formula (I) in Scheme 10 can be prepared by the following methods. The phenols of formula (Ir: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be reacted with one or more molar equivalents of lithium (bis)trimethylsilylamide at temperatures ranging from −78° C. to room temperature and the lithium salt can be further reacted with one or more molar equivalents of 5-bromothiazolidine-2,4-dione (prepared according to the method of Zask, et al., *J. Med Chem*, 1990, 33, 1418–1423) using a suitable solvent such as THF under an inert atmosphere at temperatures ranging from −78° C. to room temperature to provide the compounds of formula (Is: $R^4$ is (R, S)-5-thiazolidine-2,4-dione; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O).

Alternatively, the phenols of formula (Ir: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be reacted with one or more molar equivalents of tetrazole and di-tert-butyl N,N-diethylphosporamidate in THF at room temperature followed by addition of one or more molar equivalents of meta-chlorobenzoic acid at −40° C. according to the procedure of J. W. Perich and R. B. Johns, *Synthesis*, 1988, 142–144) to afford the phosphate diesters of formula (Is: $R^4$ is $P(O)(OtBu)_2$; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O). These phosphate diesters are then treated with one or more molar equivalents hydrochloric acid in a suitable solvent such as dioxane to provide the phosphonic acids of formula (Is: $R^4$ is $P(O)(OH)_2$; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O).

The phenols of formula (Ir: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be transformed to the carboxylic acids of formula (Is: $R^4$ is $C(CH_3)_2CO_2H$; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) by treatment of the phenols with two or more molar equivalents of solid sodium hydroxide followed by one or more molar equivalents of 1,1,1-trichloro-2-methyl-2-propanol tetrahydrate in the presence of a large excess of acetone which also serves as solvent.

The phenols of formula (Ir: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be transformed to the carboxylic acids of formula (Is: $R^4$ is $CH_2CH_2CO_2H$; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) by treatment with one or more molar equivalents of β-propiolactone and treatment with one or more molar equivalents of potassium tert-butoxide in a suitable solvent such as THF.

The phenols of formula (Ir: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be reacted with a 3-hydroxy carboxylic acid ester of formula $CH(OH)(R^7)CH_2CO_2R^6$ ($R^7$ is H or alkyl of 1–6 carbon atoms; $R^6$ is alkyl of 1–6 carbon atoms) to afford the esters of formula (Is: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) under the conditions of the Mitsunobu Reactions (for a review see Oyo Mitsunobu *Synthesis* 1981, 1–27). The other co-reagents necessary to effect the Mitsunobu Reaction include one or more molar equivalents of a alkyl of 1–6 carbon atoms azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene or toluene at temperatures ranging from −20° C. to 120° C. at temperatures ranging from −20° C. to 120° C.

The 3-hydroxy carboxylic acid ester of formula $CH(OH)(R^7)CH_2CO_2R^6$ ($R^7$ is H or alkyl of 1–6 carbon atoms; $R^6$ is alkyl of 1–6 carbon atoms) are commercially available or can be prepared from commercially available carboxylic acid precursors under standard esterification conditions.

The esters of formula (Is: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) can be transformed to the acids of formula (Is: $R^4$ is (R)—$CH(R^7)CH_2CO_2H$; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylamino-ethylsulfanyl; Y is H, Cl, Br, $OR^1$, $SR^1$, $NR^1R^2$, where $R^1$, $R^2$ is H, alkyl of 1–6 carbon atoms, aryl or aralkyl; E is S or O) by several standard conditions which include reacting the ester of formula (Is) with two or more molar equivalents of a mineral acid such as HCl or sulfuric acid in one or more solvents or a combination of two or more solvents such as water, THF, or dioxane at temperatures ranging from 40 to 120° C. Still alternatively, many other conditions may be employed to effect the above mentioned ester to acid transformation leading to (Is). These include reacting the esters of formula (Is) with two or more molar equivalents of boron tribromide or boron trichloride in dichloromethane at −78° C. to room temperature; two or more molar equivalents hydrobromic acid in acetic acid at 0° C. to 50° C.; two or more molar equivalents trimethylsilylbromide or trimethylsilyliodide in dichloromethane, carbon tetrachloride or acetonitrile at −78° C. to 50° C.; two or more molar equivalents lithium iodide in pyridine or quinoline at temperatures from 60° to 250° C.

The nitrophenols of formula (Ir: B is $NO_2$; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O) can be alkylated with one or more molar equivalents of an alkyl or aralkyl halide of formula ($XR^4$ where X is Cl, Br or I and $R^4$ is alkyl of 1–6 carbon atoms, aralkyl ) and with one or more molar equivalents of an alkali metal carbonate such as potassium carbonate in a polar aprotic solvent such as DMF to afford the alkylated product of formula (Is: B is $NO_2$; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O; $R^4$ is alkyl of 1–6 carbon atoms, aralkyl).

The nitro compounds of formula (Is: B is $NO_2$; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O; $R^4$ is alkyl of 1–6 carbon atoms, aralkyl) can be reduced to the amino compounds of formula (Is: B is $NH_2$; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O; $R^4$ is alkyl of 1–6 carbon atoms, aralkyl) most readily using tin dichloride in ethylacetate at 40 to 100° C. or with hydrazine and Montmorillinite clay in ethanol at 40 to 100° C.

The amino compounds of formula (Is: B is $NH_2$; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O; $R^4$ is alkyl of 1–6 carbon atoms, aralkyl) can be alkylated with one or more molar equivalents of an alkyl haloacetate of formula ($X^2CHR^{6a}CO_2R^6$ where $X^2$ is Cl, Br or I and $R^6$ is alkyl of 1–6 carbon atoms, $R^{6a}$ is H) and with one or more molar equivalents of an alkali metal carbonate such as potassium carbonate in a polar aprotic solvent such as DMF to afford the alkylated product of formula (Is: B is $NCHR^{6a}CO_2R^6$; $R^6$ is alkyl of 1–6 carbon atoms; $R^{6a}$ is H or alkyl of 1–6 carbon atoms; D is H or Br; X is H, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl; E is S or O; $R^4$ is alkyl of 1–6 carbon atoms, aralkyl). These esters can be transformed into their carboxylic acid analogs using standard conditions to afford the carboxylic acids of formula (Is: B is $NCHR^{6a}CO_2H$; $R^{6a}$ is H or alkyl of 1–6 carbon atoms; D is H or Br; X is H, halogen, alkyl of 1–6 carbon atoms, CN, lower perfluoroalkyl, alkoxy of 1–6 carbon atoms, aralkoxy, nitro, alkylsulfanyl of 1–6 carbon atoms, arylsulfanyl, pyridylsulfanyl, 2-N,N-dimethylaminoethylsulfanyl; Y is H, $OR^1$, $SR^1$, $NR^1R^2$, where $R^1$, $R^2$ is H, alkyl of 1–6 carbon atoms, aryl or aralkyl;

E is S or O; $R^4$ is alkyl of 1–6 carbon atoms, aralkyl). The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C.

Scheme 11

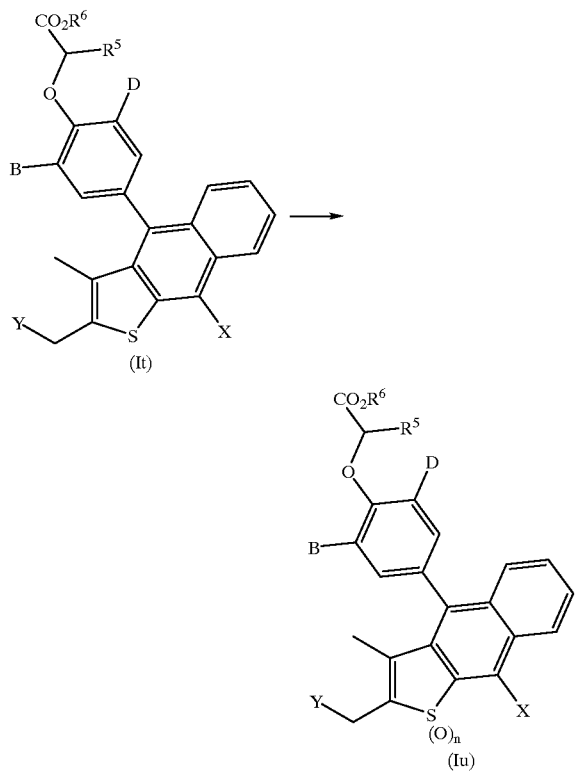

Further derivatives of the compounds of formula (I) in Scheme 11 can be prepared by the following methods. The compounds of formula (It: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro; Y is Cl, Br, $OR^1$ where $R^1$, $R^2$ is H, alkyl of 1–6 carbon atoms, aryl or aralkyl; $R^5$ is H, alkyl of 1–6 carbon atoms, aryl or aralkyl; $R^6$ is H, alkyl of 1–6 carbon atoms) can be transformed into their sulfoxide derivatives of formula (Iu: n is 1; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro; Y is Cl, Br, $OR^1$ where $R^1$, $R^2$ is H, alkyl of 1–6 carbon atoms, aryl or aralkyl; $R^5$ is H, alkyl of 1–6 carbon atoms, aryl or aralkyl; $R^6$ is H, alkyl of 1–6 carbon atoms) using one molar equivalent of an oxidizing agent such as m-chloroperbenzoic acid in dichloromethane at temperatures ranging from −20° C. to 40° C. or peracetic aid in acetic acid and water at temperatures ranging from room temperature to 100° C.

The compounds of formula (It: B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro; Y is Cl, Br, $OR^1$ where $R^1$, $R^2$ is H, alkyl of 1–6 carbon atoms, aryl or aralkyl; $R^5$ is H, alkyl of 1–6 carbon atoms, aryl or aralkyl; $R^6$ is H, alkyl of 1–6 carbon atoms) can be transformed into their sulfone derivatives of formula (Iu: n is 2; B, D is H, halogen, CN, alkyl of 1–6 carbon atoms, aryl, aralkyl, nitro; X is H, halogen, alkyl of 1–6 carbon atoms, CN, lower perfluoroalkyl, alkoxy of 1–6 carbon atoms, aralkoxy, nitro; Y is Cl, Br, $OR^1$ where $R^1$, $R^2$ is H, alkyl of 1–6 carbon atoms, aryl or aralkyl; $R^5$ is H, alkyl of 1–6 carbon atoms, aryl or aralkyl; $R^6$ is H, alkyl of 1–6 carbon atoms) using two or more molar equivalents of an oxidizing agent such as m-chloroperbenzoic acid in dichloromethane at temperatures ranging from −20° C. to 60° C. or peracetic aid in acetic acid and water at temperatures ranging from room temperature to 100° C.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-Phosphorylated Insulin Receptor Dodecaphosphopeptide Dephosphorylation by Rat Hepatic Protein-tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction

Rats (Male Sprague-Dawley rats (Charles River, Kingston, N.Y.) weighing 100–150 g, maintained on standard rodent chow (Purina)) are sacrificed by asphyxiation with CO2 and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40 C. The supernatant is decanted and centrifuged at 100,00×g for 60 minutes at 40 C. The pellet, microsomes and small vesicles, is resuspended and lightly homogenized in: 20 mM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml;H5B antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum albumin as a standard (Pierce Chemical Co., Rockford, Ill.).

Measurement of PTPase Activity

The malachite green-ammonium molybdate method, as described by Lanzetta P A, Alvarez L J, Reinach P S, Candia O A was used. An improved assay for nanomolar amounts of inorganic phosphate. *Anal. Biochem.* 1979;100:95–97, and adapted for the platereader, is used for the nanomolar detection of liberated phosphate by rat hepatic microsomal PTPases. The test procedure uses, as substrate, a dodecaphosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg. C. with or without test compound (6.25 ul) and 305.5 ul of the 81.83 mM HEPES reaction buffer, pH 7.4. Peptide substrate, 10.5 ul at a final concentration of 50 uM, is equilibrated to 37 deg. C. in a LABLINE Multi-Blok heater equipped with a titerplate adapter. The preincubated microsomal preparation (39.5 ul) with or without drug is added to initiate the dephosphorylation reaction, which proceeds at 37 deg. C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations

PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 $\mu$M. The following results were obtained using representative compounds of this invention.

| Example | % Change from Control |
|---|---|
| 9 | −49.80 |
| 19 | −30.40 |
| 20 | 2.13 |
| 21 | −63.12 |
| 22 | −28.57 |
| 23 | −26.11 |
| 24 | −65.31 |
| 29 | −83.54 |
| 30 | −60.32 |
| 31 | −63.42 |
| 32 | −89.41 |
| 33 | −61.92 |
| 34 | −63.01 |
| 35 | −58.85 |
| 36 | −67.00 |
| 37 | −49.83 |
| 38 | −57.74 |
| 40 | −83.88 |
| 41 | −39.60 |
| 42 | −63.41 |
| 43 | −78.84 |
| 44 | −68.50 |
| 45 | −94.50 |

| Example | % Change from Control |
|---|---|
| 46 | −91.00 |
| 47 | −68.48 |
| 48 | −44.69 |
| 49 | −89.36 |
| 50 | −81.27 |
| 52 | −87.66 |
| 53 | −81.83 |
| Phenylarsine oxide (reference standard) | −57.06 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 μg/ml protein in 33 mM Tris-HCl, 2 mM EDTA, 10% glycerol and 10 mM 2-mercaptoethanol.

Measurement of PTPase Activity

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations

PTPased on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN is used for determining $IC_{50}$ values of test compounds. The following results were obtained.

| Example | IC50 (μM) |
|---|---|
| 9 | 0.539 |
| 19 | 0.697 |
| 21 | 0.381 |
| 23 | 0.743 |
| 29 | 0.115 |
| 30 | 0.869 |
| 31 | 0.049 |
| 32 | 0.060 |
| 33 | 0.029 |
| 34 | 0.100 |
| 35 | 0.273 |
| 36 | 1.34 |
| 37 | 0.352 |
| 38 | 0.299 |
| 39 | 1.74 |
| 40 | 0.110 |
| 41 | 0.729 |
| 42 | 0.089 |
| 43 | 0.171 |
| 44 | 0.237 |
| 45 | 0.203 |
| 46 | 1.19 |
| 47 | 0.095 |
| 48 | 0.083 |
| 49 | 0.384 |
| 50 | 0.457 |
| 51 | 2.21 |
| 52 | 0.287 |
| 53 | 0.204 |
| 54 | 0.982 |
| 55 | 0.059 |
| 56 | 0.489 |
| 57 | 1.90 |
| 59 | 2.20 |
| 60 | 1.51 |
| 61 | 0.164 |
| 62 | 0.028 |
| 63 | 0.138 |
| 64 | 0.39 |
| 65 | 0.36 |
| 68 | 0.080 |
| 70 | 0.33 |
| 71 | 1.19 |
| 72 | 0.48 |
| 76 | 0.45 |
| 78 | 0.27 |
| 79 | 0.78 |
| 83 | 0.13 |
| 88 | 0.32 |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of representative compounds of this invention were demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4,7 or 14 two drops of blood (approximately 50 ul) were collected into sodium fluoride containing tubes either from the tail vein or after decapitation. For those studies in which the compound was administered daily by gavage the blood samples were collected 0 and 4 hours after compound administration. The plasma was isolated by centrifugation and the concentration of glucose is measured enzymatically on an Abbott V. P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle | % Change Insulin from Vehicle |
|---|---|---|---|
| 29 | 100 | −48.63 | −89.59 |
| 29 | 25 | −38.18 | −80.50 |
| 29 | 10 | −18.6 (a) | −48.11 |
| 32 | 25 | −15.68(a) | −48.35 |
| 33 | 25 | −21.10(a) | −39.3 |
| 35 | 25 | −25.58 | −2.98(a) |
| 40 | 100 | −28.20 | −90.80 |
| 42 | 25 | −32.5 | b |
| 43 | 25 | −45.2 | b |
| 44 | 25 | −17.2 | b |
| 48 | 25 | −20.1 | b |
| 49 | 10 | −35.1 | b |
| 61 | 10 | −32.8 (c) | b |
| Ciglitazone (reference standard | 100 | −43 | −39 | a - no significant activity (p < 0.05) at this dose.
b - not measured
c - measured at 0 hour Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

2.3-Dimethyl-thiophene

A mixture of 3-methyl-thiophene-carboxaldehyde (20 g, 0.159 mol), hydrazine hydrate (31 mL) and diethylene glycol (72 mL) was heated to reflux for 20 min. After cooling below 100° C., potassium hydroxide (22.9 g, 0.408 mol) was added and the reaction mixture was heated at 125–130° C. for 1.5 h. The reaction mixture was cooled to room temperature and added to water. This aqueous mixture was extracted with ether and the ether phase was washed with 5% aqueous HCl and brine. After drying (magnisium sulfate) the solvent was removed and the oil was flash chromatograghed (pentane as eluent) to provide the title compound as an oil (15.81 g, 89%): NMR (CDCl3); δ6.97 (d, 1H, J=8 Hz), 6.77 (d, 1H, J=8 Hz), 2.35 (s, 3H), 2.14 (s, 3H).

EXAMPLE 2

4,5-Dimethylthiophene-2-yl-(phenyl)-methanol n-Butyl lithium (19.6 ml, 49.1 mmol, 2.5 N in hexanes) was added dropwise to a stirred solution of 2,3-dimethylthiophene (5.0 g, 44.6 mmol) in THF (100 mL) at −78° C. under a dry nitrogen atmosphere. The solution was warmed to 0° C. for 30 min and recooled to −78° C. whereupon benzaldehyde (5.0 mL, 49.1 mmol ) was added. After an additional 45 minutes, sat. aq. ammonium chloride was added and the reaction mixture was partitioned between water and ether. The ether phase was washed with brine and concentrated. The resultant oil was triturated with pet. ether to provide the title compound as a white solid (7.77 g, 80%): mp 80–81° C.: NMR (CDCl3); δ7.45 (ddd, J=8, 1, 1 Hz, 2H), 7.37 (ddd, J=8, 8, 1 Hz, 2H), 7.3 (m, 1H), 6.57 (s, 1H), 6.93 (s, 1H, OH), 2.29 (s, 3H), 2.05 (s, 3H); MS (EI) (M+) 218 (45%, MI): Anal. Calc. for C13H14OS: C, 71.52; H, 6.46; N, 0.00. Found: C, 71.41; H, 6.42; N, 0.09.

EXAMPLE 3

2-Benzyl-4,5 dimethylthiophene

Trifluoroacetic acid (50 mL) was added dropwise over a 60 minute period to a stirred, 0° C. suspension of 4,5-dimethylthiophene-2-yl-(phenyl)-methanol (7.7 g, 35.3 mmol), sodium borohydride (6.67 g, 177 mmol) and ether (600 mL). After an additional 1.5 hours the reaction mixture was added to 10% aqueous sodium hydroxide (600 mL) and stirred for 30 minutes. The layers were separated and the ether phase was washed with 10% aqueous sodium hydroxide, brine and dried (magnesium sulfate). The ether phase was concentrated to provide the title compound as a an oil (6.73 g, 94%): NMR (CDCl3); δ7.33–7.19 (m, 5H), 6.47 (s, 1H), 4.03 (s, 2H), 2.27 (2, 3H), 2.06 (s, 2H); MS (EI) (M+) 202 (45%, MI).

EXAMPLE 4

(2-Benzyl-4,5-dimethyl-thiophen-3-yl)-(4-methoxy-phenyl)-methanone

Tin tetrachloride (4.6 mL, 71.76 mmol) was added dropwise over a 10 minute period to a stirred, −78° C. solution of 2-benzyl-4,5-dimethylthiophene (6.6 g, 32.62 mmol), anisoyl chloride (5.90 g, 34.6 mmol) and dichloromethane (120 mL) under a dry nitrogen atmosphere. After 5 hours at −78° C., the reaction mixture was slowly warmed to room temperature over a 2 h period. The reaction mixture was added to water and extracted with ether. The ether extract was washed with sat. aq. sodium bicarbonate and brine. The solvent was removed and the resultant solid was triturated with ether to give the title compound as a off-white solid (9.62 g, 88%) mp 85–86° C.: NMR (CDCl3); δ7.80 (ddd, J=8, 8, 1 Hz, 2H), 7.24–7.10 (m, 5H), 7.92 (ddd, J=8, 8, 1 Hz, 2H), 3.93 (s, 2H), 3.88 (s, 3H), 2.28 (s, 3H), 1.90 (s, 3H); MS (EI): 336 (100%, MI); Anal. Calc. for C21H20O2S: C, 74.97; H, 5.99; N, 0.00. Found: C, 75.11; H, 6.02; N, 0.05.

EXAMPLE 5

4-(2,3-Dimethyl-naphtho[2,3-b]thiophen-4-yl-phenol

Neat boron tribromide (20 mL, 212 mmol) was added dropwise to a stirred solution of (2-benzyl-4,5-dimethyl-thiophen-3-yl)-(4-methoxy-phenyl)-methanone (9.40 g, 27.9 mmol) in dichloromethane (95 mL) at −78° C. under a dry nitrogen atomosphere. The solution was allowed to warm to ambient temperature and was stirred for 4 h. The reaction mixture was cooled to 0° C. and carefully quenched with water and the solvent was removed. More water was added and the resultant solid was filtered and washed with water and triturated with pet. ether to provide the title compound as a light purple solid (8.23 g, 97%): mp: 165–168° C.; NMR (DMSO-d6); δ9.62 (s, 1H), 8.43 (s, 1H), 7.94 (d, J=8 Hz, 1H), 7.43 (m, 2H), 7.32 (ddd, J=8, 1, 1 Hz, 1H), 7.11 (d, J=8 Hz, 2H), 6.90 (d, J=9 Hz, 2H), 2.39 (s, 3H), 1.61 (s, 3H); MS (EI): 304 (100%, MI).

EXAMPLE 6

Acetic Acid 4-(2,3-dimethyl-naphtho[2,3-b]thiophen-4-yl)-phenyl ester

Acetic anhydride (0.68 mL, 7.20 mmol) was added to a 0° C., stirred solution of 4-(2,3-dimethyl-naphtho[2,3-b]thiophen-4-yl)-phenol (2.0 g, 6.57 mmol) in pyridine (8.6 mL). After 17 h the reaction mixture was added to 5% aqueous HCl and the resulting solid was filtered and washed with 5% aqueous HCl, water and triturated with pet. ether. It was then dried in vacuo to provide the title compound as a white solid (1.99 g, 88%): mp: 147–150° C.; NMR (DMSO-d6); δ8.49 (s, 1H), 7.94 (d, J=8 Hz, 1H), 7.46 (ddd, J=8, 6, 2, 1H), 7.38 (ddd, J=8, 1, 1 Hz, 1H), 7.39–7.34 (m, 2H), 7.28 (d, J=8 Hz, 2H), 6.90 (d, J=9 Hz, 2H), 2.40 (d, J=1 Hz, 3H), 2.34 (s, 3H), 1.57 (d, J=1 Hz, 3H); MS (EI): 346 (90%, MI), 304 (100%); Anal. Calc. for C22H18O2S: C, 76.27; H, 5.34; N, 0.00. Found: C, 75.88; H, 5.04; N, 0.28.

EXAMPLE 7

Acetic Acid 4-(9-bromo-2,3-dimethyl-naphtho[2,3-b]thiophen-4-yl)-phenyl ester

A solution of bromine (0.326 mL, 6.15 mmol) in dichloromethane (9 mL) was added dropwise over a 15 minute period to a solution that was stirred in the absence of light of acetic acid 4-(2,3-dimethyl-naphtho[2,3-b]thiophen-4-yl)-phenyl ester (1.87 g, 5.41 mmol) and iron (III) chloride (50 mg, 0.31 mmol) in dichloromethane (47 mL) at −78° C. under a dry nitrogen atmosphere. After 10 minutes, a dilute aqueous sodium bisulfite solution was added and the reaction mixture was partitioned between water and ether. The ether phase was washed with brine and concentrated to provide the title compound as a white solid (2.09 g, 91%): mp: 190–191° C.; NMR (DMSO-d6); δ8.20 (d, J=8 Hz, 1H), 7.65 (ddd, J=8, 7, 1, 1H), 7.49 (ddd, J=8, 7, 1 Hz, 1H), 7.43–7.38 (m, 1H), 7.40 (d, J=9 Hz, 2H), 7.30 (d, J=9 Hz, 2H), 2.43 (d, J=1 Hz, 3H), 2.33 (s, 3H), 1.55 (d, J=1 Hz, 3H); MS (EI): 1 bromine isotope pattern 424 (95%, MI), 426 (100%); Anal. Calc. for C22H17BrO2S: C, 62.12; H, 4.03; N, 0.00. Found: C, 62.46; H, 4.05; N, 0.09.

EXAMPLE 8

4-(9-Bromo-2,3-dimethyl-naphtho[2,3-b]thiophen-4yl)-phenol

Aqueous potassium hydroxide (6.0 mL, 6.0 mmol) was added to a stirred, room temperature solution of acetic acid 4-(9-bromo-2,3-dimethyl-naphtho[2,3-b]thiophen-4-yl)-phenyl ester (0.48 g, 1.14 mmol) in THF (15 mL)/methanol (10 mL). After 1 h, the organic solvents were removed, water was added, the reaction mixture was acidified with 10% HCl and the resulting solid was washed with water and triturated with pet. ether and then dried in vacuo to provide the title compound as a white solid (0.32 g, 73%): mp: 165–168° C.; NMR (DMSO-d6); δ9.68 (s, 1H), 8.17 (d, J=8 Hz, 1H), 7.62 (ddd, J=8, 6, 1 Hz, 1H), 7.50 (d, J=8 Hz, 1H), 7.44 (ddd, J=8, 7, 1 Hz, 1H), 7.13 (d, J=9 Hz, 2H), 6.91 (d, J=9 Hz, 2H), 2.42 (d, J=1 Hz, 3H), 1.59 (d, J=1 Hz, 3H); MS (EI): 1 bromine isotope pattern 382 (95%, MI), 384 (100%); Anal. Calc. for C20H15BrOS: C, 62.67; H, 3.95; N, 0.00. Found: C, 62.40; H, 3.91; N, 0.09.

EXAMPLE 9

2,6-Dibromo-4-(9-bromo-2,3-dimethyl-naphtho[2,3-b]thiophen-4-yl)-phenol

A solution of bromine (0.34 mL, 5,74 mmol) in acetic acid (5 mL) was added dropwise to a room temperature, stirred solution of 4-(9-bromo-2,3-dimethyl-naphtho[2,3-b]thiophen-4-yl)-phenol (1.10 g, 2.87 mmol), potassium acetate (2.82 g, 28.7 mol) and acetic acid (31 mL). After 1.5 h, water (200 mL) and a small amount of solid sodium sulfite were added. The suspension was filtered and the solid was washed with water, triturated with pet. ether and dried in vacou to provide the title compound as a white solid (1.52 g, 88%): mp 172–174° C.: NMR (DMSO-d6); 11.95 (broad s, 1H), 10.20 (broad s, 1H), 8.19 (ddd, J=8,1,1 Hz, 1H), 7.65 (ddd, J=8, 6, 1 Hz, 1H), 7.59(s, 2H), 7.51–7.49 (m, 2H), 2.44 (d, J=1 Hz, 3H), 1.90 (s, 3H), 1.64 (d,J=1 Hz, 3H); MS (+FAB): 3 bromine isotope pattern 538 (40%), 540 (100%), 542 (90%), 544 (50%); Anal. Calc. for C22H13Br3OS.C2H4O2: C, 43.95; H, 2.85; N, 0.00. Found: C, 44.13; H, 2.66; N, 0.12.

EXAMPLE 10

Methanesulfonic acid 4-(2,3-dimethyl-naphtho[2,3-b]thiophen-4-yl)-phenyl ester

To a cold (ice bath) solution of 4-(2,3-dimethyl-naphtho[2,3-b]thiophen-4-yl-phenol (3.00 g, 9.86 mmol) and pyridine (4.0 mL, 49.3 mmol, 5 eq) in methylene chloride (24 mL) was added methylsulfonylchloride (1.14 mL, 14.8 mmol, 1.5 eq) dropwise. The bath was removed and after stirring at ambient temperature for about 38 hours the reaction mixture was combined with water (150 mL), acidified with 10% hydrochloric acid and extracted with ether. The extracts were combined and washed with brine. Silica gel was added and the solvents were removed. The adosrbate was flash chromatographed (45/55 petroleum ether/ethyl acetate) to give the title compound as a white solid (30.2 g, 80%): NMR (CDCl3); δ8.30 (s, 1H), 7.90 (d, J=8 Hz, 1H), 7.50–7.40 (m, 5H), 7.38–7.28 (m, 1H), 3.26 (s, 3H), 2.50 (s, 3H), 1.61 (s, 3H).

EXAMPLE 11

Methanesuifonic acid 4-(9-iodo-2,3-dimethyl-naphtho[2,3-b]thiophen-4-yl)-phenyl ester To a solution of methanesulfonic acid 4-(2,3-dimethyl-naphtho[2,3-b]thiophen-4-yl)-phenyl ester (3.00 g, 7.84 mmol), in tetrahydrofuran (31.5 mL), 80% aqueous acetic acid (16 mL) and concentrated sulfuric acid (0.87 mL) was added iodine (1.59 g, 6.27 mmol, 0.8 eq) and iodic acid (0.414 g, 2.35 mmol, 0.9 eq) at room temperature. The mixture was stirred at room temperature for 12 days. The reaction mixture was poured into a dilute aqueous solution of sodium bisulfite (200 mL) and the organics were extracted with ether (2×200 mL). The extracts were combined and silica gel was added. The solvents were removed and the adsorbate was flash chromatographed (90/10 petroleum ether/ethyl acetate) without achieving purification. The recovered material was purified by high pressure liquid chromatography which gave recovered starting material (30.5%) and gave the title compound as a white solid (0.835 g, 30%): mp 212–213° C.; NMR (DMSO-d6); δ8.09 (d, J=8 Hz, 1H), 7.64–7.58 (m, 1H), 7.54–7.42 (m, 5H), 7.43 (d, J=8 Hz, 1H), 3.47 (s, 3H, SO3CH3), 2.42 (s, 3H), 1.50 (s, 3); MS(EI): [M+] 508 (100%); Anal. calc. for C21H17IO3S2, C, 49.61; H, 3.37; N, 0.00. Found: C, 49.44; H, 3.52; N, 0.03.

EXAMPLE 12

4-(2,3-Dimethyl-9-phenylsulfanyl-naphtho[2,3-b]thiophen-4-yl)-phenol

To a stirred suspension of methanesulfonic acid 4-(9-iodo-2,3-dimethyl-naphtho[2,3-b]thiophen-4-yl)-phenyl ester (0.620 g, 1.22 mmol), and copper I oxide (0.192 g, 1.34 mmol) in anhydrous N,N-dimethylformamide (10 mL) was added thiophenol (0.270 mL, 2.68 mmol) and finely ground sodium hydroxide (0.107 g, 2.68 mmol) under a dry argon atmosphere. The vessel was sealed and heated at 155° C. for 9.5 hours. After stirring at ambient temperature for about 8 hours the reaction mixture was poured into water, acidified with hydrochloric acid and the organics were extracted into ether. The extracts were combined, filtered, washed with water and concentrated. The yellow solid residue was dissolved in dioxane (8 mL) and a 2.5 N soduim hydroxide solution (4.5 mL) was added. The vial was sealed and heated at 102° C. When the reaction was done (as indicated by thin layer chromatography) the mixture was cooled to room temperature, diluted with water, and acidified with hydrochloric acid. The organics were extracted with ether, combined with silica gel and the solvents were removed. The adsorbate was flash chromatographed (gradient 90/10–85/15 petroleum ether/ethyl acetate) and the solvents were chased with benzene and petroleum ether to give the title compound as a white solid (0.426 g, 85%): NMR (DMSO-d6); δ9.70 (s, 1H, OH), 8.40 (d, J=8 Hz, 1H), 7.56–7.51 (m, 2H), 7.44–7.40 (m, 1H), 7.25–7.12 (m, 5H), 7.02 (d, J=7 Hz, 2H), 6.93 (d, J=9 Hz, 2H), 3.67 (s, 3H), 1.62 (s, 3H); MS(EI): [M+] 412 (100%); Anal. calc. for C26H20OS2: C, 75.69; H, 4.89; N, 0.00. Found C, 74.98; H, 4.86; N, 0.13.

EXAMPLE 13

2,6-Dibromo-4-(2,3-dimethyl-9-phenylsulfanyl-naphtho[2,3-b]thiophen-4-yl)-phenol To a suspension of 4-(2,3-dimethyl-9-phenylsulfanyl-naphtho[2,3-b]thiophen-4-yl)-phenol (0.414 g, 1.00 mmol), and potassium acetate (0.982 g, 10.0 mmol) in glacial acetic acid (24 mL) was added a solution of bromine (0.114 mL, 2.21 mmol) in glacial acetic acid (2.50 mL) dropwise over a period of 10 minutes at room temperature. Complete dessolution occurred followed by the appearance of a precipitate. After stirring for 2 hours the reaction was quenched with dilute aqueous sodium bisulfite, added to water (100 mL), acidified with 10% hydrochloric acid and extracted with ether. The extracts were washed with water, the layers separated and after standing overnight combined with silica gel and the solvents were removed. The adsorbate was flash chromatographed (90/10 petroleum ether/ethyl acetate) to give the title compound as an off-white solid (0.391 g, 58%): NMR (DMSO-d6); δ10.25 (s, 1H, OH), 8.42 (d, J=8 Hz, 1H), 7.65 (s, 2H), 7.60–7.47 (m, 3H), 7.247.19 (m, 3H), 7.15–7.00 (m,2H), 2.39 (s, 3H), 1.62 (s, 3H).

EXAMPLE 14

Acetic acid 4-(9-bromo-2-chloromethyl-3-methyl-naphtho[2,3-b]thiophen-4-yl)-phenyl ester To a cold (ice bath) solution of acetic acid 4-(9-bromo-2,3-dimethyl-naphtho[2,3-b]thiophen-4-yl)-phenyl ester (4.00 g, 9.4 mmol) in anhydrous methylene chloride (41 mL) was added sulfuryl chloride (0.76 mL, 10.3 mmol) dropwise over a period of 10 minutes. After stirring 1 hour in the ice bath the reaction was quenched with water (100 mL) and diluted with diethyl ether. After filtering, the layers were separated. Silica gel was added to the organic layer and the solvents were removed. The adsorbate was flash chromatographed (gradient 90/10–80/20 petroleum ether/ethyl acetate) to give the title compound as a white solid (2.57 g, 59%): NMR (DMSO-d6); δ8.23 (d, J=8 Hz, 1H), 7.71 (dd, J=8,1 Hz, 1H), 7.55–7.43 (m, 4H), 7.33–7.30 (m, 2H), 5.09 (s, 2H), 2.34 (s, 3H), 1.66 (s, 3H).

EXAMPLE 15

4-(9-Bromo-3-methyl-2-morpholin-4-yl)methyl-naphtho[2,3-b]thiophen-4-yl)-phenol

To a solution of acetic acid 4-(9-bromo-2-chloromethyl-3-methyl-naphtho[2,3-b]thiophen-4-yl)-phenyl ester (1.20 g, 2.61 mmol) in anhydrous N,N-dimethylformamide (12 mL) was added potassium carbonate (1.08 g, 7.83 mmol, 3 eq) and morpholine (0.683 mL, 7.83 mmol, 3 eq) at room temperature under a dry nitrogen atmosphere. After stirring 1.75 hours another equivalent of morpholine (0.227 mL) was added and after an additional 0.5 hours another 2 equivalents of morpholine (0.50 mL) were added. After stirring 1 hour longer the reaction mixture was diluted with water (125 mL) and the organics were extracted with diethyl ether (400 mL). The layers were separated and silica gel was added to the organic phase. The solvents were removed and the adsorbate was flash chromatographed (gradient 75/25–70/30 petroleum ether/ethyl acetate) to the title compound as an white solid (1.00 g, 82%): mp 250–251° C.; NMR (DMSO-d6); δ9.69 (s, 1H), 8.18 (d, J=8 Hz, 1H), 7.63 (ddd, J=8,7,1 Hz, 1H), 7.51–7.42 (m, 2H), 7.13 (d, J=8 Hz, 2H), 6.91 (d, J=8 Hz, 2H), 3.71 (s, 2H), 3.60 (t, J=5 Hz, 4H), 2.50–2.48 (m, 4H), 1.65 (s, 3H); MS (EI): [M+], 1 bromine isotope pattern, 467 (10%), 469 (10%); Anal. Calc for C24H22BrNO2S: C, 61.53; H, 4.73; N, 2.99. Found: C, 61.53; H, 4.88; N, 3.01.

EXAMPLE 16

4-(9-Bromo-2-diethylaminomethyl-3-methyl-naphtho[2,3-b]thiophen-4-yl)-acetate

To a suspension of 4-(9-bromo-2-chloromethyl-3-methyl-naphtho[2,3-b]thiophen-4-yl)-acetate (1.27 g, 2.76 mmol) and potassium carbonate (1.146 g, 8.29 mmol) in anhydrous N,N-dimethylformamide (15 mL) was added dimethylamine (0.86 mL, 8.29 mmol) at room temperature under a dry nitrogen atmosphere. After stirring 3 hours additional dimethylamine (0.50 mL, 4.83 mmol) was added and the reaction mixture was stirred at room temperature for 3 hours before storing in the cold (−14° C.) overnight. After stirring an additional 5 hours at room temperature the reaction mixture was diluted with water (100 mL). The organics were extracted with ether. The extracts were combined ,silica gel was added and the solvent was removed The adsorbate was flash chromatographed (gradient 85/15–80/20 petroleum ether/ethyl acetate) to give the title compound as a yellow solid (0.332 g, 26%): NMR (CHCl3); δ8.29 (d, J=8 Hz, 1H), 7.54–7.51 (m, 2H), 7.36–7.30 (m, 1H), 7.20 (d, J=8 Hz, 2H), 6.96 (m, 2H), 3.90–3.65 (broad s, 2H), 2.80–2.45 (broad s, 4H), 1.69 (s, 3H), 1.26–1.00 (broad s, 6H); MS (EI): M+ M/Z 453 one bromine present, 301 (58%), 302 (16%), 303 (7%), 382 (100%), 383 (54%), 384 (14%), 453 (30%), 455 (30%); MS [(+)ESI]: [M+H]=496(65%), 1 bromine isotope pattern; High Resolution MS: Calc. Sample Mass: 496.09459 for Formula C25H31N3O3Cl [M+H], Measured Mass: 496.09407, Mass deviation: 0.52 mmu; Anal. Calc. for C24H24BrNOS: C, 63.43; H, 5.32; N, 3.08. Found: C, 62.33; H, 5.11; N, 2.75.

EXAMPLE 17

4-(9-Bromo-2-diethylaminomethyl-3-methyl-naphtho[2,3-b]thiophen-4-yl)-phenol

To a solution of 4-(9-bromo-2-diethylaminomethyl-3-methyl-naphtho[2,3-b]thiophen-4-yl)-acetate (0.676 g, 1.36 mmol), in tetrahydrofuran (18 mL) and methanol (12 mL) was added an aqueous solution of potassium hydroxide (1 N, 1.63 mL) dropwise at room temperature. After stirring 1 hour the solvents were removed. The residue was combined with water (50 mL) and acidified with 10% hydrochloric acid. The organic impurities were extracted with ether leaving a white solid at the biphase interface. The sticky solid was filtered, triturated with acetic acid and concentrated. This salt of the title compound was dissolved in tetrahydrofuran and methanol and combined with saturated aqueous sodium bicarbonate. After stirring 20 minutes the mixture was diluted with water and stirred 10 minutes longer. The organics were extracted with ether. The ether layer was washed with brine and concentrated to give the title compound as a yellow solid (0.490 g, 79%): NMR (DMSO-d6); δ9.69 (s, 1H, OH), 8.18 (d, J=8 Hz, 1H), 7.63–7.59 (m, 1H), 7.51–7.43 (m, 2H), 7.14 (d, J=8 Hz, 2H), 6.91 (d, J=8 Hz, 2H), 3.73 (s, 2H), 2.58–2.50 (m, 4H), 1.63 (s, 3H), 1.01 (t, J=7 Hz, 6H).

EXAMPLE 18

2,6-Dibromo-4-(9-bromo-2-diethylaminomethyl-3-methyl-naphtho[2,3-b]thiophen-4-yl)-phenol To a solution of 4-(9-bromo-2-diethylaminomethyl-3-methyl-naphtho[2,3-b]thiophen-4-yl)-phenol (0.462 g, 1.07 mmol), in 9/1 glacial acetic acid/water (10 mL) was added a solution of bromine (0.115 mL, 2.24 mmol, 2.2 eq) in 9/1 acetic acid/water (4 mL). After stirring 1.5 hours the reaction mixture was quenched with dilute aqueous sodium bisulfite, diluted further with water and the organics were extracted with ether. An insoluble solid was decanted into a flask and stirred overnight in ether. The ether was removed and the solid (0.162 g, 0.265 mmol) was dissolved in tetrahydrofuran (100 mL) and a 1 N aqueous solution of sodium hydroxide (0.265 mL, 0.265 mmol) was added dropwise. After stirring 20 minutes the solvent was removed and the residue was stirred in water (100 mL). The water was removed by decantation and the residue was stirred in petroleum ether overnight. The solvent was removed. The residue was dissolved in tetrahydrofuran/ether and silica gel was added. The solvents were removed and the adsorbate was flash chromatographed (75/25 petroleum ether/ethyl acetate) to give the desired compound as a white solid (0.113 g, 17%): (DMSO-d6); δ10.3–10.1 (broad s, 1H, OH), 8.20

(d, J=8 Hz, 1H), 7.66–7.63 (m, 1H), 7.60 (s, 2H), 7.50–7.48 (m, 2H), 3.76 (s, 2H), 3.28–2.60 (m, 4H), 1.02 (t, J=7 Hz, 6H); MS+FAB: M+@ M/Z 609/611/613/615 3 bromine pattern 536 (22%), 538 (68%), 540 (80%), 541 (52%), 611 (22%), 613 (22%); Anal. Calc. for C24H22Br3NOS: C, 47.08; H, 3.62; N, 2.29. Found: C, 47.21; H, 3.69; N, 2.21.

EXAMPLE 19

2,6-Dibromo-4-(9-bromo-3-methyl-2-morpholin-4ylmethyl-naphtho[2,3-b]thiophen-4-yl)-phenol To a solution of 4-(9-bromo-3-methyl-2-morpholin-4-ylmethyl-naphtho[2,3-b]thiophen-4-yl)-phenol (0.854 g, 1.82 mmol) in 9/1 acetic acid/water (17 mL) was added a solution of bromine (0.207 mL, 4.01 mmol) in 9/1 acetic acid/water (1 mL). After stirring 3 hours the reaction was diluted with water (200 mL) and the organics were extracted several times with diethyl ether. The extracts were combined, concentrated and chased with benzene to give a quantitative yield of the title compound as a yellow solid (1.18 g): mp 237–240° C.; NMR (pyridine-d5); δ8.43 (dd, J=8,1 Hz, 1H), 7.81 (s, 2H), 7.71 (d, J=8 Hz, 1H), 7.62 (m, 1H), 7.50 (m, 1H), 6.20–5.30 (broad s, 1H), 3.78 (t, J=5 Hz, 4H), 3.70 (s, 2H), 2.55 (t, J=4 Hz, 4H), 1.78 (s, 3H); MS (EI): [M+], 3 Bromine isotope pattern, 622 (8%), 624 (18%), 626 (19%), 628 (8%); Anal. Calc. for C24H20Br3NO2S: C, 46.03; H, 3.22; N, 2.24. Found: C, 45.07; H, 3.31; N, 2.05.

EXAMPLE 20

4-(9-Bromo-2,3-dimethyl-naphtho[2,3-b]thiophen-4-yl)-2-nitro-phenol

Ethanol (40 mL) was added to a mixture of 4-(9-bromo-2,3-dimethyl-naphtho[2,3-b]thiophen-4-yl)-phenol (1.98 g, 5.17 mmol) and iron nitrate heptahydrate (2.09 g, 5.17 mmol) and the resultant dark blue solution was heated in a 45 ° C. oil bath for 14 h. The reaction mixture was added to dilute HCl and extracted with ether. Silica gel was added to the ether phase and the solvent was removed. The adsorbate was flashed (95:5 petroleum ether: ethyl acetate) to provide the title compound as an orange solid (1.63 g, 74%): mp 183–185° C.: NMR (DMSO-d6); δ11.31 (s, 1H), 8.21 (d, J=8 Hz, 1H), 7.85 (d, J=2 Hz, 1 H), 7.66 (ddd, J=8, 6, 1 Hz, 1H), 7.54 (dd, J=8, 2 Hz, 1H), 7.48 (dd, J=7, 1 Hz, 1H), 7.29 (d, J=8 Hz, 1H), 6.91 (d, J=9 Hz, 2H), 2.44 (d, J=1 Hz, 3H), 1.61 (d, J=1 Hz, 3H); MS (EI): 1 bromine isotope pattern 427 (95%, MI), 429 (100%); Anal. Calc. for C20H14BrNO3S: C, 56.09; H, 3.29; N, 3.27. Found: C, 55.55; H, 3.15; N, 3.23.

EXAMPLE 21

2-Bromo-4-(9-bromo-2,3-dimethyl-naphtho[2,3-b] thiophen-4-yl)-6-nitro-phenol

A solution of bromine (0.040 mL, 0.756 mmol) in acetic acid (0.5 mL) was added dropwise to a stirred suspension of 4-(9-bromo-2,3-dimethyl-naphtho[2,3-b]thiophen-4-yl)-2-nitro-phenol (0.20 g, 0.467 mmol), potassium acetate (0.228 g, 2.335 mmol) in acetic acid (4 mL). After 10 min, water was added and the reaction mixture was extracted with ether. Silica gel was added to the ether phase and the solvent was removed. The adsorbate was flashed (gradient: 95:5 to 85:15) to provide the title compound as a yellow solid (0.141 g, 60%): mp 129–130° C.: NMR (DMSO-d6); δ11.30 (s, 1H), 8.22 (d, J=8 Hz, 1H), 8.03 (s, 1H), 7.96 (s, 1H), 7.67 (quintuplet, J=4 Hz, 1H), 7.51 (d, J=4 Hz, 2H), 2.45 (s, 3H), 1.65 (s, 3H); MS (EI): 2 bromine isotope pattern 505 (40%), 507 (100%), 509 (50%); Anal. Calc. for C20H13Br2NO3S: C, 47.36; H, 2.58; N, 2.76. Found: C, 47.18; H, 2.55; N, 2.63.

EXAMPLE 22

2-Amino-4-(9-bromo-2,3-dimethyl-naphtho[2,3-b] thiophen-4-yl)-phenol

Using a procedure similar to Tet. Lett. 1990, 1181–1182, Montmorillinite K10 clay (425 mg) was added to a solution of 4-(9-bromo-2,3-dimethyl-naphtho[2,3-b]thiophen-4-yl)-2-nitro-phenol (0.608 g, 1.42 mmol), anhydrous hydrazine (0.276 mL, 8.95 mmol) and ethanol (4.2 mL) and the suspension was heated at 85° C. for 30 min. The reaction mixture was cooled to room temperature, added to water and extracted with ether. The ether was dried and concentrated to provide the title compound as a white solid (0.576 g, 100%): mp 173–175° C.: NMR (DMSO-d6); δ9.26 (s, 1H), 8.14 (dd, J=8, 1 Hz, 1H), 7.63–7.58 (m, 2 H), 7.42 (ddd, J=8, 6, 1 Hz, 1H), 6.78 (d, J=8 Hz, 1H), 6.54 (d, J=2 Hz, 1H), 6.35 (dd, J=8, 2 Hz, 1H), 4.67 (broad s, 2H), 2.42 (s, 3H), 1.69 (s, 3H); MS (+FAB): 1 bromine isotope pattern 398 (30%, M+H), 400 (30%, M+H); Anal. Calc. for C20H16BrNOS: C, 60.31; H, 4.05; N, 3.52; Found: C, 61.36; H, 4.08; N, 3.25.

EXAMPLE 23

2-Amino-6-bromo-4-(9-bromo-2,3-dimethylnaphtho[2,3-b]thiophen-4-yl)-phenol

Using a procedure similar to Tet. Lett. 1990, 1181–1182, Montmorillinite K10 clay (1.4 g) was added to a solution of 2-bromo-4-(9-bromo-2,3-dimethyl-naphtho[2,3-b]thiophen-4-yl)-2-nitro-phenol (1.2 g, 2.37 mmol), anhydrous hydrazine (1 mL) and ethanol (7.2 mL) and the suspension was heated at 85° C. for 1 h. The reaction mixture was cooled to room temperature and concentrated. The residue was twice flash chromatographed (first time, eluent: ether, second time, eluent: 4:1 petrolerum ether ethyl acetate) to provide the title compound as a white solid (0.741 g, 66%): NMR (DMSO-d6); δ8.16 (ddd, J=8, 1, 1 Hz, 1H), 7.65–7.60 (m, 2 H), 7.47 (ddd, J=8, 6, 1 Hz, 1H), 6.65 (d, J=2 Hz, 1H), 6.57 (d, J=2 Hz, 1H), 2.43 (d, J=1 Hz, 3H), 1.73 (d, J=1 Hz, 3H); MS (EI): 2 bromine isotope pattern 475 (50%, M+H), 477 (100%, M+H), 479 (50%, M+H); Anal. Calc. for C20H15Br2NOS: C, 50.34; H, 3.17; N, 2.94. Found: C, 51.35; H, 3.35; N, 2.72.

EXAMPLE 24

[2-Bromo-4-(9-bromo-2,3-dimethyl-naphtho[2,3-b] thiophen-4-yl)-2-nitro-phenoxy]-acetic acid Methyl bromoacetate (0.150 mL, 1.58 mmol) was added to a stirred suspension of potassium carbonate (0.223 g, 1.61 mmol), 2-bromo-4-(9-bromo-2,3-dimethyl-naphtho[2,3-b] thiophen-4-yl)-2-nitro-phenol (0.400 g, 0.789 mmol) in DMF (2.8 mL). After 15 h, the reaction mixture was added to water and extracted with ethyl acetate. Silica gel was added to the ethyl acetate and the solvent was removed. The adsorbate was flashed (9:1 petroleum ether: ethyl actetate) to provide the title compound as a yellow solid (0.305 g, 67%). This solid (0.050 g, 0.086 mmol) was dissolved in 1:1 THF:methanol (2 mL) and treated with aqueous potassium hydroxide (1.0 N, 0.30 mL, 0.30 mmol). After 25 min the reaction mixture was diluted with water, acidified with 10% aqeous HCl and extracted with ether. The ether phase was dried (sodium sulfate), concentrated and recrystallized from petroleum ether:ether to provide the title compound as a white solid (0.025 g, 51%): mp 228–229° C.: NMR (DMSO-d6); δ8.23 (d, J=9 Hz, 1H), 8.14 (d, J=2 Hz, 1H), 8.04 (d, J=2 Hz, 1H), 7.69 (ddd, J=8, 7, 1, 1H), 7.54 (ddd, J=8, 7, 1 Hz, 1H), 7.48 (d, J=8 Hz, 1H), 4.87 (d, J=6 Hz, 1H), 4.82 (d, J=6 Hz, 1H), 2.46 (s, 3H), 1.62 (s, 3H); MS (+FAB): 2 bromine isotope pattern 563 (40%), 565 (100%), 567 (50%); Anal.

Calc. for C22H15Br2NO5S: C, 46.75, H, 2.68; N, 2.48. Found: C, 45.18; H, 2.66; N, 2.38.

EXAMPLE 25

(S)-2-Hydroxy-3-phenylpropionic acid, methyl ester

A solution of commercially available (S)-2-hydroxy-3-phenylpropionic acid (5.0 g, 30.1 mmol) and p-toluenesulfonic acid hydrate (1 g) in methanol (125 mL) was refluxed with removal of water using 3A molecular sieves for 17 h. The solution was concentrated and dissolved in ether. The ether solution was washed with saturated sodium bicarbonate, brine and concentrated to provide the title compound as a white solid (5.32 g, 98%): NMR (CDCl3); δ7.36–7.20 (m, 5H), 4.47 (ddd, J=5, 6, 7 Hz, 1H), 3.78 (s, 3H), 3.14 (dd, J=5, 14 Hz, 1H), 2.97 (dd, J=7, 14 Hz), 2.69 (d, J=6 Hz, 1H).

EXAMPLE 26

(S)-2-[4-Nitrobenzoyl]-4-phenylbutyric acid, ethyl ester

To a cold (ice bath) solution of commercially available (R)-2-hydroxy4-phenyl-butyrate, ethyl ester (1.86mL, 9.60 mmole), p-nitrobenzoic acid (6.42 g, 38.4mmole, 4 eq) and triphenylphosphine (10.07 g, 38.4 mmole, 4 eq.) in anhydrous tetrahydrofuran (110 mL) was added diethyl azodicarboxylate (6.05 mL, 38.4 mmole, 4 eq) dropwise over a period of 40 minutes keeping the internal temperature between 4 and 5° C. After stirring for one additional hour at 4–5° C., the ice bath was removed and the solution was allowed to stir at ambient temperature for 5 days. The solvents were removed and the residue was redissolved in a mixture of ether and ethyl acetate (600 mL). Silica gel (200 mL) was added and the solvents removed. The adsorbate was flash chromatographed (gradient (80/20–70/30 petroleum ether/ethyl acetate) to give the title compound as a yellow oil (4.03 g): NMR (CDCl3); δ8.30 (d, J=9 Hz, 2H), 8.18 (d, J=9 Hz, 2H), 7.38–7.18(m, 5H), 5.28 (t, J=2 Hz, 1H), 4.23(q, J=7 Hz, 2H), 2.85 (t, J=8 Hz, 2H), 2.40–2.33 (m, 2H), 1.29 (t, J=7H, 3H); MS [(+) FAB]: [M+H] m/z= 358.

EXAMPLE 27

(S)-2-Hydroxy-4-phenylbutyric Acid, ethyl ester

To a suspension of potassium cyanide (0. 176 g, 2.70 mmole) in absolute ethanol (43 mL) was added a solution of (S)-2-[4-nitrobenzoyl]-4-phenylbutyric acid, ethyl ester (3.86 g, 10.8 mmole) in absolute ethanol (38 mL) dropwise over a period of 0.5 hours. After stirring 2.25 hours the solvent was removed and the reside was diluted with water and acidified with dilute hydrochloric acid. The organics were extracted with ether. The extracts were combined, silica gel (60 mL) was added and the solvent was removed. The adsorbate was flash chromatographed, eluent (gradient 90/10–80/20 petroleum ether/ethyl acetate) and the solvents were chased with benzene to give the title compound as a yellow oil (1.67 g, 74%): NMR (CDCl3); δ7.38–7.16 (m, 5H), 4.30–4.10(m, 3H), 2.9–2.6 (m, 3H,), 2.2–1.9(m, 2H), 1.15(t, 4 Hz, 3H); [a]25D +178.23 at 10.98 mg/mL CHCl3.

EXAMPLE 28

(R)-2-[2,6-Dibromo-4-(9-bromo-2,3-dimethyl-naphtho[2,3-b]thiophen-4-yl)-phenoxy]3-phenyl-propionic acid methyl ester Diethylazodicarboxylate (0.262 mL, 1.67 mmol) was added dropwise to a stirred, room temperature solution of 2,6dibromo-4-(9-bromo-2,3-dimethyl-naphtho[2,3-b]thiophen-4-yl)-phenol (0.60 g, 1.11 mmol), and (S)-2-hydroxy-3-phenylpropionic acid, methyl ester (0.300 g, 1.67 mmol), triphenylphosphine (0.437 g, 1.67 mmol) and benzene (5 mL) and the solution was heated in an 80° C. oil bath for 6 h. Upon cooling to room temperature, the reaction mixture was diluted with ether and silica gel (30 mL) was added. The reaction mixture was concentrated and the silica adsorbate was flash chromatographed (95:5 petroleum ether-:ethyl acetate) to provide the title compound as a white solid (0.76 g, 97%): mp 174–175° C.: NMR (DMSO-d6); δ8.21 (ddd, J=8,1,1 Hz, 1H), 7.74 (d, J=2 Hz, 1H), 7.73 (d, J=2 Hz, 1H),7.67 (ddd, J=8, 6, 1 Hz, 1H), 7.53 (ddd, J=8, 7, 1 Hz, 1H), 7,43 (d, J=8 Hz, 1H), 7.35–7.24 (m, 5H), 5.11 (dd, J=7, 6 Hz, 1H), 3.61 (s, 3H), 3.43 (dd, 13, 6 Hz, 1H), 3.40 (dd, 13, 7 Hz, 1H), 2.44 (d, J=1 Hz, 3H), 1.60 (d, J=1 Hz, 3H); MS (+FAB): 3 bromine isotope pattern 700(20%), 702 (70%), 704 (75%), 706 (25%); Anal. Calc. for C30H23Br3O3S: C, 51.23; H, 3.30; N, 0.00. Found: C, 51.52; H, 3.36; N, 0.12.

EXAMPLE 29

(R)-2-[2,6-Dibromo-4-(9-bromo-2,3-dimethyl-naphtho[2,3-b]thiophen-4-yl)-phenoxy]3-phenyl-propionic acid Aqueous potassium hydroxide (1 N, 2.00 mL, 2.00 mmol) was added to a stirred solution of (R)-2-[2,6-dibromo-4-(9-bromo-2,3-dimethyl-naphtho[2,3-b]thiophen-4-yl)-phenoxy]3-phenyl-propionic acid methyl ester (0.699 g, 0.99 mmol) in THF (12 mL)/methanol (7 mL). After 3 h the solution was concentrated, diluted with water (100 mL) and acidified with 10% aqueous HCl. The solid was filtered, washed with water and triturated with petroleum ether and dried in vacuo to provide the title compound as a white solid (0.645 g, 94%): [a]D25=+14.29° (8.75 mg/mL CHCl3); NMR (DMSO-d6); δ8.19 (d, J=8 Hz, 1H), 7.66 (ddd, J=8, 7, 1 Hz, 1H), 7.61 (s, 2H), 7.52 (ddd, J=8, 7, 1 Hz, 1H), 7.41 (d, J=8 Hz, 1H), 7.38–7.20 (m, 5H), 5.27 (t, J=7 Hz, 1H), 3.37 (dd, 14, 6 Hz, 1H), 3.28 (dd, 14, 7 Hz, 1H), 2.43 (s, 3H), 1.59 (s,3H); MS (+FAB): 3 bromine isotope pattern 686 (20%), 688 (75%), 690 (75%), 692 (25%); Anal. Calc. for C29H21Br3O3S: C, 50,53; H, 3.07; N, 0.00. Found: C, 50.04; H, 3.11; N, 0.05.

EXAMPLE 30

(R)-2-[2,6-Dibromo-4-(9-bromo-2,3-dimethylnaptho[2,3-b]thien-4-yl)-phenoxy]-propanoic acid To a solution of 2,6-dibromo-4-(9-bromo-2,3-dimethylnaptho[2,3-b]thien-4-yl)-phenol (0.300 g, 0.554 mmol), commercially available methyl (S)-(−)-lactate (0.079 mL, 0.831 mmol) and triphenylphosphine (0.218 g, 0.831 mmol) in dry benzene (5 mL) was added diethyl azodicarboxylate (0.131 mL, 0.831 mmol) dropwise at room temperature over a period of 10 minutes under a dry nitrogen atmosphere. The reaction mixture was heated at reflux for 4 hours and remained stirring at ambient temperature for 24 hours. The reaction mixture was diluted with diethyl ether and combined with silica gel. The solvents were removed and the adsorbate was flash chromatographed (75/25 petroleum ether/methylene chloride) to provide a white solid (0.283 g, 81%). To a solution of this solid (0.260 g, 0.415 mmol) in tetrahydrofuran (9 mL) and methanol (3 mL) was added an aqueous solution of potassium hydroxide (1N, 0.498 mL, 0.498 mmol) dropwise at room temperature. After stirring 1.5 hours the solvents were removed. The residue was combined with water and acidified with 10% aqueous hydrochloric acid. Diethyl ether was added and after stirring 10 minutes the two phases were shaken well and separated.

The organic phase was washed with brine, concentrated, and chased with petroleum ether to give title compound as a white solid (0.257 g, 99%): mp 224–225° C.; NMR (DMSO-d6); δ13.09–13.06 (broad s, 1H, COOH), 8.20 (d, J=8 Hz, 1H), 7.75 (s, 2H), 7.67 (ddd, J=8, 7, 1 Hz, 1H), 7.55–7.47 (m, 2H), 5.02 (q, J=7 Hz, 1H), 2.44 (s, 3H), 1.62 (s, 3H,), 1.56 (d, J=6 Hz, 3H); MS (+FAB): [M+], 3 bromine isotope pattern, 609.7 (30%), 611.8 (75%), 613.8 (100%), 615.7 (35%); High resolution MS[(FAB)+ve] Calc Sample mass for C23H17Br3O3S: 609.84485, measured mass 609.85789, mass deviation 13.04 mmu. Anal. Calc. for C23H17Br3O3S: C, 45.05; H, 2.79; N, 0.00. Found: C, 44.30; H, 2.69; N, 0.38.

EXAMPLE 31

(S)-2-[2,6-Dibromo-4-(9-bromo-2,3-dimethyl-naphtho[2,3-b]thiophen-4-yl)-phenoxy]-4-phenyl-butyric acid Prepared from 2,6-dibromo-4-(9-bromo-2,3-dimethyl-naphtho[2,3-b]thiophen-4-yl)-phenol (Example 9) and commercially available (R)-2-hydroxy-4-phenyl-butyrate, ethyl ester according to the procedure of Example 30. White solid: mp 176–177° C.; [a]25/D=+7.58° (10.692 mg/mL, CHCl3); NMR (DMSO-d6); δ13.0 (broad s, 1H, COOH), 8.21 (ddd, J=8, 7, 1 Hz, 1H), 7.73 (s, 2H), 7.67 (ddd, J=8, 7, 1 Hz, 1H), 7.52 (ddd, J=8, 7, 1 Hz, 1H), 7.46 (m, 1H), 7.32–7.28 (m, 2H), 7.24–7.18 (m,3H), 5.03 (t, J=6 Hz, 1H), 2.95 (m, 1H), 2.72 (m, 1H), 2.44 (s, 3H), 2.28 (m,2H), 1.61 (s, 3H); MS (+FAB): [M+], 3 bromine isotope pattern, 700 (30%), 702 (100%), 704 (75%), 706 706(40%); Anal. Calc. for C30H23Br3O3S: C, 51.23; H3.30; N 0.00. Found: C, 51.15; H, 3.13; N, 0.00.

EXAMPLE 32

(R)-2-[2,6-Dibromo-4-(9-bromo-2,3-dimethyl-naphtho[2,3-b]thiophen-4-yl)-phenoxy]-4-phenyl-butyric acid Prepared from 2,6-dibromo-4-(9-bromo-2,3-dimethyl-naphtho[2,3-b]thiophen-4-yl)-phenol (Example 9) and (S)-2-hydroxy-4-phenyl-butyrate, ethyl ester (Example 27) according to the procedure of Example 30. White solid: [a]25/D=−12.187° (9.929 mg/mL, CHCl3); NMR (DMSO-d6); δ13.24 (s, 1H), 8.21 (d, J=8 Hz, 1H), 7.73 (s, 2H), 7.67 (ddd, J=8, 7, 1 Hz, 1H), 7.52–7.45 (m, 2H), 7.32–7.28 (m, 2H), 7.24–7.20 (m, 3H) 5.02 (d, J=6 Hz, 1H), 2.99–2.86 (m, 1H), 2.75–2.65 (m, 1H), 2.45 (s, 3H), 2.30–2.20 (m, 2H), 1.61 (s, 3H); MS (+FAB): [M+], 3 bromine isotope pattern, 700 (30%), 702 (100%), 704 (90%), 706 (55%); Anal. Calc. for C30H23Br3O3S: C, 51.23; H, 3.30; N, 0.00. Found: C, 51.33; H, 3.33; N, 0.29.

EXAMPLE 33

(R)-2-[2,6-dibromo-4-(2,3-dimethyl-9-phenylsulfanyl-naphtho[2,3-b]thiophen-4-yl-phenoxy]-3-phenyl-propionic acid Prepared from 2,6-dibromo-4-(2,3-dimethyl-9-phenylsulfanyl-naphtho[2,3-b]thiophen-4-yl)-phenol (Example 13) and (S)-2-hydroxy-3-phenylpropionic acid, methyl ester (Example 25) according to the procedure of Example 30. White solid: opt. rot. [a]25/D=+22.84° (10.068 mg/mL, CHCl3); NMR (DMSO-d6); δ13.13 (broad s, 1H), 8.42 (d, J=8 Hz, 1H), 7.75 (t, J=2 Hz, 2H), 7.58 (dd, J=8, 7, 1 Hz, 1H), 7.50 (ddd, J=8, 7, 1 Hz, 1H), 7.44 (d, J=8 Hz, 1H), 7.37–7.19 (m, 7H), 7.15–7.11 (m, 1H), 7.03–7.00 (m, 2H), 5.22 (t, J=7 Hz, 1H), 3.37–3.28 (m, 2H), 2.39 (s, 3H), 1.62 (s, 3H); MS (EI): [M+], 2 bromine isotope pattern, 716 (10%), 718 (20%), 720 (10%); Anal. Calc. for C35H26Br2O3S2: C, 58.50; H, 3.65; N, 0.00. Found: C, 58.77; H, 3.94; N, 0.16.

EXAMPLE 34

(R)-2-[2,6-Dibromo-4-(2,3-dimethyl-9-phenylsulfanyl-naphtho[2,3-b]thiophen-4-yl)-phenoxy]-propionic acid Prepared from 2,6-dibromo-4-(2,3-dimethyl-9-phenylsulfanyl-naphtho[2,3-b]thiophen-4-yl)-phenol (Example 13) and and commercially available methyl (S)-(−)-lactate according to the procedure of Example 30. White solid: mp 237–239° C.; [a]25/D=−1.99° (10.051 mg/mL, CHCl3); NMR (DMSO-d6); δ13.2 (broad s, 1H, COOH), 8.43 (d, J=8 Hz, 1H), 7.80 (s, 2H), 7.62–7.58 (m, 1H), 7.56–7.50 (m, 2H), 7.23–7.13 (m, 3H), 7.04–7.01 (m, 2H), 5.03 (quartet, J=7 Hz, 1H), 2.40 (s, 3H), 1.63 (s, 3H), 1.57 (d, J=8 Hz, 3H); MS (EI): [M+], 2 bromine isotope pattern, 640 (47%), 642 (100%), 644 (56%); Anal. calc. for C29H22Br2O3S2: C, 54.22; H, 3.45; N, 0.00. Found: C, 53.64; H, 3.33; N, 0.05.

EXAMPLE 35

2-[2,6-Dibromo-4-(9-bromo-3-methyl-2-morpholin-4-ylmethyl-naphtho[2,3-b]thiophen-4-yl)-phenoxy]-3-phenyl-propionic acid Prepared from dibromo-4-(9-bromo-3-methyl-2-morpholin-4-yl-methyl-naphtho[2,3-b]thiophen-4-yl)-phenol (Example 19) and commercially available methyl (S)-(−)-lactate according to the procedure of Example 30. Yellow solid: Opt. rot. [a]=+26.512° (10.184 mg/mL, DMSO); NMR (pyridine-d5); δ8.41 (d, J=9 Hz, 1H), 7.84 (dd, J=3, 1 Hz, 2H), 7.70 (d, J=7 Hz, 2H), 7.43–7.32 (m, 6H), 5.89 (t, J=7 Hz, 1H), 3.88 (dq, 2H), 3.77 (t, J=7 Hz, 4H), 3.66 (s, 2H), 2.53 (s, 4H), 1.70 (s, 3H); MS (+FAB): [(M+H)+], 3 bromine isotope pattern, 772(20%), 774 (35%), 776 (45%); HRMS, Calculated sample mass: 771.93674 for formula C33H29NO4SBr3 as [M+H]; measured mass: 771.93954, mass deviation 2.80 mmu. Anal. Calc. for C33H28Br3NO4S: C, 51.18; H, 3.64; N, 1.81. Found: C, 51.57; H, 3.86; N, 1.73.

EXAMPLE 36

2-[2,6-Dibromo-4-(9-bromo-3-methyl-2-morpholin-4-ylmethyl-naphtho[2,3-b]thiophen-4-yl)-phenoxy]-propionic acid Prepared from dibromo-4-(9-bromo-3-methyl-2-morpholin-4-yl-methyl-naphtho[2,3-b]thiophen-4-yl)-phenol (Example 19) and (S)-2-hydroxy-3-phenylpropionic acid, methyl ester (Example 25) according to the procedure of Example 30. Yellow solid: [a]25/D=+13.84° (10.043 mg/mL, DMSO); NMR (pyridine-d5): δ8.42 (d, J=8 Hz, 1H), 7.88 (s, 2H), 7.63 (m, 2H), 7.41 (m, 1H), 5.61 (q, J=4 Hz, 1H), 3.78 (t, J=4 Hz, 4H), 3.70–3.63 (m, 3H), 2.56 (s, 4H), 1.97 (d, J=7 Hz, 3H), 1.71 (s, 3H); MS (+FAB): [(M+H)+], 3 bromine isotope pattern, 696 (35%), 698 (100%), 700 (80%), 702 (40%); Anal. Calc. for C27H24Br3NO4S.HCl: C, 44.14; H, 3.43; N, 1.91. Found: C, 44.94; H, 3.85; N, 1.83.

EXAMPLE 37

(R)-2-[2,6-Dibromo-4-(9-bromo-2-diethylaminomethyl-3-methyl-naphtho[2,3-b]thiophen-4-yl)-phenoxy]-3-phenyl-propionic acid Prepared from 2,6-dibromo-4-(9-bromo-2-diethylaminomethyl-3-methyl-naphtho[2,3-b]thiophen-4- yl)-phenol (Example 18) and (S)-2-hydroxy-3-phenylpropionic acid, methyl ester (Example 25) according to the procedure of Example 30. White solid: NMR (DMSO-d6); δ13.3 (broad band, 1H), 8.20 (d, J=8 Hz, 1H), 7.70(s, 2H), 7.66 (ddd, J=8, 7, 1 Hz, 1H), 7.51(ddd, J=8, 7, 1 Hz, 1H), 7.40– 7.25(m, 6H), 5.21(t, J=7 Hz, 1H), 3.75(s, 2H), 3.32(dd, J=4, 3 Hz, 2H), 2.55 (q, J=7 Hz, 4H), 1.63(s, 3H), 1.02 (t, J=7 Hz, 6H) MS [(+)FAB]: [M+H]+@ 758, 3 bromine isotope pattern, 758(25%), 760(80%), 762(75%), 764(35%), 689(100%); Anal HPLC, Primesphere 5C-18 column, eluent 62% acetonitrile for 15 minutes indicated 97.8%purity; High Resolution MS (FAB)+ve: Calculated Sample Mass: 759.95556 for formula C33H31NO3Br3 as [M+H], Measured Mass 759.97370 mass deviation: 18.14 mmu.

EXAMPLE 38

[2-Bromo-4-(9-bromo-2,3-dimethyl-naphtho[2,3-b]thiophen-4-yl)-2-nitro-phenoxy]-3-phenyl-propionic acid Prepared from of 2-bromo-4-(9-bromo-2,3-dimethyl-naphtho[2,3-b]thiophen-4-yl)-2-nitro-phenol (Example 21) and (S)-2-hydroxy-3-phenylpropionic acid, methyl ester (Example 25) according to the procedure of Example 30. White solid: mp 243–245° C.: NMR (DMSO-d6); δ11.30 (broad s, 1H), 8.23, 8.22 (2d, J=3 Hz, 1H), 8.06, 8.04 (2d, J=3 Hz, 1H), 7.95 (t, J=2, 1H), 7.68 (m, 1H), 7.56–7.50 (m, 1H), 7.45 (d, J=8 Hz, 1H),7.34–7.24 (m, 6H), 5.28 5.22 (2t, J=6 Hz, 1H), 3.40–3.23 (m, 2H), 4.82 (d, J=6 Hz, 1H), 2.46 (s, 3H), 1.59 1.57 (2s, 3H); MS (+FAB): 2 bromine isotope pattern 653, 655 , 657; Anal. Calc. for C29H21Br2NO5S: C, 53.15; H, 3.23; N, 2.14. Found: C, 53.77; H, 3.73; N, 2.04.

EXAMPLE 39

2-Bromo-4-(9-bromo-2,3-dimethyl-naphtho[2,3-b]thiophen-4-yl)-6-isopropyl-phenol

Step1

2-Isopropyl-4-(2,3-dimethyl-naphtho[2,3-b]thiophen-4-yl -phenol

In a manner similar to the procedure of Example 49, Step 1, there was obtained from 3-isopropyl-p-anisic acid (3.0 g, 16.5 mmol, RN-33537-78-9), oxalyl chloride (1.7 mL, 19.5 mmol), N,N-dimethylformamide (2 drops), 2,3-dimethyl-5-benzylthiophene (4.0 g, 19.8 mmol), tin(IV) chloride (2.1 mL, 18.2 mmol), and anhydrous methylene chloride (65 mL) the title compound as a dark red oil (6.5 g), which was used without further purification.

In a manner similar to the procedure of Example 49, Step 2, there was obtained from (2-benzyl-4,5-dimethyl-thiophen-3-yl)-(3-isopropyl-4-methoxy-phenyl)-methanone (6.5 g, 17.8 mmol), boron tribromide (9.4 mL, 99 mmol), and methylene chloride (75 mL) the title compound as a yellow solid (1.7 g, 27%): NMR (DMSO-d6): δ9.49 (s, 1H), 8.42 (s, 1H), 7.94 (d, 1H), 7.47–7.32 (m, 3H), 7.01 (s, 1H), 6.93 (s, 2H), 3.32 (m, 1H), 2.39 (s, 3H), 1.59 (s, 3H), 1.19 (d, 6H).

Step 2

Acetic acid 2-isopropyl-4-(2,3-dimethyl-naphtho[2,3-b]thiophen-4-yl)-phenyl ester In a manner similar to the procedure of Example 49, Step 3, there was obtained from 2-isopropyl-4-(2,3-dimethyl-naphtho[2,3-b]thiophen-4-yl)-phenol (0.5 g, 1.4 mmol), acetic anhydride (0.17 mL, 1.8 mmol), and pyridine (3.5 mL) the title compound as a white solid (0.48 g, 86%): NMR (DMSO-d6): δ8.49 (s, 1H), 8.00–7.96 (d, 1H), 7.48–7.31 (m, 4H), 7.20 (s, 2H), 3.10 (septet, 1H), 2.40 (s, 3H), 2.37 (s, 3H), 1.56 (s, 3H), 1.16 (d, 6H).

Step 3

Acetic acid 2-isopropyl-4-(9-bromo-2,3-dimethyl-naphtho[2,3-b]thiophen-4-yl)-phenyl ester In a manner similar to the procedure of Example 49, Step 4, there was obtained from acetic acid 2-isopropyl-4-(2,3-dimethyl-naphtho[2,3-b]thiophen-4-yl)-phenyl ester (0.38 g, 0.97 mmol), ferric chloride (8 mg, 0.51 mmol), bromine (0.055 mL, 1.1 mmol), and methylene chloride (5 mL) the title compound as a white solid (0.40 g, 88%): (DMSO-d6): δ8.20 (d, 1H), 7.67–7.62 (m, 1H), 7.52–7.43 (m, 2H), 7.34 (d, 1H), 7.22 (m, 2H), 3.09 (septet, 1H), 2.43 (s, 3H), 2.37 (s, 3H), 1.54 (s, 3H), 1.16 and 1.15 (two doublets, 6H, rotational isomers); MS(EI): [M+], 1 bromine isotope pattern, 466/468; Anal. Calc. for C25H23BrO2S: C, 64.24; H, 4.96; N, 0.00. Found: C, 63.84; H, 4.90; N, 0.06.

Step 4

2-Isopropyl-4-(9-bromo-2,3-dimethyl-naphtho[2,3-b]thiophen-4-yl)-phenol

In a manner similar to the procedure of Example 49, Step 5, there was obtained from acetic acid 2-isopropyl-4-(9-bromo-2,3-dimethyl-naphtho[2,3-b]thiophen-4-yl)-phenyl ester (0.39 g, 0.83 mmol), aqueous potassium hydroxide (1.0 mL of a 1 N solution, 1.0 mmol), tetrahydrofuran (14 mL), and methanol (8.5 mL) there was obtained the title compound as a cream solid (0.35 g, 99%): (DMSO-d6): δ9.56 (s, 1H), 8.17 (d, 1H), 7.64–7.60 (ddd, 1H), 7.53–7.52 (d, 1H), 7.46–7.42 (ddd, 1H), 7.03 (d,1H), 6.97–6.91 (m, 2H), 3.31–3.28 (m,1H), 2.42 (s, 3H), 1.58 (s, 3H), 1.16 (d, 6H); MS(EI): [M+], 1 bromine isotope pattern, 424/426; Anal. Calc. for C23H21BrOS: C, 64.94; H, 4.98; N, 0.00. Found: C, 64.11; H, 4.99; N, 0.03.

Step 5

2-Bromo-4-(9-bromo-2,3-dimethyl-naphtho[2,3-b]thiophen-4-yl)-6-isopropyl-phenol

To a suspension of 2-isopropyl-4-(9-bromo-2,3-dimethyl-naphtho[2,3-b]thiophen-4-yl)-phenol (0.35 g, 0.81 mmol) and potassium acetate (0.80 g, 8.11 mmol) in glacial acetic acid (11 mL) was added a solution of bromine (0.05 mL, 0.97 mmol) in glacial acetic acid (1.5 mL) dropwise at room temperature. An additional 1 mL of acetic acid was used to rinse the pipette and flask. After stirring at room temperature for 4 h the reaction was quenched with a small amount of dilute sodium bisulfite and diluted with water (100 mL). The white solid was collected on a sintered glass funnel, washed well with water and dried (Na2SO4) to give the title compound as a white solid (0.40 g, 98%): mp 157–162° C.; (DMSO-d6): δ9.20 (s, 1H), 8.19 (d, 1H), 7.66–7.61 (m, 1H), 7.49–7.48 (m, 2H), 7.35 (d, 1H), 7.13 (d,1H), 3.40 (septet, 1H), 2.42 (s, 3H), 1.60 (s, 3H), 1.16 (d, 6H); MS(+FAB): [M+H], 2 bromine isotope pattern, 502 (12%), 504 (30%), 506 (18%); Anal. Calc. for C23H20Br2OS: C, 54.78; H, 4.00; N, 0.00. Found: C, 53.67; H, 3.84; N, 0.03.

EXAMPLE 40

(R)-2-[2-Bromo-4-(9-bromo-2,3-dimethyl-naphtho[2,3-b]thiophen-4-yl)-6-isopropyl-phenoxy]-3-phenyl-propionic acid Step 1

(2R)-2-[2-Bromo-4-(9-bromo-2,3-dimethyl-naphtho[2,3-b]thiophen-4-yl)-6-isopropyl-phenoxy]-3-phenyl-propionic acid methyl ester In a manner similar to the procedure of Example 49, Step 6, there was obtained from 2-bromo-4-(9-bromo-2,3- dimethyl-naphtho[2,3-b]thiophen-4yl)-6-isopropyl-phenol (0.36 g, 0.72 mmol), (S)-2-hydroxy-3-phenylpropionic acid, methyl ester (0.19 g, 1.1 mmol), triphenylphosphine (0.28 g, 1.1 mmol), diethylazodicarboxylate (0.17 mL, 1.1 mmol), and anhydrous benzene (4.0 mL) in an oil bath (80° C.) for 4.5 h the title compound as a white solid (0.27 g, 56%): (DMSO-d6): δ8.20 (d, 1H), 7.70–7.60 (m, 1H), 7.60–7.40 (m, 2H), 7.40–7.20 (m, 7H), 5.07 and 4.95 (two triplets, 1H, rotational isomers), 3.60 and 3.56 (two s, 3H, rotational isomers), 3.40–3.20 (m, 3H), 2.45 and 2.43 (two singlets, 3H, rotational isomers), 1.59 and 1.53 (two singlets, 3H, rotational isomers), 1.20–1.00 (m, 6H).

Step 2

(2R)-2-[2-Bromo-4-(9-bromo-2,3-dimethyl-naphtho [2,3-b]thiophen-4-yl)-6-isopropyl-phenoxy]-3-phenyl-propionic acid In a manner similar to the procedure of Example 49, Step 7, there was obtained from (2R)-2-[2-bromo-4-(9-bromo-2, 3-dimethyl-naphtho[2,3-b]thiophen-4-yl)-6- isopropyl-phenoxy]-3-phenyl-propionic acid methyl ester (0.26 g, 0.52 mmol), aqueous potassium hydroxide (1.1 mL of a 1 N solution, 1.1 mmol), tetrahydrofuran (6 mL), and methanol (2 mL) the title compound as a white solid (0.23 g, 68%): Opt. Rot. [a]25/D=+38.90 (9.970 mg/mL, CHCl3); (DMSO-d6): δ13.1 (broad s, 1H), 8.19 (d, 1H), 7.68–7.62 (m, 1H), 7.53–7.44 (m, 2H), 7.40–7.38 (m, 1H), 7.35–7.30 (m, 4H), 7.29–7.23 (m, 2H), 5.00 (m, 1H), 3.55 (septet, 1H), 3.35 (m, 2H), 2.42 and 2.43 (two singlets, 3H, rotational isomers), 1.57 and 1.52 (two singlets, 3H, rotational isomers), 1.14–1.03 (m, 6H); MS(+FAB): [M+], 2 bromine isotope pattern, 650 (15%), 652 (30%), 654 (21%); Anal. Calc. for C32H28Br2O3S: C, 58.91; H, 4.33; N, 0.00. Found: C, 58.72; H, 4.45; N, 0.10.

EXAMPLE 41

(R)-2-[4-(2,3-dimethyl-naphtho[2,3-b]thiophen-4-yl)-2-isopropyl-phenoxy]-3-phenyl-propionic acid Step 1

(R)-2-[4-(2,3-Dimethyl-naphtho[2,3-b]thiophen-4-yl)-2-isopropyl-phenoxy]-3-phenyl-propionic acid methyl ester In a manner similar to the procedure of Example 49, Step 6, there was obtained from 4-(2,3-dimethyl-naphtho[2,3-b] thiophen-4-yl)-2-isopropyl-phenol (0.30 g, 0.87 mmol), (S)-2-hydroxy-3-phenylpropionic acid, methyl ester (0.62 g, 3.5 mmol), triphenylphosphine (0.91 g, 3.5 mmol), diethylazodicarboxylate (0.54 mL, 3.5 mmol), and anhydrous benzene (7.0 mL) in an oil bath (85° C.) for 18 h the title compound as a yellow oil (0.18 g, 41%): (DMSO-d6): δ8.40 (s, 1H), 7.90 (d, 1H), 7.50–7.20 (m, 6H), 7.20–7.00 (m, 3H), 7.00–6.80 (m, 2H), 5.20 (t,1H), 3.65 and 3.63 (two s, 3H, rotational isomers), 3.30–3.20 (m, 3H), 2.40 (s, 3H), 1.50 (s, 3H), 1.15 (two doublets, 3H, rotational isomers), 1.05 (two doublets, 3H, rotational isomers).

Step 2

(R)-2-[4-(2,3-Dimethyl-naphtho[2,3-b]thiophen-4-yl)-2-isopropyl-phenoxy]-3-phenyl-propionic acid In a manner similar to the procedure of Example 49, Step 7, there was obtained from (R)-2-[4-(2,3-dimethyl-naphtho [2,3-b]thiophen-4-yl)-2-isopropyl-phenoxy]-3-phenyl-propionic acid methyl ester (0.18 g, 0.35 mmol), aqueous potassium hydroxide (0.71 mL of a 1 N solution, 0.71 mmol), tetrahydrofuran (6 mL), and methanol (2 mL) the title compound as a white solid (0.072 g, 41%): (DMSO-d6): δ13.10 (broad s, 1H), 8.43 (d, 1H), 7.49 (dd, 1H), 7.46–7.29 (m, 7H), 7.28–7.22 (m, 1H), 7.10–7.03 (m, 2H), 6.89–6.85 (m, 1H), 5.07 (m, 1H), 3.40–3.19 (m, 3H), 2.38 and 2.37 (two singlets, 3H, rotational isomers), 1.53 and 1.51 (two singlets, 3H, rotational isomers), 1.15 and 1.14 (two doublets, 3H, rotational isomers), 1.03 (d, 3H); MS(EI): [M+] 494; Anal. Calc. for C32H30O3S: C, 77.70; H, 6.11; N, 0.00. Found: C, 75.71; H, 6.29; N, 0.03.

EXAMPLE 42

(R)-2-[2-Bromo-4-(9-bromo-2,3-dimethyl-naphtho [2,3-b]thiophen-4-yl)-6-sec-butyl-phenoxy]-3-phenyl-propionic acid (WAY-143461)

Step 1

2-Sec-butyl-4-(2,3-dimethyl-naphtho[2,3-b] thiophen-4-yl)-phenol

In a manner similar to the procedure of Example 49, Step 1, there was obtained from 3-sec-butyl-p-anisic acid (3.0 g, 14.4 mmol, prepared by the method of M. Derenberg and P. Hodge, *Tetrahedron Lett.* 1971, 3825–3828; D. G. Davies, et al., *J. Chem. Soc.* (C) 1971, 455–460), oxalyl chloride (1.4 mL, 15.8 mmol), N,N-dimethylformamide (2 drops), 2,3-dimethyl-5-benzylthiophene (3.5 g, 16.6 mmol), tin(IV) chloride (1.5 mL, 15.8 mmol), and anhydrous methylene chloride (92 mL) an oil (6.2 g), which was used without further purification.

In a manner similar to the procedure of Example 49, Step 1, there was obtained from (2-benzyl-4,5-dimethyl-thiophen-3-yl)-(3-sec-butyl-4-methoxy-phenyl)-methanone (6.2 g, 15.8 mmol), boron tribromide (7.1 mL, 74.8 mmol), and methylene chloride (54 mL) the title compound as a solid (2.34 g, 41%): MS(EI): [M+] 360.

Step 2

2-Bromo-4-(9-bromo-2,3-dimethyl-naphtho[2,3-b] thiophen-4-yl)-6-sec-butyl-phenol In a manner similar to the procedure of Example 39, Step 6, there was obtained from 2-sec-butyl-4-(2,3-dimethyl-naphtho[2,3-b]thiophen-4-yl)-phenol (2.34 g, 6.5 mmol), bromine (0.69 mL, 13 mmol), potassium acetate (6.4 g, 65 mmol), and glacial acetic acid (65 mL) the title compound as a solid (0.63 g, 19%): MS(EI): [M+], 2 bromine isotope pattern, 516 (50%), 518 (100%), 520 (55%).

Step 3

(R)-2-[2-Bromo-4-(9-bromo-2,3-dimethyl-naphtho [2,3-b]thiophen-yl)-6-sec-butyl-phenoxy]-3-phenyl-propionic acid In a manner similar to the procedure of Example 49, Step 6, there was obtained from 2-bromo-4-(9-bromo-2,3-dimethyl-naphtho[2,3-b]thiophen-4-yl)-6-sec-butyl-phenol (0.63 g, 1.2 mmol), (S)-2-hydroxy-3-phenylpropionic acid, methyl ester (0.44 g, 2.4 mmol), triphenylphosphine (0.64 g, 2.4 mmol), diethylazodicarboxylate (0.38 mL, 2.4 mmol), and anhydrous benzene (2.4 mL) at room temperature for 5 days an oil (0.60 g, 72%), which was used without further purification.

In a manner similar to the procedure of Example 49, Step 7, there was obtained from (R)-2-[2-bromo-4-(9-bromo-2, 3-dimethyl-naphtho[2,3-b]thiophen-4-yl)-6-sec-butyl-phenoxy]-3-phenyl-propionic acid methyl ester (0.55 g, 0.73 mmol), aqueous potassium hydroxide (1.6 mL of a 1 N solution, 1.6 mmol), tetrahydrofuran (7.5 mL), and methanol (2.5 mL) the title compound as a foam (0.26 g, 48%): MS(EI): [M+], 2 bromine isotope pattern, 664 (14%), 666 (26%), 668 (14%); Anal. Calc. for C33H30Br2O3S: C, 59.47; H, 4.54; N, 0.00. Found: C, 59.44; H, 4.81; N, 0.03.

EXAMPLE 43

(R)-2-[2-Bromo-4-(9-bromo-2,3-dimethyl-naphtho[2,3-b]thiophen-4-yl)-6-ethyl-phenoxy]-3-phenyl-propionic acid Step 1

(2-Benzyl-4,5-dimethyl-thiophen-3-yl)-(3-ethyl-4-methoxy-phenyl)-methanone

In a manner similar to the procedure of Example 49, Step 1, there was obtained from 3-ethyl-p-anisic acid (5.0 g, 27.7 mmol, RN-22934-35-6), oxalyl chloride (2.7 mL, 30.5 mmol), N,N-dimethylformamide (2 drops), 2,3-dimethyl-5-benzylthiophene (6.7 g, 33.2 mmol), tin(IV) chloride (3.6 mL, 30.5 mmol), and anhydrous methylene chloride (177 mL) the title compound as an oil (5.2 g, 51%): (DMSO-d6): δ7.59–7.54 (m, 2H), 7.25–7.11 (m, 3H), 7.09–7.04 (m, 3H), 3.87 (s, 3H), 3.84 (s, 2H), 2.57 (q, 2H), 2.26 (s, 3H), 1.82 (d, 3H), 1.10 (t, 3H); MS(+FAB): [M+H] 365; Anal. Calc. for C23H24O2S: C, 75.79; H, 6.64; N, 0.00. Found: C, 75.34; H, 6.72; N, 0.00.

Step 2

2-Ethyl-4-(2,3-dimethyl-naphtho[2,3-b]thiophen-4-yl)-phenol

In a manner similar to the procedure of Example 49, Step 2, there was obtained from (2-benzyl-4,5-dimethyl-thiophen-3-yl)-(3-ethyl-4-methoxy-phenyl)-methanone (6.1 g, 16.7 mmol), boron tribromide (7.1 mL, 75.4 mmol), and methylene chloride (58 mL) the title compound as a solid (2.6 g, 46%): (DMSO-d6): δ9.49 (s, 1H), 8.42 (s, 1H), 7.93 (d, 1H), 7.47 (d, 1H), 7.43 (m, 1H), 7.33 (m, 1H), 7.02–6.90 (m containing a singlet at δ6.94, 3H), 2.73–2.52 (complex m, ABX pattern, 2H, rotational isomers), 2.40 (s, 3H), 1.62 (s, 3H), 1.15 (t, 3H); MS(EI): [M+] 332.

Step 3

(R)-2-[2-Bromo-4-(9-bromo-2,3-dimethyl-naphtho[2,3-b]thiophen-4-yl)-6-ethyl-phenoxy]-3-phenyl-propionic acid methyl ester In a manner similar to the procedure of Example 39, Step 6, there was obtained from 2-ethyl-4(2,3-dimethyl-naphtho[2,3-b]thiophen-4-yl)-phenol (2.6 g, 7.8 mmol), bromine (0.83 mL, 15.7 mmol), potassium acetate (7.7 g, 78.5 mmol), and glacial acetic acid (78 mL) the title compound as a solid (0.73 g), which was used without further purification.

In a manner similar to the procedure of Example 49, Step 6, there was obtained from 2-bromo-4-(9-bromo-2,3-dimethyl-naphtho[2,3-b]thiophen-4-yl)-6-ethyl-phenol (0.73 g, 1.5 mmol), (S)-2-hydroxy-3-phenylpropionic acid, methyl ester (0.54 g, 3.0 mmol), triphenylphosphine (0.78 g, 3.0 mmol), diethylazodicarboxylate (0.47 mL, 3.0 mmol), and anhydrous benzene (3.0 mL) at room temperature for 5 days an oil (0.58 g, 60%): (DMSO-d6): δ8.19 (d, 1H), 7.65 (m, 1H), 7.54–7.22 (m containing a singlet at δ7.32, 9H), 5.09 and 5.01 (two t, 1H, rotational isomers), 3.60 and 3.56 (two s, 3H, rotational isomers), 3.45–3.25 (complex m, 2H, rotational isomers), 2.78–2.50 (complex m, ABX pattern, 2H), 2.42 and 2.43 (two s, 3H, rotational isomers), 1.59 and 1.54 (two s, 3H, rotational isomers), 1.09 and 1.07 (two t, 3H, rotational isomers).

Step 4

(R)-2-[2-Bromo-4-(9-bromo-2,3-dimethyl-naphtho[2,3-b]thiophen-4-yl)-6-ethyl-phenoxy]-3-phenyl-propionic acid In a manner similar to the procedure of Example 49, Step 7, there was obtained from (R)-2-[2-bromo-4-(9-bromo-2,3-dimethyl-naphtho[2,3-b]thiophen-4-yl)-6-ethyl-phenoxy]-3-phenyl-propionic acid methyl ester (0.41 g, 0.63 mmol), aqueous potassium hydroxide (1.3 mL of a 1 N solution, 1.3 mmol), tetrahydrofuran (4.5 mL), and methanol (1.5 mL) the title compound as a pale yellow solid (0.38 g, 95%): (DMSO-d6): δ13.05 (br s, 1H), 8.20 (d, 1H), 7.65 (m, 1H), 754–7.18 (m, 9H), 5.05 (m, 1H), 3.33 (m, 2H), 2.90–2.50 (complex m, ABX pattern, 2H), 2.43 and 2.41 (two s, 3H, rotational isomers), 1.58 and 1.53 (two s, 3H, rotational isomers), 1.10 and 1.09 (two t, 3 H, rotational isomers); MS(-ESI): [M−H], 2 bromine isotope pattern, 635 (44%), 637 (100%), 639 (62%); Anal. Calc. for C31H26Br2O3S: C, 58.32; H, 4.11; N, 0.00. Found: C, 58.11; H, 4.32; N, 0.18.

EXAMPLE 44

(R)-2-[4-(9-Bromo-2,3-dimethyl-naphtho[2,3-b]thiophen-4-yl)-6-isopropyl-phenoxy]-3-phenyl-propionic acid Step 1

(2R)-2-[4-(9-Bromo-2,3-dimethyl-naphtho[2,3-b]thiophen-4-yl)-6-isopropyl-phenoxy]-3-phenyl-propionic acid methyl ester In a manner similar to the procedure of Example 49, Step 6, there was obtained from 4-(9-bromo-2,3-dimethyl-naphtho[2,3-b]thiophen-4-yl)-2,6-isopropyl-phenol (0.26 g, 0.67 mmol), (S)-2-hydroxy-3-phenylpropionic acid, methyl ester (0.32 g, 1.8 mmol), triphenylphosphine (0.46 g, 1.8 mmol), diethylazodicarboxylate (0.28 mL, 1.8 mmol), and anhydrous benzene (7.0 mL) in an oil bath (90° C.) for 4.5 h the title compound as a white solid (0.15 g, 38%): (DMSO-d6): δ8.18 (m, 1H), 7.66–7.58 (m, 1H), 7.50–7.40 (m, 2H), 7.40–7.30 (m,4H), 7.30–7.20 (m, 1H), 7.14–7.04 (m, 2H), 6.92–6.87 (m, 1H), 5.27 (t, 1H), 3.70 and 3.65 (two singlets, 3H, rotational isomers), 3.40–3.20 (m, 3H), 2.40 (s, 3H), 1.49 (s, 3H), 1.15 and 1.13 (two doublets, 3H, rotational isomers), 1.06 and 1.04 (two doublets, 3H, rotational isomers).

Step 2

(2R)-2-[4-(9-Bromo-2,3-dimethyl-naphtho[2,3-b]thiophen-4-yl)-2-isopropyl-phenoxy]-3-phenyl-propionic acid In a manner similar to the procedure of Example 49, Step 7, there was obtained from (2R)-2-[4-(9-bromo-2,3-dimethyl-naphtho[2,3-b]thiophen-4-yl)-2-isopropyl-phenoxy]-3-phenyl-propionic acid methyl ester (0.15 g, 0.25 mmol), aqueous potassium hydroxide (0.50 mL of a 1 N solution, 0.50 mmol), tetrahydrofuran (6 mL), and methanol (2 mL) the title compound as a white solid (0.14 g, 95%): (DMSO-d6): δ13.14 (broad s, 1H), 8.18–8.15 (m,1H), 7.64–7.58 (m, 1H), 7.48–7.31 (m, 6H), 7.30–7.22 (m, 1H), 7.11–7.04 (m, 2H), 6.90–6.85 (m, 1H), 5.07 (m,1H). 3.39–3.18 (m, 3H), 2.41 and 2.40 (two singlets, 3H, rotational isomers), 1.51 and 1.49 (two singlets, 3H, rotational isomers), 1.15 and 1.14 (two doublets, 3H, rotational isomers), 1.04 and 1.03 (two doublets, 3H, rotational isomers); MS(EI): [M+], 1 bromine isotope pattern, 572/574; Anal. Calc. for C32H29BrO3S: C, 67.01; H, 5.10; N, 0.00. Found: C, 67.19; H, 5.47; N, 0.03.

EXAMPLE 45

(R)-2-[2-Cyclopentyl-4-(2,3-dimethyl-naphtho[2,3-b]thiophen-4-yl)phenoxy]-3-phenyl-propionic acid Step 1

(2-Benzyl-4,5-dimethyl-thiophen-3-yl)-(3-cyclopentyl-4-methoxy-phenyl)-methanone To a slurry of 3-cyclopentyl-p-anisic acid (5.0 g, 22.7 mmol, RN-59216-82-9) in anhydrous methylene chloride (60 mL) was added oxalyl chloride (2.4 mL, 27.2 mmol) and N,N-dimethylformamide (2 drops) at room temperature under nitrogen. After stirring for 1.5 h the reaction mixture was concentrated under reduced pressure. The residue was dissolved in carbon disulfide (32 mL) and the resulting solution was added to 2,3-dimethyl-5-benzylthiophene (5.1 g, 25.0 mmol). At −78° C. under nitrogen, tin(IV) chloride (2.9 mL, 25.0 mmol) was added, and the reaction mixture was then stirred at room temperature for 4 h. The solution was poured onto a mixture of ice and water (200 mL) and extracted with diethyl ether (200 mL). The diethyl ether layer was washed twice with sodium bicarbonate (50 mL) and once with brine (50 mL). Concentration under reduced pressure and chromatography with petroleum ether:ethyl acetate (95:5) gave the title compound as an amber oil (4.8 g, 52%): (DMSO-d6): δ7.61–7.54 (m, 2H), 7.24–7.14 (m, 3H), 7.08–7.02 (m, 3H), 3.87 (s, 3H), 3.84 (s, 2H), 3.42–3.30 (m, 1H), 2.26 (s, 3H), 2.00–1.85 (m, 2H), 1.81 (s, 3H), 1.74–1.58 (m, 4H), 1.48–1.36 (m, 2H); MS(EI): [M+] 404; Anal. Calc. for C26H28O2S: C, 77.19; H, 6.98; N, 0.00. Found: C, 76.26; H, 7.24; N, 0.04.

Step 2

2-Cyclopentyl-4-(2,3-dimethyl-naphtho[2,3-b]thiophen-4-yl)-phenol

To (2-benzyl-4,5-dimethyl-thiophen-3-yl)-(3-cyclopentyl-4-methoxy-phenyl)-methanone (4.8 g, 11.7 mmol) in anhydrous methylene chloride (70 mL) at −78° C. under nitrogen was added dropwise over a period of 20 min boron tribromide (3.6 mL, 37.6 mmol). The reaction mixture was then allowed to stir at room temperature for 22 h. The solution was poured onto a mixture of ice and water (600 mL) and extracted with diethyl ether (800 mL). The diethyl ether layer was washed twice with water (500 mL) and once with brine (500 mL). Concentration under reduced pressure and chromatography with petroleum ether:ethyl acetate (97:3) gave the title compound as a white solid (3.4 g, 78%): mp 156–158° C.; (DMSO-d6): δ9.48 (s, 1H), 8.42 (s, 1H), 7.93 (d, 1H), 7.46–7.41 (m, 2H), 7.35–7.30 (m, 1H), 7.00 (s, 1H), 6.95–6.90 (m, 2H), 3.38–3.28 (m, 1H), 2.39 (s, 3H), 1.99–1.90 (m, 2H), 1.68–1.47 (m, 6H), 1.60 (s, 3H); MS(EI): [M+] 372; Anal. Calc. for C25H24OS: C, 80.60; H, 6.49; N, 0.00. Found: C, 80.39; H, 6.43; N, 0.04.

Step 3

(R)-2-[2-Cyclopentyl-4-(2,3-dimethyl-naphtho[2,3-b]thiophen-4-yl)-phenoxy]-3-phenyl-propionic acid methyl ester In a manner similar to the procedure of Example 49, there was obtained from 2-cyclopentyl-4-(2,3-dimethyl-naphtho[2,3-b]thiophen-4-yl)-phenol (0.40 g, 1.1 mmol), (S)-2-hydroxy-3-phenylpropionic acid, methyl ester (0.29 g, 1.6 mmol), triphenylphosphine (0.42 g, 1.6 mmol), diethylazodicarboxylate (0.25 mL, 1.6 mmol), and anhydrous benzene (6.0 mL) in an oil bath (80° C.) for 6 h the title compound as a white solid (0.26 g, 46%): (DMSO-d6): δ8.44 (s, 1H), 7.94 (d, 1H), 7.43–7.26 (m, 8H), 7.08–7.01 (m, 2H), 6.88–6.85 (m, 1H), 5.24 (dd,1H), 3.70 and 3.66 (two singlets, 3H, rotational isomers), 3.42–3.20 (m, 3H), 2.38 (s, 3H), 2.02–1.30 (m containing a singlet at δ1.52, 11H).

Step 4

(R)-2-[2-Cyclopentyl-4-(2,3-dimethyl-naphtho[2,3-b]thiophen-4-yl)-phenoxy]-3-phenyl-propionic acid In a manner similar to the procedure of Example 49, Step 7, there was obtained from (R)-2-[2-cyclopentyl-4-(2,3-dimethyl-naphtho[2,3-b]thiophen-4-yl)-phenoxy]-3-phenyl-propionic acid methyl ester (0.22 g, 0.41 mmol), aqueous potassium hydroxide (0.82 mL of a 1 N solution, 0.82 mmol), tetrahydrofuran (12 mL), and methanol (4 mL) the title compound as a white solid (0.21 g, 95%): Opt. Rot. [a]25/D=−8.19° (8.549 mg/mL, CHCl3); (DMSO-d6): δ13.10 (broad s, 1H), 8.43 (d, 1H), 7.93 (m, 1H), 7.43–7.20 (m, 8H), 7.07–7.02 (m, 2H), 6.88–6.84 (m, 1H), 5.03 and 5.07 (two dd, 1H, rotational isomers), 3.39–3.17 (m, 3H), 2.38 and 2.37 (two singlets, 3H, rotational isomers), 1.90 (m, 1H), 1.76 (m, 1H), 1.70–1.32 (m containing two singlets at δ1.54 and 1.52 (rotational isomers), 9H); MS(EI): [M+] 520; Anal. Calc. for C34H32O3S: C, 78.43; H, 6.19; N, 0.00. Found: C, 77.96; H, 6.40; N, 0.02; Analytical HPLC indicates a major component (96.9%).

EXAMPLE 46

(R)-2-[4-(2,3-Dimethyl-naphtho[2,3-b]thiophen-4-yl)-2,6-dimethyl-phenoxy]-3-phenyl-propionic acid Step 1

(R)-2-[4-(2,3-Dimethyl-naphtho[2,3-b]thiophen-4-yl)-2,6-dimethyl-phenoxy]-3-phenyl-propionic acid methyl ester In a manner similar to the procedure of Example 49, Step 6, there was obtained from 4-(2,3-dimethyl-naphtho[2,3-b]thiophen-4-yl)-2,6-dimethyl-phenol (0.40 g, 1.2 mmol), (S)-2-hydroxy-3-phenylpropionic acid, methyl ester (0.49 g, 2.7 mmol), triphenylphosphine (0.71 g, 2.7 mmol), diethylazodicarboxylate (0.36 mL, 2.7 mmol), and anhydrous benzene (13 mL) in an oil bath (70–86° C.) for 10 h the title compound as a white solid (0.24 g, 40%): (DMSO-d6): δ8.44 (s, 1H), 7.94 (d, 1H), 7.45–7.39 (m, 2H), 7.35–7.30 (m, 5H), 7.28–7.24 (m, 1H), 6.96 (s, 2H), 4.77 (t, 1H), 3.56 (s,3H), 3.34–3.25 (m, 2H), 2.39 (s, 3H), 2.22 (s, 3H), 2.17 (s, 3H), 1.56 (s, 3H); MS(EI): [M+] 494; Anal. Calc. for C32H30O3S: C, 77.70; H, 6.11; N, 0.00. Found: C, 76.53; H, 5.85; N, 0.08.

Step 2

(R)-2-[4-(2,3-Dimethyl-naphtho[2,3-b]thiophen-4-yl)-2,6-dimethyl-phenoxy]-3-phenyl-propionic acid In a manner similar to the procedure of Example 49, Step 7, there was obtained from (R)-2-[4-(2,3-dimethyl-naphtho[2,3-b]thiophen-4-yl)-2,6-dimethyl-phenoxy]-3-phenyl-propionic acid methyl ester (0.23 g, 0.46 mmol), aqueous potassium hydroxide (0.91 mL of a 1 N solution, 0.91 mmol), tetrahydrofuran (12 mL), and methanol (4 mL) the title compound as a white solid (0.19 g, 86%): Opt. Rot. [a]25/D=+33.040 (10.170 mg/mL, MeOH); (DMSO-d6): δ12.9 (broad s, 1H), 8.44 (s, 1H), 7.94 (d, 1H), 7.45–7.40 (m, 2H), 7.35–7.22 (m, 6H), 6.95 (s, 2H), 4.70 (t, 1H), 3.25 (d, 2H), 2.38 (s, 3H), 2.24 (s, 3H), 2.22 (s, 3H), 1.56 (s, 3H); MS(EI): [M+] 480; Anal. Calc. for C31H28O3S: C, 77.47; H, 5.87; N, 0.00. Found: C, 76.23; H, 5.77; N, 0.03; Analytical HPLC indicates a major component (94.6%).

EXAMPLE 47

(R)-2-[4-(9-Bromo-2,3-dimethyl-naphtho[2,3-b]thiophen-4-yl)-2-cyclopentyl-phenoxy]-3-phenyl-propionic acid Step 1

Acetic acid 2-cyclopentyl-4-(2,3-dimethyl-naphtho[2,3-b]thiophen-4-yl)-phenyl ester To 2-cyclopentyl-4-(2,3-dimethyl-naphtho[2,3-b]thiophen-4-yl)-phenol (2.8 g, 7.5 mmol) in anhydrous pyridine (20 mL) at room temperature under nitrogen was added dropwise acetic anhydride (0.92 mL, 9.8 mmol). The reaction mixture was placed in the refrigerator. After 41 h the reaction was diluted and acidified with 10% aqueous hydrochloric acid to a pH of 1. The mixture was extracted with diethyl ether (500 mL), and the diethyl ether layer was washed with 5% aqueous hydrochloric acid (100 mL), twice with water (100 mL), brine (100 mL), and then dried (MgSO4). Concentration under reduced pressure gave the title compound as a white solid (3.1 g, 98%): (DMSO-d6): δ8.48 (s, 1H), 7.97 (d, 1H), 7.47–7.43 (m, 1H), 7.38–7.36 (m, 2H), 7.28 (s, 1H), 7.19 (d, 2H), 3.14 (quintet, 1H), 2.40 (s, 3H), 2.37 (s, 3H), 1.99–1.91 (m, 2H), 1.69–1.40 (m, 6H), 1.56 (s, 3H); MS(EI): [M+] 414; Anal. Calc. for C27H26O2S: C, 78.23; H, 6.32; N, 0.00. Found: C, 77.68; H, 6.39; N, 0.04.

Step 2

Acetic acid 2-cyclopentyl-4-(9-bromo-2,3-dimethyl-naphtho[2,3-b]thiophen-4-yl)-phenyl ester To acetic acid 2-cyclopentyl-4-(2,3-dimethyl-naphtho[2,3-b]thiophen-4-yl)-phenyl ester (2.9 g, 7.7 mmol) in anhydrous methylene chloride (68 mL) was added ferric chloride (66 mg, 0.41 mmol). The reaction mixture was placed under nitrogen and cooled to −78° C. The reaction mixture was protected from light and a solution of bromine (0.44 mL, 8.5 mmol) in anhydrous methylene chloride (11 mL) was added dropwise over a period of 15 min. After stirring at −78° C. for 45 min the reaction was quenched with dilute sodium bisulfite, and then poured into water (200 mL). The resulting mixture was extracted with diethyl ether (300 mL), and the diethyl ether layer was washed with water and then brine. Concentration under reduced pressure and chromatography with petroleum ether:ethyl acetate (95:5) gave the title compound as a white solid (2.7 g, 79%): (CDCl3): δ8.28 (d, 1H), 7.58–7.52 (m, 2H), 7.39–7.34 (m, 1H), 7.29 (d, 1H), 7.18 (dd, 1H), 7.14 and 7.13 (d, 1H), 3.18 (quintet, 1H), 2.44 (s, 3H), 2.40 (s, 3H), 2.06–2.02 (m, 2H), 1.75–1.45 (m containing a singlet at δ1.60, 9H); MS(EI): [M+], 1 bromine isotope pattern, 492/494; Anal. Calc. for C27H25BrO2S: C, 65.72; H, 5.11; N, 0.00. Found: C, 63.18; H, 4.96; N, 0.00.

Step 3

2-Cyclopentyl-4-(9-bromo-2,3-dimethyl-naphtho[2,3-b]thiophen-4-yl)-phenol

To acetic acid 2-cyclopentyl-4-(9-bromo-2,3-dimethyl-naphtho[2,3-b]thiophen-4-yl)-phenyl ester (2.7 g, 5.4 mmol) in tetrahydrofuran (88 mL) and methanol (30 mL) at room temperature was added dropwise an aqueous potassium hydroxide (6.5 mL of a 1N solution, 6.5 mmol). After 1.5 h the reaction mixture was concentrated under reduced pressure. The resulting residue was combined with water (200 mL) and acidified with 10% aqueous hydrochloric acid to a pH of 1. The solution was extracted with diethyl ether (300 mL) and the diethyl ether layer was washed twice with water and dried (Na2SO4). Concentration under reduced pressure gave the title compound as a white solid (2.4 g, 100%): (DMSO-d6): δ9.54 (s, 1H), 8.16 (d, 1H), 7.61 (m, 1H), 7.52 (s, 1H), 7.43 (m, 1H), 7.03 (s, 1H), 6.93 (m, 2H), 3.32 (m, 1H), 2.41 (s, 3H), 1.94 (m, 2H), 1.58 (s, 3H), 1.72–1.42 (m, 6H); MS(EI): [M+], 1 bromine isotope pattern, 450/452; Anal. Calc. for C25H23BrOS: C, 66.52; H, 5.13; N, 0.00. Found: C, 67.17; H, 5.25; N, 0.04.

Step 4

(R)-2-[4-(9-Bromo-2,3-dimethyl-naphtho[2,3-b]thiophen-4-yl)-2-cyclopentyl-phenoxy]-3-phenyl-propionic acid methyl ester In a manner similar to the procedure of Example 49, Step 6, there was obtained from 4-(9-bromo-2,3-dimethyl-naphtho[2,3-b]thiophen-4-yl)-2-cyclopentyl-phenol (0.40 g, 0.89 mmol), (S)-2-hydroxy-3-phenylpropionic acid, methyl ester (0.48 g, 2.7 mmol), triphenylphosphine (0.70 g, 2.7 mmol), diethylazodicarboxylate (0.42 mL, 2.7 mmol), and anhydrous benzene (6 mL) in an oil bath (85° C.) for 4.5 h the title compound as a white solid (0.19 g, 34%): NMR (DMSO-d6): δ8.17 (d, 1H), 7.64–7.59 (m, 1H), 7.45–7.40 (m, 2H), 7.38–7.24 (m, 5H), 7.10–7.03 (m, 2H), 6.90–6.86 (m, 1H), 5.28–5.24 (m, 1H), 3.70 and 3.66 (two singlets, 3H, rotational isomers), 3.40–3.24 (m, 3H), 2.40 (s, 3H), 1.95–1.30 (m, 8H), 1.49 (s, 3H); MS(EI): [M+], 1 bromine isotope pattern, 612/614.

Step 5

(R)-2-[4-(9-Bromo-2,3-dimethyl-naphtho[2,3-b]thiophen-4-yl)-2-cyclopentyl-phenoxy]-3-phenyl-propionic acid In a manner similar to the procedure of Example 49, Step 7, there was obtained from (R)-2-[4-(9-bromo-2,3-dimethyl-naphtho[2,3-b]thiophen-4-yl)-2-cyclopentyl-phenoxy]-3-phenyl-propionic acid methyl ester (0.18 g, 0.30 mmol), aqueous potassium hydroxide (0.39 mL of a 1 N solution, 0.39 mmol), tetrahydrofuran (6 mL), and methanol (2 mL) the title compound as a white solid (0.15 g, 84%): NMR (DMSO-d6): δ13.12 (broad s, 1H), 8.18–8.15 (m, 1H), 7.64–7.58 (m, 1H), 7.47–7.22 (m, 7H), 7.10–7.04 (m, 2H), 6.89–6.86 (m, 1H), 5.10–5.03 (m, 1H), 3.32–3.18 (m, 3H), 2.40 (s, 3H), 1.90 (m, 1H), 1.76 (m, 1H), 1.70–1.30 (m containing two singlets at δ1.51 and 1.50 (rotational isomers), 9H); MS(−ESI): [M−H], 1 bromine isotope pattern, 597/599; Anal. Calc. for C34H31BrO3S: C, 68.11; H, 5.21; N, 0.00. Found: C, 68.10; H, 5.31; N, 0.01.

EXAMPLE 48

(R)-2-[2-Bromo-4-(9-bromo-2,3-dimethyl-naphtho2,3-b]thiophen-4-yl)-2-cyclopentyl-phenoxy]-3-phenyl-propionic acid Step 1

2-Bromo-4-(9-bromo-2,3-dimethyl-naphtho[2,3-b]thiophen-4-yl)-6-cyclopentyl-phenol To a suspension of 2-cyclopentyl-4-(9-bromo-2,3-dimethyl-naphtho[2,3-b]thiophen-4-yl)-phenol (2.0 g, 4.4 mmol) and potassium acetate (4.4 g, 44.3 mmol) in glacial acetic acid (60 mL) was added dropwise over a period of 17 minutes a solution of bromine (0.27 mL, 5.3 mmol) in glacial acetic acid (8 mL). The thick reaction mixture was diluted with glacial acetic acid (20 mL). After stirring at room temperature for 2 h the reaction mixture was poured into water (500 mL). The solution was extracted once with diethyl ether (250 mL), and then with diethyl ether (100 mL). The combined extracts were washed twice with water (100 mL). Concentration under reduced pressure and chromatography with petroleum ether:ethyl acetate (98:2), followed by trituation with petroleum ether gave the title compound as a white solid (1.2 g, 52%): mp 189.5–191° C.; (DMSO-d6): δ9.19 (s, 1H), 8.18 (d, 1H), 7.65–7.61 (m, 1H), 7.50–7.47 (m, 2H), 7.33 (d, 1H), 7.11 (d, 1H), 3.42 (quintet, 1H), 2.43 (s, 3H), 2.00–1.97 (m,2H), 1.69–1.46 (m, 6H), 1.60 (s, 3H); MS(EI): [M+], 2 bromine isotope pattern, 528 (46%), 530 (100%), 532 (52%); Anal. Calc. for C25H22Br2OS: C, 56.62; H, 4.18; N, 0.00. Found: C, 55.78; H, 4.12; N, 0.05.

Step 2

(2R)-2-[2-Bromo-4-(9-bromo-2,3-dimethyl-naphtho[2,3-b]thiophen-4yl)-6-cyclopentyl-phenoxy]-3-phenyl-propionic acid methyl ester To a solution of 2-bromo-4-(9-bromo-2,3-dimethyl-naphtho[2,3-b]thiophen-4-yl)-2,6-cyclopentyl-phenol (1.2 g, 2.2 mmol), (S)-2-hydroxy-3-phenylpropionic acid, methyl ester (0.60 g, 3.3 mmol), and triphenylphosphine (0.87 g, 3.3 mmol) in anhydrous benzene (20 mL) at room temperature under nitrogen was added dropwise diethylazodicarboxylate (0.52 mL, 3.3 mmol). After 5 h at room temperature the reaction mixture was adsorbed onto silica gel and chromatographed with petroleum ether:ethyl acetate (95:5) to yield the title compound as a white solid (1.2 g, 86%): mp 167–168.5° C.; NMR (CDCl3): δ8.28 (m, 1H), 7.58–7.47 (m, 2H), 7.41–7.36 (m, 2H), 7.34–7.25 (m, 5H), 7.18 (m, 1H), 5.11 and 5.02 (two dd, 1H, rotational isomers), 3.66 and 3.63 (two s, 3H, rotational isomers), 3.58–3.33 (m, 3H), 2.44 and 2.43 (two s, 3H, rotational isomers), 2.20 (m, 1H), 1.95 (m, 1H), 1.75–1.32 (m containing two singlets at δ1.63 and 1.69 (rotational isomers), 9H); MS(EI): [M+], 2 bromine isotope pattern, 690 (46%), 692 (100%), 694 (54%); Anal. Calc. for C35H32Br2O3S: C, 60.70; H, 4.66; N, 0.00. Found: C, 60.31; H, 4.64; N, 0.01.

Step 3

(2R)-2-[2-Bromo-4-(9-bromo-2,3-dimethyl-naphtho [2,3-b]thiophen-4-yl)-6-cyclopentyl-phenoxy]-3-phenyl-propionic acid To a solution of (2R)-2-[2-bromo-4-(9-bromo-2,3-dimethyl-naphtho[2,3-b]thiophen-4-yl)-6-cyclopentyl-phenoxy]-3-phenyl-propionic acid methyl ester (1.0 g, 1.5 mmol) in tetrahydrofuran (30 mL) and methanol (10 mL) at room temperature was added dropwise aqueous potassium hydroxide (3.0 mL of a 1 N solution, 3.0 mmol). After 4 h the reaction mixture was concentrated under reduced pressure. The residue was taken up in water (100 mL) and acidified with aqueous 10% hydrochloric acid. After stirring for 15 min the solid was filtered and washed with water-:methanol (95:5). The solid was dried under a vacuum at 50° C. for 18 h to yield the title compound as a white solid (0.99 g, 100%): Opt. Rot. [a]25/D=+38.44° (9.624 mg/mL, MeOH); NMR (DMSO-d6): δ13.01 (broad s, 1H), 8.19 (d, 1H), 7.67–7.62 (m, 1H), 7.54–7.22 (m, 9H), 4.92 (m, 1H), 3.46 (m, 1H), 3.34 (m, 2H), 2.42 and 2.41 (two singlets 3H, rotational isomers), 1.99 (m, 1H), 1.98 (m, 1H), 1.72–1.27 (m containing two s at δ1.57 and 1.53 (rotational isomers), 6H); MS(-ESI): [M-H], 2 bromine isotope pattern, 675 (72%), 677 (100%), 679 (66%); Anal. Calc. for C34H30Br2O3S: C, 60.19; H, 4.46; N, 0.00. Found: C, 59.53; H, 4.35; N, –0.04.

EXAMPLE 49

(R)-2-[4-(9-Bromo-2,3-dimethyl-naphtho[2,3-b] thiophen-4-yl)-2,6-dimethyl-phenoxy]-3-phenyl-propionic acid Step 1

(2-Benzyl-4,5-dimethyl-thiophen-3-yl)-(4-methoxy-3,5-dimethyl-phenyl)-methanone

To a suspension of 3,5-dimethyl-p-anisic acid (15.2 g, 84.4 mmol, RN-21553-46-8) in anhydrous methylene chloride (200 mL) at room temperature under nitrogen was added oxalyl chloride (9.6 mL, 110 mmol) and N,N-dimethylformamide (5 drops). After two hours the solvent was removed. The resulting residue was dissolved in anhydrous methylene chloride (200 mL), and added to 2,3-dimethyl-5-benzylthiophene (17.1 g, 84.4 mmol) under nitrogen. The resulting mixture was, cooled to –78° C., and tin(IV) chloride (10.8 mL, 92.8 mmol) was added quickly. The –78° C. bath was removed and the mixture was stirred at room temperature for 2 h. The reaction mixture was then poured onto ice water (1 L), and the resulting mixture was extracted once with diethyl ether (700 mL), and a second time with diethyl ether (400 mL). The combined diethyl ether extracts were washed with ice water (500 mL), dilute sodium bicarbonate (500 mL), water (500 mL), brine (1 L), and then dried (Na2SO4). Concentration under reduced pressure gave the title compound as a yellow oil (25.2 g, 82%): NMR (DMSO-d6): δ7.40 (s, 2H), 7.24–7.15 (m, 3H), 7.06 (d, 2H), 3.83 (s, 2H), 3.70 (s, 3H), 2.28 (s, 3H), 2.26 (s, 6H), 1.83 (s, 3H).

Step 2

4-(2,3-Dimethyl-naphtho[2,3-b]thiophen-4-yl)2,6-dimethyl-phenol (2-Benzyl-4,5-dimethyl-thiophen-3-yl)-(4-methoxy-3,5-dimethyl-phenyl)-methanone (25.2 g, 69.2 mmol) in anhydrous methylene chloride (420 mL) was placed under nitrogen and cooled to –78° C. Boron tribromide (20.9 mL, 221 mmol) was added dropwise over a period of 16 min, and the resulting mixture was stirred at –78C for 1.5 h. The –78° C. bath was removed and the reaction mixture was stirred at room temperature for 4 h. The reaction mixture was then poured onto ice water (1 L) containing some sodium bisulfite, and the resulting mixture was extracted once with diethyl ether (1 L), and a second time with diethyl ether (300 mL). The combined diethyl ether extracts were washed twice with water (1 L), brine (1 L), and then dried (Na2SO4). Concentration under reduced pressure afforded a dark residue which was combined with a second run done on (2-benzyl-4,5-dimethyl-thiophen-3-yl)-(4-methoxy-3,5-dimethyl-phenyl)-methanone (13.9 g, 38.1 mmol) and boron tribromide (11.5 mL, 122 mmol). Adsorption onto silica gel and chromatography with petroleum ether:ethyl acetate (90:10) gave a thick foamy amber residue identified as 2,6-dimethyl-4-(2,3-dimethyl-naphtho[2,3-b]thiophen-4-yl)-phenol (24.0 g, 67%): NMR (DMSO-d6): δ8.41 (s, 2H), 7.93 (d, 1H), 7.49–7.39 (m, 2H), 7.34–7.28 (m, 1H), 6.87 (s, 2H), 2.38 (s, 3H), 2.23 (s, 6H), 1.62 (s, 3H); MS(EI): [M+] 332.

Step 3

Acetic acid 4-(2,3-dimethyl-naphtho[2,3-b] thiophen-4-yl)-2,6-dimethyl-phenyl ester To a solution of 4-(2,3-dimethyl-naphtho[2,3-b]thiophen-4-yl)-2,6-dimethyl-phenol (24.0 g, 72.2 mmol) in pyridine (200 mL) at 0 C. under nitrogen was added dropwise acetic anhydride (8.9 mL, 93.9 mmol) over a period of 10 min. After 45 min at 0 C., the reaction mixture was placed in the freezer for 18 h, then removed and stirred for 2 h in an ice bath that was allowed to warm to room temperature. The reaction mixture was poured onto water (1 L) and acidified with 10% hydrochloric acid to a pH of 1. The resulting mixture was extracted with diethyl ether (1 L), which was washed with 10% hydrochloric acid (1 L), twice with water (1 L), brine (700 mL), and dried (MgSO4). Concentration under reduced pressure and chromatography with petroleum ether:ethyl acetate (97:3) gave the title compound as a cream solid (22.4 g, 79%): NMR (CDCl3): δ8.26 (s, 1H), 7.87 (d, 1H), 7.58 (d, 1H), 7.44–7.40 (m, 1H), 7.33–7.29 (m, 1H), 7.07 (s, 2H), 2.42 (s, 3H), 2.41 (s, 3H), 2.23 (s, 6H), 1.67 (s, 3H); MS(EI): [M+] 374; Anal. Calc. for C24H22O2S: C, 76.97; H, 5.92; N, 0.00. Found: C, 76.17; H, 5.75; N, 0.22.

Step 4

Acetic acid 4-(9-bromo-2,3-dimethyl-naphtho[2,3-b] thiophen-4-yl)-2,6-dimethyl-phenyl ester A solution of acetic acid 4-(2,3-dimethyl-naphtho[2,3-b] thiophen-4-yl)-2,6-dimethyl-phenyl ester (10.0 g, 26.7 mmol) and ferric chloride (0.23 g, 1.4 mmol) in anhydrous methylene chloride (231 mL) was placed at –78 C. under nitrogen. The reaction mixture was protected from light and a solution of bromine (1.5 mL, 29.4 mmol) in anhydrous methylene chloride (38 mL) was added dropwise over a period of 50 min. After 30 min the reaction was quenched with dilute sodium bisulfite, diluted with water, and the resulting mixture was extracted with diethyl ether. The diethyl ether layer was washed twice with water, brine, and then dried (MgSO4). Concentration under reduced pressure and chromatography with petroleum ether:ethyl acetate (97:3, then 95:5) gave the title compound as a white solid (6.7 g, 55%): NMR (DMSO-d6): δ8.27 (d, 1H), 7.60 (d, 1H), 7.56–7.52 (ddd, 1H), 7.38–7.34 (ddd, 1H), 7.06 (s, 2H), 2.43 (s, 3H), 2.41 (s, 3H), 2.22 (s, 6H), 1.64 (s, 3H); MS(EI): [M+], 1 bromine isotope pattern, 452/454; Anal. Calc. for C24H21BrO2S: C, 63.58; H, 4.67; N, 0.00. Found: C, 63.41; H, 4.45; N, 0.08.

Step 5

4-(9-Bromo-2,3-dimethyl-naphtho[2,3-b]thiophen-4-yl)-2,6-dimethyl-phenol

To a solution of acetic acid 4-(9-bromo-2,3-dimethyl-naphtho[2,3-b]thiophen-4-yl)-2,6-dimethyl-phenyl ester (6.5 g, 14.3 mmol) in tetrahydrofuran (240 mL) and methanol (80 mL) at room temperature was added dropwise aqueous potassium hydroxide (17.2 mL of a 1N solution, 17.2 mmol). After 4 h at room temperature the reaction mixture was placed in the freezer for 18 h. The reaction was removed from the freezer and allowed to stir at room temperature. More aqueous potassium hydroxide (41.5 mL of a 1N solution, 41.5 mmol), tetrahydrofuran (50 mL), and methanol (10 mL) were added. The mixture was diluted with water (500 mL), acidified with 1N aqueous solution of hydrochloric acid, and extracted with diethyl ether. The diethyl ether layer was washed twice with water (500 mL), and dried (MgSO4). Concentration under reduced pressure gave a residue which was adsorbed onto silica gel. Chromatography with petroleum ether:ethyl acetate (97:3, then 95:5) gave the title compound as a white foamy solid (5.5 g, 93%): NMR (CDCl3): δ8.41 (s, 1H), 8.16 (d, 1H), 7.64–7.54 (m, 2H), 7.46–7.40 (m, 1H), 6.89 (s, 2H), 2.41 (s, 3H), 2.23 (s, 6H), 1.60 (s, 3H); MS(-ESI): [M-H], 1 bromine isotope pattern, 409/411.

Step 6

(2R)-2-[4-(9-bromo-2,3-dimethyl-naphtho[2,3-b]thiophen-4-yl)-2,6-dimethyl-phenoxy]3-phenyl-propionic acid methyl ester To a solution of 4-(9-bromo-2,3-dimethyl-naphtho[2,3-b]thiophen-4-yl)-2,6-dimethyl-phenol (5.0 g, 12.1 mmol), (S)-2-hydroxy-3-phenylpropionic acid, methyl ester (3.3 g, 18.3 mmol), and triphenylphosphine (4.8 g, 18.3 mmol) in anhydrous benzene (50 mL) at room temperature under nitrogen was added dropwise diethyl azodicarboxylate (2.6 mL, 18.3 mmol) over a period of 25 min. The reaction mixture was heated for 2 h, then stirred at room temperature for 3 days. The crude reaction mixture was adsorbed onto silica gel and chromatographed twice with petroleum ether:ethyl acetate (95:5) to yield the title compound as a white foamy solid (4.5 g, 65%): NMR (DMSO-d6): δ8.18 (d, 1H), 7.64 (ddd, 1H), 7.53–7.43 (m, 2H), 7.38–7.24 (m, 5H), 7.00 (s, 2H), 4.80 (t, 1H), 3.58 (s, 3H), 3.31 (m, 2H), 2.42 (s, 3H), 2.24 (s, 3H), 2.19 (s, 3H), 1.55 (s, 3H); MS(EI): [M+], 1 bromine isotope pattern, 572/574; Anal. Calc. for C32H29BrO3S: C, 67.01; H, 5.10; N, 0.00. Found: C, 66.33; H, 5.09; N, 0.09; Analytical HPLC indicates a major component (94.39%).

Step 7

(2R)-2-[4-(9-bromo-2,3-dimethyl-naphtho[2,3-b]thiophen-4-yl)-2,6-dimethyl-phenoxy]-3-phenyl-propionic acid To a solution of (2R)-2-[4-(9-bromo-2,3-dimethyl-naphtho[2,3-b]thiophen-4-yl)-2,6-dimethyl-phenoxy]-3-phenyl-propionic acid methyl ester (3.1 g, 5.4 mmol) in tetrahydrofuran (125 mL) and methanol (41 mL) at room temperature was added dropwise aqueous potassium hydroxide (6.5 mL of a 1N solution, 6.5 mmol). After 1.5 h at room temperature the reaction mixture was placed in the freezer for 18 h. The reaction was removed from the freezer and allowed to stir at room temperature. More aqueous potassium hydroxide (19.5 mL of a 1N solution, 19.5 mmol) was added, and the reaction mixture was allowed to stir at room temperature for 9.5 h. Concentration under reduced pressure gave a residue which was diluted with water (1 L). The aqueous layer was acidified with concentrated hydrochloric acid to a pH of 1, and extracted with diethyl ether (700 mL). The diethyl ether layer was washed twice with water (500 mL), and then dried (Na2SO4). Concentration under reduced pressure and chromatography on silica gel (treated with 2% phosphoric acid in methanol) with petroleum ether:ethyl acetate (90:10, then 86:14) gave the title compound as a white solid foam (1.9 g, 64%): Opt. Rot. [a]25/D=+33.38° (10.035 mg/mL, MeOH); NMR (DMSO-d6): δ12.90 (broad singlet, 1H), 8.17 (d, 1H), 7.63 (ddd, 1H), 7.50–7.43 (m, 2H), 7.36–7.23 (m, 5H), 6.97 (s, 2H), 4.71 (t, 1H), 3.25 (d, 2H), 2.41 (s, 3H), 2.24 (s, 3H), 2.21 (s, 3H), 1.54 (s, 3H); MS(EI): [M+], 1 bromine isotope pattern, 558/560; Anal. Calc. for C31H27BrO3S: C, 66.55; H, 4.86; N, 0.00. Found: C, 65.91; H, 5.05; N, 0.09; Analytical HPLC indicates a major component (99.5%).

EXAMPLE 50

(R)-2-[4-(2,3-Dimethyl-naphtho[2,3-b]thiophen-4-yl)-2,6-diisopropyl-phenoxy]-3-phenyl-propionic acid Step 1

(2-Benzyl-4,5-dimethyl-thiophen-3-yl)-(3,5-diisopropyl-4-methoxy-phenyl)-methanone In a manner similar to the procedure of Example 49, Step 1, there was obtained from 3,5-diisopropyl-p-anisic acid (5.0 g, 21.2 mmol, RN-117439-59-5), oxalyl chloride (2.2 mL, 25.4 mmol), N,N-dimethylformamide (2 drops), 2,3-dimethyl-5-benzylthiophene (4.3 g, 21.2 mmol), tin(IV) chloride (5.0 mL, 42.7 mmol), and anhydrous methylene chloride (82 mL) the title compound as a yellow oil (4.1 g, 45%): NMR (DMSO-d6): δ7.47 (s, 2H), 7.23–7.12 (m, 3H), 7.02–6.99 (m, 2H), 3.86 (s, 2H), 3.73 (s, 3H), 3.31–3.20 (m, 2H), 2.27 (s, 3H), 1.82 (s, 3H), 1.15 (d, 12H); MS(EI): [M+] 420.

Step 2

2,6-Diisopropyl-4-(2,3-dimethyl-naphtho[2,3-b]thiophen-4-yl)-phenol

In a manner similar to the procedure of Example 49, Step 2, there was obtained from (2-benzyl-4,5-dimethyl-thiophen-3-yl)-(3,5-diisopropyl-4-methoxy-phenyl)-methanone (4.3 g, 10.1 mmol), boron tribromide (3.1 mL, 32.4 mmol), and methylene chloride (60 mL) the title compound as a yellow foam (1.2 g, 30%): NMR (DMSO-d6): δ8.42 (s, 1H), 8.24 (s, 1H), 7.94 (d, 1H), 7.48–7.32 (m, 3H), 6.90 (s, 2H), 3.45–3.35 (m, 2H), 2.38 (s, 3H), 1.57 (s, 3H), 1.15 (d, 12H); MS(-ESI): [M-H] 387.

Step 3

(2R)-2-[4-(2,3-Dimethyl-naphtho[2,3-b]thiophen-4-yl)-2,6-diisopropyl-phenoxy]-3-phenyl-propionic acid methyl ester In a manner similar to the procedure of Example 49, Step 6, there was obtained from 4-(2,3-dimethyl-naphtho[2,3-b]thiophen-4-yl)-2-isopropyl-phenol (0.33 g, 0.84 mmol), (S)-

2-hydroxy-3-phenylpropionic acid, methyl ester (1.5 g, 8.3 mmol), triphenylphosphine (2.2 g, 8.3 mmol), diethylazodicarboxylate (1.3 mL, 8.3 mmol), and anhydrous benzene (9.0 mL) in an oil bath (85° C.) for 18 h the title compound as an oil (0.11 g, 24%): NMR (DMSO-d6): δ8.45 (s, 1H), 7.96 (d, 1H), 7.50–7.25 (m, 8H), 7.03 (s, 2H), 4.54 (t, 1H), 3.56 (s, 3H), 3.40–3.18 (m, 4H), 2.38 (s, 3H), 1.51 (s 3H), 1.14 and 1.13 (two doublets, 6H, rotational isomers), 1.07 and 1.04 (two doublets, 6H, rotational isomers); MS(EI): [M+] 550.

Step 4

(2R)-2-[4-(2,3-Dimethyl-naphtho[2,3-b]thiophen-4-yl)-2,6-diisopropyl-phenoxy]-3-phenyl-propionic acid In a manner similar to the procedure of Example 49, Step 7, there was obtained from (2R)-2-[4-(2,3-dimethyl-naphtho[2,3-b]thiophen-4-yl)-2,6-diisopropyl-phenoxy]-3-phenyl-propionic acid methyl ester (0.11 g, 0.20 mmol), aqueous potassium hydroxide (0.39 mL of a 1 N solution, 0.39 mmol), tetrahydrofuran (3 mL), and methanol (1 mL) the title compound as a white solid (0.10 g, 98%): NMR (DMSO-d6): δ12.97 (broad s, 1H), 8.46 (s, 1H), 7.96 (d, 1H), 7.47–7.25 (m, 8H), 7.04 (s, 2H), 4.47 (t, 1H), 3.41–3.30 (m, 2H), 3.28–3.23 (m, 2H), 2.40 (s, 3H), 1.53 (s, 3H), 1.15 (d, 6H), 1.08 (d, 6H); MS(EI): [M+] 536; Anal. Calc. for C35H36O3S: C, 78.32; H, 6.76; N, 0.00. Found: C, 77.12; H, 6.86; N, −0.11; Analytical HPLC indicates a major component (93.2%).

EXAMPLE 51

(R)-2-[4-(2,3-Dimethyl-naphtho[2,3-b]thiophen-4-yl)-2-fluoro-phenoxy]-3-phenyl-propionic acid Step 1

(2-Benzyl-4,5-dimethyl-thiophen-3-yl)-(3-fluoro-4-methoxy-phenyl)-methanone

In a manner similar to the procedure of Example 49, Step 1, there was obtained from 3-fluoro-p-anisic acid (10.0 g, 58.8 mmol), oxalyl chloride (6.2 mL, 71.0 mmol), N,N-dimethylformamide (12 drops), 2,3-dimethyl-5-benzylthiophene (11.9 g, 58.8 mmol), tin(IV) chloride (10.3 mL, 88.0 mmol), and anhydrous methylene chloride (130 mL) the title compound as a yellow solid (7.53 g, 68%): MS(+ESI): [M+H] 355; Anal. Calc. for C21H19FO2S: C, 71.16; H, 5.40; N, 0.00. Found: C, 70.01; H, 5.43; N, −0.06.

Step 2

2-Fluoro-4-(2,3-dimethyl-naphtho[2,3-b]thiophen-4-yl)-phenol

In a manner similar to the procedure of Example 49, Step 2, there was obtained from (2-benzyl-4,5-dimethyl-thiophen-3-yl)-(3-fluoro-4-methoxy-phenyl)-methanone (7.5 g, 21.2 mmol), boron tribromide (7.0 mL, 74.3 mmol), and methylene chloride (88 mL) the title compound as a yellow foam (6.7 g, 99%): MS(EI): [M+] 322; Anal. Calc. for C20H15FOS: C, 74.51; H, 4.69; N, 0.00. Found: C, 73.96; H, 4.94; N, −0.08.

Step 3

(2R)-2-[4-(9-Bromo-2,3-dimethyl-naphtho[2,3-b]thiophen-4-yl)-2-fluoro-phenoxy]-3-phenyl-propionic acid In a manner similar to the procedure of Example 49, Step 6, there was obtained from 2-fluoro-4-(2,3-dimethyl-naphtho[2,3-b]thiophen-4-yl)-phenol (1.0 g, 3.1 mmol), (S)-2-hydroxy-3-phenylpropionic acid, methyl ester (0.67 g, 3.7 mmol), triphenylphosphine (0.98 g, 3.7 mmol), diethylazodicarboxylate (0.59 mL, 3.7 mmol), and anhydrous benzene (20 mL) in an oil bath (85° C.) for 5 h the title compound as a white solid (0.86 g), which was used without further purification.

In a manner similar to the procedure of Example 49, Step 7, there was obtained from (2R)-2-[4-(9-bromo-2,3-dimethyl-naphtho[2,3-b]thiophen-4-yl)-2-fluoro-phenoxy]-3-phenyl-propionic acid methyl ester (0.86 g, 1.8 mmol), aqueous potassium hydroxide (3.6 mL of a 1 N solution, 3.6 mmol), tetrahydrofuran (12 mL), and methanol (4 mL) the title compound as a white solid (0.41 g, 63%): Opt. Rot. [a]25/D=+0.870 (11.473 mg/mL, MeOH); MS(EI): [M+] 470; Anal. Calc. for C29H23FO3S: C, 74.02; H, 4.93; N, 0.00. Found: C, 73.95; H, 5.22; N, 0.12.

EXAMPLE 52

(R)-2-[4-(9-Bromo-2,3-dimethyl-naphtho[2,3-b]thiophen-4-yl)-2-fluoro-phenoxy]-3-phenyl-propionic acid Step 1

Acetic acid 2-fluoro-4-(9-bromo-2,3-dimethyl-naphtho[2,3-b]thiophen-4-yl)-phenyl ester In a manner similar to the procedure of Example 49, Step 3, there was obtained from 2-fluoro-4-(2,3-dimethyl-naphtho[2,3-b]thiophen-4-yl)-phenol (1.0 g, 3.1 mmol), acetic anhydride (0.36 mL, 3.8 mmol), and pyridine (7.5 mL) a yellow solid (1.1 g), which was used without further purification.

In a manner similar to the procedure of Example 49, Step 4, there was obtained from acetic acid 2-fluoro-4-(2,3-dimethyl-naphtho[2,3-b]thiophen-4-yl)-phenyl ester (1.1 g, 2.9 mmol), ferric chloride (24.8 mg, 0.15 mmol), bromine (0.16 mL, 3.2 mmol), and methylene chloride (12 mL) the title compound as a yellow oil (0.86 g, 67%): MS(EI): [M+], 1 bromine isotope pattern, 442/444.

Step 2

2-Fluoro-4-(9-bromo-2,3-dimethyl-naphtho[2,3-b]thiophen-4-yl)-phenol

In a manner similar to the procedure of Example 49, Step 5, there was obtained from acetic acid 2-fluoro-4-(9-bromo-2,3-dimethyl-naphtho[2,3-b]thiophen-4-yl)-phenyl ester (0.29 g, 0.65 mmol), aqueous potassium hydroxide (0.79 mL of a 1 N solution, 0.79 mmol), tetrahydrofuran (12 mL), and methanol (7.5 mL) there was obtained the title compound as an off-white solid (0.3 g, 100%): MS(EI): [M+], 1 bromine isotope pattern, 400/402.

Step 3

(R)-2-[4-(9-Bromo-2,3-dimethyl-naphtho[2,3-b]thiophen-4-yl)-2-fluoro-phenoxy]-3-phenyl-propionic acid methyl ester In a manner similar to the procedure of Example 49, Step 6, there was obtained from 2-Fluoro-4-(9-bromo-2,3-dimethyl-naphtho[2,3-b]thiophen-4-yl)-phenol (0.29 g, 0.72 mmol), (S)-2-hydroxy-3-phenylpropionic acid, methyl ester (0.19 g, 1.1 mmol), triphenylphosphine (0.28 g, 1.1 mmol), diethylazodicarboxylate (0.17 mL, 1.1 mmol), and anhydrous benzene (5.0 mL) the title compound as a white solid (0.23 g, 58%): MS(EI): [M+], 1 bromine isotope pattern, 562/564.

Step 4

(R)-2-[4-(9-Bromo-2,3-dimethyl-naphtho[2,3-b]thiophen-4-yl)-2-fluoro-phenoxy]-3-phenyl-propionic acid In a manner similar to the procedure of Example 49, Step 7, there was obtained from (R)-2-[4-(9-bromo-2,3-dimethylnaphtho[2,3-b]thiophen-4-yl)-2-fluoro-phenoxy]-3-phenyl-propionic acid methyl ester (0.23 g, 0.41 mmol), aqueous potassium hydroxide (0.50 mL of a 1 N solution, 0.50 mmol), tetrahydrofuran (6 mL), and methanol (2 mL) the title compound as a white solid (0.17 g, 74%): MS(EI): [M+], 1 bromine isotope pattern, 548/550; Anal. Calc. for C29H22BrFO3S: C, 63.39; H,4.04; N, 0.00. Found: C, 62.14; H, 4.29; N, 0.16; Analytical HPLC indicates a major component (82.5%).

EXAMPLE 53

[4-(9-Bromo-2,3-dimethyl-naphtho[2,3-b]thiophen-4-yl)-2,6-diisopropyl-phenoxy]-acetic acid Step 1

Acetic acid 4-(2,3-dimethyl-naphtho[2,3-b]thiophen-4-yl)-2,6-diisopropyl-phenyl ester In a manner similar to the procedure of Example 49, Step 3, there was obtained from 4-(2,3-dimethyl-naphtho[2,3-b]thiophen-4-yl)-2,6-diisopropyl-phenol (5.0 g, 13.7 mmol), acetic anhydride (1.68 mL, 17.8 mmol), and pyridine (85 mL) the title compound as a white solid (5.37 g, 91%): mp 243–245° C.; NMR (DMSO-d6): δ8.49 (s, 1H), 7.98 (d, 1H), 7.49–7.39 (m, 3H), 7.16 (s, 2H), 3.01 (septet, 2H), 2.43 (s, 3H), 2.41 (s, 3H), 1.56 (s, 3H), 1.16 (d, 12H); MS(EI): [M+] 430; Anal. Calc. for C28H30O2S: C, 78.10; H, 7.02; N, 0.00. Found: C, 77.95; H, 7.04; N, 0.07; Analytical HPLC indicates a major component (99.3%).

Step 2

Acetic acid 4-(9-bromo-2,3-dimethyl-naphtho[2,3-b]thiophen-4-yl)-2,6-diisopropyl-phenyl ester In a manner similar to the procedure of Example 49, Step 4, there was obtained from acetic acid 4-(2,3-dimethyl-naphtho[2,3-b]thiophen-4-yl)-2,6-diisopropyl-phenyl ester (0.80 g, 18.5 mmol), ferric chloride (16 mg, 0.1 mmol), bromine (0.13 mL, 2.6 mmol), and methylene chloride (19 mL) the title compound as a white solid (0.53 g, 56%): NMR (DMSO-d6): δ8.21 (d, 1H), 7.68–7.62 (m, 1H), 7.60–7.42 (m, 2H), 7.18 (s, 2H), 3.00 (septet, 2H), 2.42 (s, 6H), 1.53 (s, 3H), 1.14 (d, 12H).

Step 3

4-(9-Bromo-2,3-dimethyl-naphtho[2,3-b]thiophen-4-yl)-2,6-diisopropyl-phenol

In a manner similar to the procedure of Example 49, Step 5, there was obtained from acetic acid 4-(9-bromo-2,3-dimethyl-naphtho[2,3-b]thiophen-4-yl)-2,6-diisopropyl-phenyl ester (0.52 g, 1.0 mmol), aqueous potassium hydroxide (1.64 mL of a 1 N solution, 1.6 mmol), tetrahydrofuran (18.5 mL), and methanol (11.5 mL) there was obtained the title compound as a cream solid (0.45 g, 95%): mp 212–216° C.; NMR (DMSO-d6): δ8.30 (s, 1H), 8.17 (d, 1H), 7.61 (ddd, 1H), 7.53 (d, 1H), 7.44 (ddd, 1H), 6.92 (s, 2H ), 3.41 (septet, 2H), 2.41 (s, 3H), 1.55 (s, 3H), 1.15 (d, 12H); MS(EI): [M+], 1 bromine isotope pattern, 466/468; Anal. Calc. for C26H27BrOS: C, 66.80; H, 5.82; N, 0.00. Found: C, 66.17; H, 5.63; N, 0.06.

Step 4

[4-(9-Bromo-2,3-dimethyl-naphtho[2,3-b]thiophen-4-yl)-2. 6-diisopropyl-phenoxy]-acetic acid methyl ester A solution of 4-(9-bromo-2,3-dimethyl-naphtho[2,3-b]thiophen-4-yl)-2,6-diisopropyl-phenol (0.42 g, 0.89 mmol), methyl bromoacetate (0.36 mL, 3.8 mmol), and potassium carbonate (0.42 g, 3.0 mmol) in anhydrous N,N-dimethylformamide (3.5 mL) at room temperature under nitrogen was stirred for 2 days. The reaction mixture was diluted with water and extracted with diethyl ether. Concentration under reduced pressure and chromatography with petroleum ether:ethyl acetate (95:5) gave the title compound as a white solid (0.42 g, 87%): NMR (DMSO-d6): δ8.20 (d, 1H), 7.66–7.61 (m, 1H), 7.48 (d, 2H), 7.11 (s, 2H), 4.56 (s, 2H), 3.77 (s, 3H), 3.42–3.27 (m, 2H), 2.42 (s, 3H), 1.51 (s, 3H), 1.18 and 1.16 (two doublets, 12H).

Step 5

[4-(9-Bromo-2,3-dimethyl-naphtho[2,3-b]thiophen-4-yl)-2,6-diisopropyl-phenoxy]-acetic acid In a manner similar to the procedure of Example 49, Step 7, there was obtained from [4-(9-bromo-2,3-dimethyl-naphtho[2,3-b]thiophen-4-yl)-2,6-diisopropyl-phenoxy]-acetic acid methyl ester (0.40 g, 0.74 mmol), aqueous potassium hydroxide (0.89 mL of a 1 N solution, 0.89 mmol), tetrahydrofuran (6 mL), and methanol (2 mL) the title compound as a white solid (0.37 g, 95%): mp 228–231° C. NMR (DMSO-d6): δ12.98 (broad s, 1H), 8.19 (d, 1H), 7.65–7.61 (m,1H), 7.47 (d, 2H), 7.10 (s, 2H), 4.44 (s, 2H), 3.40 (septet, 2H), 2.41 (s, 3H), 1.51 (s, 3H), 1.18 and 1.16 (two doublets, 12H); MS(EI): [M+], 1 bromine isotope pattern, 524/526; Anal. Calc. for C28H29BrO3S: C, 64.00; H, 5.56; N, 0.00. Found: C, 63.32, H, 5.39; N, 0.01; Analytical HPLC indicates a major component (96%).

EXAMPLE 54

(2R)-2-[2,6-Dibromo-4-(2,3-dimethyl-naphtho[2,3-b]furan-4-yl)-phenoxy]-3-phenyl-propionic acid Step 1

(2-Benzyl-4,5-dimethyl-furan-3-yl)-(4-methoxy-3,5-dibromo-phenyl)-methanone

In a manner similar to the procedure of Example 49, Step 1, there was obtained from 3,5-dibromo-p-anisic acid (8.0 g, 25.8 mmol), oxalyl chloride (2.48 mL, 28.4 mmol), N,N-dimethylformamide (2 drops), 2,3-dimethyl-5-benzylfuran (5.77 g, 31.0 mmol), tin(IV) chloride (3.30 mL, 28.4 mmol), and anhydrous methylene chloride (165 mL) the title compound as a solid (2.92 g, 24%): (DMSO-d6): δ7.81 (s, 2H), 7.28–7.14 (m, 3H), 7.04 (d, 2H), 3.86 (s, 3H), 3.84 (s, 2H), 2.19 (s, 3H), 1.81 (s, 3H); MS(EI): [M+], 2 bromine isotope pattern, 476 (25%), 478 (50%), 480(25%).

Step 2

4-(2,3-Dimethyl-naphtho[2,3-b]furan-4-yl)-2,6-dibromo-phenol

In a manner similar to the procedure of Example 49, Step 2, there was obtained from (2-benzyl-4,5-dimethyl-furan-3-yl)-(4-methoxy-3,5-dibromo-phenyl)-methanone (2.52 g, 5.30 mmol), boron tribromide (3.79 mL, 40.0 mmol), and methylene chloride (18 mL) the title compound (0.93 g), which was used without further purification: (DMSO-d6): δ10.19 (br s, 1H), 8.01 (d, 1H), 7.98 (s, 1H), 7.56 (s, 2H), 7.51 (d, 1H), 7.44 (ddd, 1H), 7.36 (ddd, 1H), 2.39 (s, 3H), 1.62 (s, 3H); MS(-ESI): [M–H], 2 bromine isotope pattern, 443 (63%), 445 (100%), 447 (63%).

Step 3

(2R)-2-[2,6-Dibromo-4-(2,3-dimethyl-naphtho[2,3-b]furan-4-yl)-phenoxy]-3-phenyl-propionic acid methyl ester In a manner similar to the procedure of Example 49, Step 6, there was obtained from 4-(9-bromo-2,3-dimethyl-naphtho[2,3-b]furan-4-yl)-2,6-dibromo-phenol (0.88 g, 1.97 mmol), (S)-2-hydroxy-3-phenylpropionic acid, methyl ester (0.71 g, 3.94 mmol), triphenylphosphine (1.03 g, 3.94 mmol), diethylazodicarboxylate (0.62 mL, 3.94 mmol), and anhydrous benzene (3.9 mL) at room temperature the title compound as a solid (1.15 g, 96%): NMR (DMSO-d6): δ8.04 (d, 1H), 8.03 (s, 1H), 7.71 (s, 2H), 7.51–7.24 (m, 8H), 5.11 (dd, 1H), 3.63 (s, 3H), 3.53–3.35 (two overlapping quartets, ABX pattern, 2H), 2.41 (s, 3H), 1.60 (s, 3H); MS(EI): [M+], 2 bromine isotope pattern, 606 (52%), 608 (100%), 610 (52%).

Step 4

(2R)-2-[2,6-Dibromo-4-(2,3-dimethyl-naphtho[2,3-b]furan-4-yl)-phenoxy]-3-phenyl-propionic acid In a manner similar to the procedure of Example 49, Step 7, there was obtained from (2R)-2-[2,6-dibromo-4-(2,3-dimethyl-naphtho[2,3-b]furan-4-yl)-phenoxy]-3-phenyl-propionic acid methyl ester (0.25 g, 0.41 mmol), aqueous potassium hydroxide (0.82 mL of a 1 N solution, 0.82 mmol), tetrahydrofuran (3.0 mL), and methanol (1.0 mL) the title compound as a white solid (0.24 g, 100%): NMR (DMSO-d6): δ13.11 (br s, 1H), 8.02 (d, 1H), 8.01 (s, 1H), 7.66 (s, 2H), 7.49–7.21 (m, 8H), 5.19 (t, 1H), 3.36 (d, 2H), 2.39 (s, 3H), 1.58 (s, 3H); MS(EI): [M+], 2 bromine isotope pattern, 592 (50%), 594 (100%), 596 (50%); Anal. Calc. for C29H22Br2O4: C, 58.61; H, 3.73; N, 0.00. Found: C, 58.52; H, 4.01; N, 0.05.

EXAMPLE 55

(2R)-2-[4-(9-Bromo-2,3-dimethyl-naphtho[2,3-b]thiophen-4-yl)-2,6-diisopropyl-phenoxy]-3-phenyl-propionic acid Step 1

(2R)-2-[4-(9-bromo-2,3-dimethyl-naphtho[2,3-b]thiophen-4-yl)-2,6-diisopropyl-phenoxy]-3-phenyl-propionic acid methyl ester In a manner similar to the procedure of Example 49, Step 6, there was obtained from 4-(9-bromo-2,3-dimethyl-naphtho[2,3-b]thiophen-4-yl)-2,6-diisopropyl-phenol (0.46 g, 0.98 mmol), (S)-2-hydroxy-3-phenylpropionic acid, methyl ester (0.70 g, 3.9 mmol), triphenylphosphine (1.02 g, 3.9 mmol), diethylazodicarboxylate (0.62 mL, 3.9 mmol), and anhydrous benzene (1.0 mL) in an oil bath (90° C.) for 24 h the title compound as a white solid (0.20 g, 32%): NMR (DMSO-d6): δ8.19 (d, 1H), 7.65–7.60 (m, 1H), 7.50–7.40 (m, 2H), 7.38–7.27 (m, 5H), 7.06 (s, 2H), 4.55 (t, 1H), 3.55 (s, 3H), 3.35–3.19 (m, 4H), 2.41 (s, 3H), 1.49 (s, 3H), 1.13 (d, 6H), 1.06 and 1.04 (two doublets, 6H, rotational isomers).

Step 2

(2R)-2-[4-(9-Bromo-2,3-dimethyl-naphtho[2,3-b]thiophen-4-yl)-2,6-diisopropyl-phenoxy]-3-phenyl-propionic acid In a manner similar to the procedure of Example 49, Step 7, there was obtained from (2R)-2-[4-(9-bromo-2,3-dimethyl-naphtho[2,3-b]thiophen-4-yl)-2,6-diisopropyl-phenoxy]-3-phenyl-propionic acid methyl ester (0.20 g, 0.31 mmol), aqueous potassium hydroxide (1.2 mL of a 1 N solution, 1.2 mmol), tetrahydrofuran (3 mL), and methanol (1 mL) the title compound as a white solid (0.18 g, 93%): mp 222–226° C.; NMR (DMSO-d6): δ13.0 (broad s, 1H), 8.20 (d, 1H), 7.64 (ddd, 1H), 7.48–7.46 (m, 2H), 7.38–7.27 (m, 5H), 7.06 (s, 2H), 4.48 (t, 1H), 3.40–3.26 (m, 4H), 2.42 (s, 3H), 1.50 (s, 3H), 1.14 (d, 6H), 1.07 (d, 6H); MS(−ESI): [M−H], 1 bromine isotope pattern, 558/560; Anal. Calc. for C35H35BrO3S: C, 68.28; H, 5.73; N, 0.00. Found: C, 68.15; H, 5.83; N, 0.03; Analytical HPLC indicates a major component (100%).

EXAMPLE 56

[3-Bromo-5-(9-bromo-2,3-dimethyl-naphtho[2,3-b]thiophen-4-yl)-2-hydroxy-phenyl]-carbamic Acid tert-Butyl Ester A solution of 2-amino-6-bromo-4-(9-bromo-2,3-dimethyl-naphtho[2,3-b]thiophen-4-yl)-phenol (0.382 g, 0.801 mmol) and di-t-butyl dicarbonate (0.191 g, 0.875 mmol) in THF (0.83 mL) was heated at 70° C. for 15 h. The reaction mixture was diluted with ether and silica gel was added. The ether was removed and the adsorbate was flash chromatographed (9:1 pet. ether: ethyl acetate) to provide the title compound as a white solid (0.447 g, 97%): mp 205–207° C.: NMR (DMSO-d6); 9.61 (s, 1H), 8.55 (2, 1H). 8.19 (d, J=8 Hz, 1H), 7.65 (ddd, J=8, 6, 2 Hz, 1H), 7.52–7.46 (m, 3 H), 7.27 (d, J=2 Hz, 1H), 2.44 (d, J=1 Hz, 3H), 1.67 (d, J=1 Hz, 3H), 1.40 (s, 9 H); MS (EI): 2 bromine isotope pattern 575 (20%, M+), 577 (50%, M+), 579 (20%, M+), 519 (50%, M+H-tBu), 521 (100%, M+H-tBu), 523 (55%, M+H-tBu); Anal. Calc. for C25H23Br2NO3S: C, 52.01; H, 4.02; N, 2.43. Found: C, 51.09; H, 3.84; N, 2.28.

EXAMPLE 57

9-Bromo-4-(3-bromo-methoxy-5-nitro-phenyl)-2,3-dimethyl-naphtho[2,3-b]thiophene

Iodomethane (0.22 mL, 3.55 mmol) and potassium carbonate (0.490 g, 3.55 mmol) were added to a stirred, room temperature solution of 9-bromo-4-(3-bromo-methoxy-5-nitro-phenyl)-2,3-dimethyl-naphtho[2,3-b]thiophene (0.600 g, 1.183 mmol) in DMF (8 mL). After 7 h, more iodomethane (0.1 mL, 1.61 mmol) was added and the suspension was stirred an additional 17 h. The reaction mixture was added to water and ectracted with ether. Silica gel was added. The ether was removed and the adsorbate was flash chromatographed (95:5 pet. ether: ethyl acetate) to provide the title compound as a yellow solid (0.416 g, 67%): mp 204–205° C.: NMR (DMSO-d6); 8.23 (d, J=8 Hz, 1H), 8.33 (d, J=2 Hz, 1H), 8.04 (d, J=2 Hz, 1H), 7.69 (ddd, J=8, 6, 1 Hz, 1H), 7.53 (ddd, J=8, 6, 1 Hz, 1H), 7.47 (d, J=8 Hz, 1H), 4.05 (s, 3H), 2.45 (d, J=1 Hz, 3H), 1.62 (d, J=1 Hz, 3H); MS (FAB+): 2 bromine isotope pattern 519, 521, 523; Anal. Calc. for C21H15Br2NO3S: C, 48.39; H, 2.90; N, 2.69. Found: C, 48.16; H, 2.69; N, 2.58.

EXAMPLE 58

3-Bromo-5-(9-bromo-2,3-dimethyl-naphtho[2,3-b]thiophen-4-yl)-2-methoxy-phenylamine A stirred suspension of 9-bromo-4-(3-bromo-methoxy-5-nitro-phenyl)-2,3-dimethyl-naphtho[2,3-b]thiophene (0.372, 0.714 mmol), tin (II) dichloride (805 mg, 3.57 mmol) and ethyl acetate (4 mL)was heated to 70° C. where disolution occurred. After 30 min, the reaction mixture was cooled to room temperature, diluted with ethyl acetate and silica gel was added. The ethyl acetate was removed and the adsorbate was flash chromatographed (4:1 pet. ether: ethyl acetate) to provide the title compound as a white solid (0.324 g, 92%): mp 198–200° C.: NMR (DMSO-d6); 8.18 (d, J=8 Hz, 1H), 7.64 (ddd, J=8, 6, 1 Hz, 1H), 7.58 (d, J=8 Hz, 1H), 7.50 (ddd, J=8, 6, 1 Hz, 1H), 6.70 (d, J=2 Hz, 1H), 6.64 (d, J=2 Hz, 1H), 5.46 (s, 1H), 3.80 (s, 3H), 2.44 (d,J=1 Hz, 3H), 1.73 (d, J=1 Hz, 3H); MS (EI): 2 bromine isotope pattern 489 (50%, M+), 491 (100%, M+), 493 (60%, M+); Anal. Calc. for C21H17Br2NOS: C, 51.34; H, 3.49; N, 2.85. Found: C, 51.00; H, 3.43; N, 2.71.

EXAMPLE 59

[3-Bromo-5-(9-bromo-2,3-dimethyl-naphtho[2,3-b]thiophen-4-yl)-2-methoxy-phenylamino]-acetic Acid Methyl Ester Methyl bromoacetate (0.285 mL, 3.01 mmol) was added to a stirred, room temperature suspension of 3-bromo-5-(9-bromo-2,3-dimethyl-naphtho[2,3-b]thiophen-4-yl)-2-methoxy-phenylamine (0.260 g, 0.529 mmol) and potassium carbonate (0.411 g, 3.00 mmol) in DMF (1.7 mL). After two days, more methyl bromoacetate (0.135 mL, 1.5 mmol) and the reaction mixture was stirred for a day longer. The reaction mixture was added to water and the solid was filtered and washed with water. The solid was triturated with pet. ether and dried at 60° C. under vacumm to provide the title compound as a white solid (0.212 g, 71%): mp 194–198° C.: NMR (DMSO-d6); 8.17 (dd, J=8, 1 Hz, 1H), 7.63 (ddd, J=8, 6, 1 Hz, 1H), 7.53–7.45 (m, 2H), 6.77 (d, J=2 Hz, 1H), 6.54 (d, J=2 Hz, 1H), 6.10 (t, J=7 Hz, 1H), 3.97 (dd, J=7, 4 Hz, 2H), 3.83 (s, 3H), 3.52 (s, 3H), 2.43 (s, 3H), 1.69 (s, 3H); MS (FAB+): 2 bromine isotope pattern 561, 563, 565; Anal. Calc. for C24H21Br2NO3S: C, 51.17; H, 3.76; N, 2.49. Found: C, 50.43; H, 3.63; N, 2.53.

EXAMPLE 60

[3-Bromo-5-(9-bromo-2,3-dimethyl-naphtho[2,3-b]thiophen-4-yl)-2-methoxy-phenylamino]-acetic Acid Aqueous potassium hydroxide (1N, 0.64 mL, 0.64 mmol) was added to a stirred room temperature solution of [3-bromo-5-(9-bromo-2,3-dimethyl-naphtho[2,3-b]thiophen-4-yl)-2-methoxy-phenylamino]-acetic acid methyl ester (0.180 g, 0.320 mmol) in THF (2.5 mL), methanol (1.5 mL). After 4 h, the solvent was removed and water was added. The suspension was acidified and extracted with ether. Silica gel was added. The ether was removed and the adsorbate was flash chromatographed (Gradient: 7:3pet. ether: ethyl acetate to ethyl acetate to 9:1 ethyl acetate:methanol) to provide the title compound as a white solid (0.112 g, 64%): mp >190° C. (dec): NMR (DMSO-d6); 8.16 (d, J=8 Hz, 1H), 7.63 (ddd, J=8, 6, 1 Hz, 1H), 7.56 (d, J=8 Hz, 1H), 7.48 (ddd, J=8, 6, 1 Hz, 1H), 6.72 (d, J=2 Hz, 1H), 6.43 (d, J=2 Hz, 1H), 5.74 broad s, 1H), 3.83 (s, 3H), 3.46 (s, 2H), 2.42 (s, 3H), 1.71 (s, 3H); MS (FAB+): 2 bromine isotope pattern 547, 549, 551; Anal. Calc. for C23H19Br2NO3S: C, 50.29; H, 3.49; N, 2.55. Found: C, 49.54; H, 3.73; N, 2.26.

EXAMPLE 61

(R)-2-[4-(9-Bromo-2,3-dimethyl-naphtho[2,3-b]thiophen-4-yl)-2,6-diethyl-phenoxy]-3-phenyl-propionic acid Step 1

(2-Benzyl-4,5-dimethyl-thiophen-3-yl)-(4-methoxy-3,5-diethyl-phenyl)-methanone

In a manner similar to the procedure of Example 49, Step 1, there was obtained from 3,5-diethyl-p-anisic acid (9.45 g, 45.4 mmol, prepared by the method of J. Lipowitz and T. Cohen, *J. Org. Chem.* 1965, 30, 3891–3894; C. K. Bradsher. et al; *J. Am. Chem. Soc.* 1954, 76, 2357–2362; C. K. Bradsher. et. al; *Org. Prep. Proced. Int.*, 1986, 18, 2213–2215), oxalyl chloride (4.4 mL, 49.9 mmol), N,N-dimethylformamide (2 drops), 2,3-dimethyl-5-benzylthiophene (11.0 g, 54.5 mmol), tin(IV) chloride (5.8 mL, 49.9 mmol), and anhydrous methylene chloride (291 mL) the title compound as an oil (17.7 g, 99%): (DMSO-d6): δ7.43 (s, 2H), 7.24–7.11 (m, 3H), 7.07–7.01 (m, 2H), 3.85 (s, 2H), 3.70 (s, 3H), 2.62 (q, 4H), 2.26 (s, 3H), 1.83 (s, 3H), 1.14 (t, 6H).

Step 2

4-(2,3-Dimethyl-naphtho[2,3-b]thiophen-4-yl)-2,6-diethyl-phenol

In a manner similar to the procedure of Example 49, Step 2, there was obtained from (2-benzyl-4,5-dimethyl-thiophen-3-yl)-(4-methoxy-3,5-diethyl-phenyl)-methanone (17.67 g, 45.0 mmol), boron tribromide (12.8 mL, 135.4 mmol), and methylene chloride (90 mL) the title compound (16.6 g), which was used without further purification: (DMSO-d6): δ8.41 (s, 1H), 8.31 (s, 1H), 7.93 (d, 1H), 7.47 (d, 1H), 7.42 (ddd, 1H), 7.32 (ddd, 1H), 6.86 (s, 2H), 2.76–2.56 (complex m, ABX pattern, 4H), 2.39 (s, 3H), 1.60 (s, 3H), 1.14 (t, 6H); MS(+ESI): [M]+360.

Step 3

Acetic acid 4-(2,3-dimethyl-naphtho[2,3-b]thiophen-4-yl)-2,6-diethyl-phenyl ester In a manner similar to the procedure of Example 49, Step 3, there was obtained from 4-(2,3-dimethyl-naphtho[2,3-b]thiophen-4-yl)-2,6-diethyl-phenol (16.6 g, 46.0 mmol), acetic anhydride (5.66 mL, 59.9 mmol), pyridine (92 mL), and methylene chloride (92 mL) a residue, which was triturated with acetone:hexane (1:1) to give the title compound as a solid (6.85 g, 37%): NMR (DMSO-d6): δ8.47 (s, 1H), 7.97 (d, 1H), 7.49–7.34 (m, 3H), 7.11 (s, 2H), 2.60–2.46 (m, 4H), 2.40 (two overlapping s, 6H), 1.59 (s, 3H), 1.13 (t, 6H); MS(+ESI): [M+H] 403; Anal. Calc. for C26H26O2S: C, 77.57; H, 6.51; N, 0.00. Found: C, 76.46; H, 6.60; N, 0.19.

Step 4

Acetic acid 4-(9-bromo-2,3-dimethyl-naphtho[2,3-b]thiophen-4-yl)-2,6-diethyl-phenyl ester In a manner similar to the procedure of Example 49, Step 4, there was obtained from acetic acid 4-(2,3-dimethyl-naphtho[2,3-b]thiophen-4-yl)-2,6-diethyl-phenyl ester (1.0 g, 2.5 mmol), ferric chloride (20 mg, 0.12 mmol), bromine (2.7 mL, 2.7 mmol), and methylene chloride (25 mL) the title compound as a solid (1.2 g, 100%): NMR (DMSO-d6): δ8.20 (d, 1H), 7.68–7.61 (m, 1H), 7.49 (d, 2H), 7.13 (s, 2H), 2.60–2.47 (m, 4H), 2.42 (s, 3H), 2.40 (s, 3H), 1.56 (s, 3H), 1.13 (t, 6H); MS(+APCI): [M+H], 1 bromine isotope pattern, 481/483; Anal. Calc. for C26H25BrO2S: C, 64.86; H, 5.23; N, 0.00. Found: C, 63.06; H, 5.13; N, 0.03.

Step 5

4-(9-Bromo-2,3-dimethyl-naphtho[2,3-b]thiophen-4-yl)-2,6-diethyl-phenol

In a manner similar to the procedure of Example 49, Step 5, there was obtained from acetic acid 4-(9-bromo-2,3-dimethyl-naphtho[2,3-b]thiophen-4-yl)-2,6-diethyl-phenyl ester (1.0 g, 2.1 mmol), aqueous potassium hydroxide (2.5 mL of a 1 N solution, 2.5 mmol), tetrahydrofuran (29.7 mL), and enough methanol to create a homogeneous solution the title compound as a solid (0.83 g, 91%): NMR (DMSO-d6): δ8.36 (s, 1H), 8.16 (d, 1H), 7.61 (ddd, 1H), 7.55 (d, 1H), 7.44 (ddd, 1H), 6.88 (s, 2H), 2.76–2.56 (complex m, ABX pattern, 4H), 2.41 (s, 3H), 1.58 (s, 3H), 1.14 (t, 6H); MS(+APCI): [M+H], 1 bromine isotope pattern, 439/441.

Step 6

(2R)-2-[4-(9-bromo-2,3-dimethyl-naphtho[2,3-b]thiophen-4-yl)-2,6-diethyl-phenoxy]-3-phenyl-propionic acid methyl ester In a manner similar to the procedure of Example 49, Step 6, there was obtained from 4-(9-bromo-2,3-dimethyl-naphtho[2,3-b]thiophen-4-yl)-2,6-diethyl-phenol (0.83 g, 1.89 mmol), (S)-2-hydroxy-3-phenylpropionic acid, methyl ester (2.72 g, 15.0 mmol), triphenylphosphine (3.96 g, 15.0 mmol), diethylazodicarboxylate (2.36 mL, 15.0 mmol), and anhydrous benzene (40 mL) at room temperature the title compound as a solid (0.74 g, 65%): NMR (DMSO-d6): δ8.18 (d, 1H), 7.66–7.60 (m, 1H), 7.48–7.44 (m, 2H), 7.37–7.23 (m, 5H), 7.01 (s, 2H), 4.69 (t, 1H), 3.55 (s, 3H), 3.29 (m, 2H), 2.74–2.45 (m, 4H), 2.41 (s, 3H), 1.53 (s, 3H), 1.09 and 1.08 (two t, 6H); MS(+APCI): [M+H], 1 bromine isotope pattern, 601/603.

Step 7

(2R)-2-[4-(9-Bromo-2,3-dimethyl-naphtho[2,3-b]thiophen-4-yl)-2,6-diethyl-phenoxy]-3-phenyl-propionic acid In a manner similar to the procedure of Example 49, Step 7, there was obtained from (2R)-2-[4-(9-bromo-2,3-dimethyl-naphtho[2,3-b]thiophen-4-yl)-2,6-diethyl-phenoxy]-3-phenyl-propionic acid methyl ester (0.70 g, 1.16 mmol), aqueous potassium hydroxide (2.3 mL of a 1 N solution, 2.3 mmol), tetrahydrofuran (11.6 mL), and enough methanol to create a homogeneous solution as a solid. Recrystallization from hexane/acetone gave the title compound as a white solid (0.15 g, 22%): NMR (DMSO-d6): δ12.91 (br s, 1H), 8.18 (d, 1H), 7.63 (ddd, 1H), 7.51–7.42 (m, 2H), 7.36–7.22 (m, 5H), 7.00 (s, 2H), 4.62 (t, 1H), 3.25 (d, 2H), 2.74 (complex m, ABX pattern, 1H), 2.66 (complex m, ABX pattern, 2H), 2.55 (complex m, ABX pattern, 1H), 2.41 (s, 3H), 1.53 (s, 3H), 1.10 (t, 6H); MS(-ESI): [M–H], 1 bromine isotope pattern, 585/587; Anal. Calc. for C33H31BrO3S: C, 67.46; H, 5.32; N, 0.00. Found: C, 66.84; H, 5.24; N, 0.03.

EXAMPLE 62

{(2R)-2-[4-(9-Bromo-2,3-dimethyl-naphtho[2,3-b]thiophen-4-yl)-2,6-dimethyl-phenoxy]-3-phenyl-propionylamino}-acetic acid A mixture of (2R)-2-[4-(9-bromo-2,3-dimethyl-naphtho[2,3-b]thiophen-4-yl)-2,6-dimethyl-phenoxy]-3-phenyl-propionic acid (0.5 g, 0.89 mmol), 1-(3-dimethylaminopropyl)-3-ethylcarbodiimide hydrochloride (0.34 g, 1.77 mmol), glycine ethyl ester hydrochloride (0.24 g, 1.72 mmol), potassium carbonate (0.50 g, 3.62 mmol), and methylene chloride (6 mL) was stirred at room temperature. After three days the reaction was diluted with methylene chloride, washed twice with water, once with brine, and then dried (Na2SO4). Adsorption onto silica gel and chromatography with hexane:ethyl acetate (75:25) gave a solid (0.4 g), which was treated with potassium hydroxide (1.11 mL of a 1N solution, 1.11 mmol), tetrahydrofuran (8.9 mL), and enough methanol to create a homogeneous solution. After 24 h at room temperature the reaction mixture was diluted with diethyl ether, washed once with 1N aqueous hydrochloric acid, twice with water, once with brine, and then dried (Na2SO4). Concentration under reduced pressure and recrystallization from hexane/ethyl acetate gave a white solid (0.20 g, 36%): NMR (DMSO-d6): δ12.58 (br s, 1H), 8.53 (t, 1H), 8.18 (d, 1H), 7.64 (ddd, 1H), 7.52–7.43 (m, 2H), 7.34–7.19 (m, 5H), 6.92 (s, 2H), 4.87 (t, 1H), 3.88–3.70 (two overlapping quartets, ABX pattern, 2H), 3.31–3.10 (two overlapping quartets, ABX pattern, 2H), 2.43 (s, 3H), 2.23 (s, 3H), 2.19 (s, 3H), 1.56 (s, 3H); MS(+APCI): [M+H], 1 bromine isotope pattern, 616/618; Anal. Calc. for C33H30BrNO4S: C, 64.29; H, 4.90; N, 2.27. Found: C, 63.97; H, 4.48; N, 2.03.

EXAMPLE 63

{(2R)-2-[4-(9-Bromo-2,3-dimethyl-naphtho[2,3-b]thiophen-4-yl)-2,6-diethyl-phenoxy]-3-phenyl-propionylamino}-acetic acid A mixture of (2R)-2-[4-(9-bromo-2,3-dimethyl-naphtho[2,3-b]thiophen-4-yl)-2,6-diethyl-phenoxy]-3-phenyl-propionic acid (0.48 g, 0.82 mmol), oxalyl chloride (0.071 mL, 0.81 mmol), and benzene (16.3 mL) was stirred at room temperature for 40 min. Glycine ethyl ester hydrochloride (0.14 g, 1.0 mmol) and potassium carbonate (0.36, 2.6 mmol) was added, and the resulting slurry was allowed to stir at room temperature overnight. The reaction mixture was adsorbed onto silica gel and chromatographed with hexane-:ethyl acetate (90:10) to give a solid (0.17 g), which was treated with potassium hydroxide (1.32 mL of a 1N solution, 1.32 mmol), tetrahydrofuran (10 mL), and enough methanol to create a homogeneous solution. After stirring at room temperature for approximately 30 min, the reaction mixture was diluted with diethyl ether, washed once with 1N aqueous hydrochloric acid, once with water, once with brine, and then dried (Na2SO4). The solution was concentrated under reduced pressure, dissolved in methylene chloride, and dried (Na2SO4). Concentration under reduced pressure gave a white solid (0.14 g, 26%): NMR (DMSO-d6): δ12.51 (br s, 1H), 8.49 (t, 1H), 8.17 (d, 1H), 7.62 (ddd, 1H), 7.46 (d, 2H), 7.32–7.17 (m, 5H), 6.95 (s, 1H), 6.94 (s, 1H), 4.73 (t, 1H), 3.85–3.68 (two overlapping quartets, ABX pattern, 2H), 3.30–3.10 (two overlapping quartets, ABX pattern, 2H), 2.80–2.50 (complex m, ABX pattern, 4H), 2.41 (s, 3H), 1.54 (s, 3H), 1.06 (t, 6H); MS(-ESI): [M–H], 1 bromine isotope pattern, 642/644; Anal. Calc. for C35H34BrNO4S: C, 65.21; H, 5.32; N, 2.17. Found: C, 65.03; H, 5.36; N, 2.07.

EXAMPLE 64

(2R)-2-[4-(9-Bromo-2,3-dimethyl-naphtho[2,3-b]thiophen-4-yl)-phenoxy]3-phenyl-propionic acid Step 1

(2R)-2-[4-(9-Bromo-2,3-dimethyl-naphtho[2,3-b]thiophen-4-yl)-phenoxy]-3-phenyl-propionic acid methyl ester In a manner similar to the procedure of Example 49, Step 6 there was obtained from 4-(9-bromo-2,3-dimethyl-naphtho[2,3-b]thiophen-4-yl)-phenol (5.13 g, 13.4 mmol), (S)-2-hydroxy-3-phenylpropionic acid, methyl ester (4.8 g, 26.6 mmol), triphenylphosphine (7.0 g, 26.7 mmol), diethylazodicarboxylate (4.2 mL, 26.7 mmol), and anhydrous benzene (74 mL) at room temperature the title compound as a solid (4.8 g, 66%): NMR (DMSO-d6): δ8.17 (d, J=8 Hz, 1H), 7.62 (ddd, J=1, 6, 8 Hz, 1H), 7.50–7.20 (m containing a doublet at δ7.22 (J=8 Hz), 9H), 7.01 (d, J=8 Hz, 2H), 5.25 (dd, J=5, 7 Hz, 1H), 3.67 (s, 3H), 3.25 (complex m, ABX pattern, 2H), 2.41 (s, 3H), 1.51 (s, 3H); MS(+APCI): [M+H]+, 1 bromine isotope pattern, 545/547; Anal. Calc. for C30H25BrO3S: C, 66.06; H, 4.62; N, 0.00. Found: C, 66.15; H, 4.82; N, –0.11.

Step 2

(2R)-2-[4-(9-Bromo-2,3-dimethyl-naphtho[2,3-b]thiophen-4-yl)-phenoxy]-3-phenyl-propionic Acid In a manner similar to the procedure of Example 49, Step 7 there was obtained from (2R)-2-[4-(9-bromo-2,3-dimethyl-naphtho[2,3-b]thiophen-4-yl)-phenoxy]-3-phenyl-propionic acid methyl ester (0.6 g, 1.10 mmol), aqueous potassium hydroxide (1.3 mL of a 1 N solution, 1.3 mmol), tetrahydrofuran (15.7 mL), and enough methanol to create a homogeneous solution the title compound as a solid (0.58 g, 99%): NMR (DMSO-d6): δ13.14 (br s, 1H), 8.17 (d, J=8 Hz, 1H), 7.62 (ddd, J=1, 6, 8 Hz, 1H), 7.48–7.20 (m continting a doublet at δ7.22 (J=8 Hz), 9H), 7.00 (d, J=8 Hz, 2H), 5.08 (dd, J=5, 8 Hz, 1H), 3.32–3.15 (two overlapping quartets, ABX pattern, 2H), 2.41 (s, 3H), 1.53 (s, 3H); MS(+APCI): [M+H]+, 1 bromine isotope pattern, 531/533; Anal. Calc. for C29H23BrO3S: C, 65.54; H, 4.36; N, 0.00. Found: C, 65.51; H, 4.61; N, 0.09.

EXAMPLE 65

(2S)-2-[4-(9-Bromo-2-,3-dimethyl-naphtho[2,3-b]
thiophen-4-yl)-2,6-dimethyl-phenoxy]-3-phenyl-
propionic acid Step 1

(2S)-2-[4-(9-Bromo-2,3-dimethyl-naphtho[2,3-b]
thiophen-4-yl)-2,6-dimethyl-phenoxy]-3-phenyl-
propionic acid methyl ester In a manner similar to the procedure of Example 49, Step 6 there was obtained from 4-(9-bromo-2,3-dimethyl-naphtho[2,3-b]thiophen-4-yl)-2,6-dimethyl-phenol (10.4 g, 25.4 mmol), (S)-2-hydroxy-3-phenylpropionic acid, methyl ester (13.7 g, 76.0 mmol), triphenylphosphine (20.0 g, 76.3 mmol), diethylazodicarboxylate (12.0 mL, 76.2 mmol), and anhydrous THF (139 mL) at room temperature the title compound as a sticky foam (8.66 g, 59%): Opt. Rot. [a]25/D=−44.19° (9.188 mg/mL, MeOH); NMR(DMSO-d6): δ8.18 (d, J=8 Hz, 1H), 7.62 (ddd, J=2, 6, 8 Hz, 1H), 7.51–7.42 (m, 2H), 7.36–7.23 (m, 5H), 6.98 (s, 2H), 4.78 (t, J=7 Hz, 1H), 3.56 (s,3H), 3.29 (m, 2H), 2.41 (s, 3H), 2.22 (s, 3H), 2.17 (s, 3H), 1.54 (s, 3H); MS(+APCI): [M+H], 1 bromine isotope pattern, 573/575; Anal. Calc. for C32H29BrO3S: C, 67.01; H, 5.10; N, 0.00. Found: C, 66.72; H, 4.86; N, 0.12.

Step 2

(2S)-2-[4-(9-Bromo-2,3-dimethyl-naphtho[2,3-b]
thiophen-4-yl)-2,6-dimethyl-phenoxy]-3-phenyl-
propionic acid In a manner similar to the procedure of Example 49, Step 7 there was obtained from (2S)-2-[4-(9-bromo-2,3-dimethyl-naphtho[2,3-b]thiophen-4-yl)-2,6-dimethyl-phenoxy]-3-phenyl-propionic acid methyl ester (4.0 g, 6.97 mmol), aqueous potassium hydroxide (8.4 mL of a 1 N solution, 8.4 mmol), tetrahydrofuran (99.6 mL), and enough methanol to create a homogeneous solution a solid. Recrystallization from 2% ethyl acetate in hexane gave the title compound as a white solid (1.45 g, 37%): mp 134–139° C.; Opt. Rot. [a]25/D=−35.86° (10.040 mg/mL, MeOH); NMR (DMSO-d6): δ12.92 (br s, 1H), 8.17 (d, J=8 Hz, 1H), 7.63 (ddd, J=2,6,8 Hz, 1H), 7.52–7.42 (m, 2H), 7.37–7.21 (m, 5H), 6.97 (s, 2H), 4.72 (t, J=7 Hz, 1H), 3.25 (d, J=7 Hz, 2H), 2.41 (s, 3H), 2.25 (s, 3H), 2.22 (s, 3H), 1.54 (s, 3H); MS(−ESI): [M−H]−, 1 bromine isotope pattern, 557/559; Anal. Calc. for C31H27BrO3S: C, 66.55; H, 4.86; N, 0.00. Found: C, 66.17; H, 4.87; N, 0.01; Analytical HPLC indicates a major component (98.1%).

EXAMPLE 66

(2R)-2-[4-(9-Bromo-2,3-dimethyl-1-oxo-1H-
naphtho[2,3-b]thiophen-4-yl)-2,6-dimethyl-
phenoxy]-3-phenyl-propionic acid From a solution of (2R)-2-[4-(9-bromo-2,3-dimethyl-naphtho[2,3-b]thiophen-4-yl)-2,6-dimethyl-phenoxy]-3-phenyl-propionic acid (0.5 g, 0.89 mmol), glacial acetic acid (6.6 mL), and 30% aqueous hydrogen peroxide solution (1.0 mL, 9.8 mmol) there was obtained a slurry, which was immediately diluted with water and extracted with diethyl ether. Purification by chromatography with methanol/methylene chloride gave the title compound as a pale yellow solid (0.12 g, 23%): Opt. Rot. [a]25/D=+29.57° (7.88 mg/mL, MeOH); NMR (DMSO-d6): δ13.10 (br s, 1H), 8.28 (d, J=8 Hz, 1H), 7.74 (ddd, J=1, 7, 8 Hz, 1H), 7.63 (ddd, J=1, 7, 8 Hz, 1H), 7.39 (d, J=8 Hz, 1H), 7.36–7.18 (m, 5H), 7.01 (s, 1H), 6.89 (s, 1H), 4.69 (t, J=7 Hz, 1H), 3.23 (m, 2H), 2.24, 2.21, 2.20, 2.18 (4 s, mixture of sulfoxide diastereomers, 6H), 2.17 (s, 3H), 1.42 (s, 3H); MS(−APCI): [M−H]−, 1 bromine isotope pattern, 573/575; Anal. Calc. for C31H27BrO4S: C, 64.70; H, 4.73; N, 0.00. Found: C, 64.18; H, 4.44; N, −0.03. Analytical HPLC indicates two major peaks (45.16%, 47.72%), a mixture of sulfoxide diastereomers.

EXAMPLE 67

(R)-2-[4-(2-,3-Dimethyl-naphtho[2,3-b]thiophen-4-
yl)-2,6-diethyl-phenoxy]-3-phenyl-propionic acid Step 1

(2R)-2-[4-(2,3-Dimethyl-naphtho[2,3-b]thiophen-4-
yl)-2,6-diethyl-phenoxy]-3-phenyl-propionic acid
methyl ester In a manner similar to the procedure of Example 49, Step 6 there was obtained from 4-(2,3-dimethyl-naphtho[2,3-b]thiophen-4-yl)-2,6-diethyl-phenol (0.84 g, 2.33 mmol), (S)-2-hydroxy-3-phenylpropionic acid, methyl ester (3.36 g, 18.6 mmol), triphenylphosphine (4.8 g, 18.3 mmol), diethylazodicarboxylate (2.92 mL, 18.5 mmol), and anhydrous benzene (75 mL) at room temperature the title compound as a solid (0.50 g, 42%): NMR (DMSO-d6): δ8.44 (s, 1H), 7.94 (d, J=8 Hz, 1H), 7.48–7.22 (m, 8H), 6.99 (s, 2H), 4.69 (t, J=7 Hz, 1H), 3.55 (s, 3H), 3.27 and 3.22 (two overlapping dd, J=6, 13 Hz, 2H), 2.70–2.40 (complex m, ABX pattern, 4H), 2.38 (s, 3H), 1.53 (s, 3H), 1.10 and 1.09 (two overlapping triplets, J=8 Hz, 6H); MS(+APCI): [M+H]+, 523.

Step 2

(2R)-2-[4-(2,3-Dimethyl-naphtho[2,3-b]thiophen-4-
yl)-2,6-diethyl-phenoxy]-3-phenyl-propionic acid In a manner similar to the procedure of Example 49, Step 7 there was obtained from (2R)-2-[4-(2,3-dimethyl-naphtho[2,3-b]thiophen-4-yl)-2,6-diethyl-phenoxy]-3-phenyl-propionic acid methyl ester (0.46 g, 0.88 mmol), aqueous potassium hydroxide (1.1 mL of a 1 N solution, 1.1 mmol), tetrahydrofuran (12.6 mL), and enough methanol to create a homogeneous solution the title compound as a white solid (0.43 g, 89%): NMR (DMSO-d6): δ12.91 (br s, 1H), 8.44 (s, 1H), 7.94 (d, J=8 Hz, 1H), 7.47–7.22 (m, 8H), 6.98 (s, 2H), 4.61 (t, J=7 Hz, 1H), 3.25 (d, J=7 Hz, 2H), 2.72 (complex m, ABX pattern, 1H), 2.66 (two overlapping quartets, J=8 Hz, 2H), 2.55 (complex m, ABX pattern, 1H), 2.38 (s, 3H), 1.55 (s, 3H), 1.10 and 1.09 (two overlapping triplets, J=8 Hz, 6H); MS(−ESI): [M−H]−, 507; Anal. Calc. for C33H32O3S.0.6H2O: C, 76.30; H, 6.44; N, 0.00. Found: C, 76.44; H, 6.49, N, 0.04.

EXAMPLE 68

{(2R)-2-[4-(2,3-Dimethyl-naphtho[2,3-b]thiophen-4-
yl)-2,6-diethyl-phenoxy]-3-phenyl-propionylamino}-
acetic acid In a manner similar to the procedure of Example 63 there was obtained from (2R)-2-[4-(2,3-dimethyl-naphtho[2,3-b]thiophen-4-yl)-2,6-diethyl-phenoxy]-3-phenyl-propionic acid (0.27 g, 0.53 mmol), oxalyl chloride (0.046 mL, 0.53 mmol), N,N-dimethylformamide (two drops), benzene (9 mL), glycine ethyl ester hydrochloride (0.18 g, 1.29 mmol), and potassium carbonate (0.46, 3.33 mmol) at room temperature a solid which was adsorbed onto silica gel and chromatographed with hexane:ethyl acetate (90:10). The resulting solid (0.18 g), was treated with potassium hydroxide (2.34 mL of a 1N solution, 2.34 mmol), tetrahydrofuran (10 mL), and enough methanol to create a homogeneous solution. This yielded the title compound as a pale yellow solid (0.10 g, 33%): NMR (DMSO-d6): δ12.52 (br s, 1H), 8.48 (t, J=6 Hz, 1H), 8.43 (s, 1H), 7.94 (d, J=8 Hz, 1H), 7.48–7.16 (m, 8H), 6.93 (s, 2H), 4.73 (t, J=7 Hz, 1H), 3.79 and 3.73 (two overlapping dd, J=6, 17 Hz, 2H), 3.24 (dd, J=7, 14 Hz, 1H), 3.15 (dd, J=7, 14 Hz, 1H), 2.80–2.50 (complex m, ABX pattern, 4H)), 2.39 (s, 3H), 1.56 (s, 3H), 1.07 (t, J=8 Hz, 6H); MS(+APCI): [M+H]$^+$, 566; Anal. Calc. for $C_{35}H_{35}NO_4S$: C, 74.31; H, 6.24; N, 2.48. Found: C, 74.11; H, 6.69; N, 2.24

EXAMPLE 69

4-(2,3-Dimethyl-naphtho[2,3-b]furan-4-yl)-2,6-diethyl-phenol

Step 1

(2-Benzyl-4,5-dimethyl-furan-3-yl)-(4-methoxy-3,5-diethyl-phenyl)-methanone

In a manner similar to the procedure of Example 49, Step 1 there was obtained from 3,5-diethyl-p-anisic acid (10.66 g, 51.2 mmol; prepared in three steps from 4-bromo-2,6-diethyl aniline by the methods of J. Lipowitz and T. Cohen, *J. Org. Chem.* 1965, 30, 3891–3894; C. K. Bradsher. et al; *J. Am. Chem. Soc.* 1954, 76, 2357–2362; J. Alexander, *Org. Prep. Proced. Int.,* 1986, 18, 2213–2215), oxalyl chloride (4.9 mL, 56.2 mmol), N,N-dimethylformamide (2 drops), 2,3-dimethyl-5-benzylfuran (11.4 g, 61.2 mmol), tin(IV) chloride (6.6 mL, 56.4 mmol), and anhydrous methylene chloride (198 mL) the title compound as an oil (22 g, >100%): (DMSO-d6): δ7.42 (s, 2H), 7.29–7.21 (m, 3H), 7.04 (d, J=7 Hz, 2H), 3.82 (s, 2H), 3.74 (s, 3H), 2.61 (quartet, J=8 Hz, 4H), 2.19 (s, 3H), 1.83 (s, 3H), 1.13 (t, J=8 Hz, 6H).

Step 2

4-(2,3-Dimethyl-naphtho[2,3-b]furan-4-yl)-2,6-diethyl-phenol

In a manner similar to the procedure of Example 49, Step2 there was obtained from (2-benzyl-4,5-dimethyl-furan-3-yl)-(4-methoxy-3,5-diethyl-phenyl)-methanone (22 g), boron tribromide (36.8 mL, 389 mmol), and methylene chloride (180 mL) after refluxing for 4 h, the title compound as an off-white solid (3.09 g, 17.5%): (DMSO-d6): δ8.29 (s, 1H), 7.96 (d, J=8 Hz, 1H), 7.90 (s, 1H), 7.57 (d, J=8 Hz, 1H), 7.39 (ddd, J=1, 7, 8 Hz, 1H), 7.29 (ddd, J=1, 7, 8 Hz, 1H), 6.89 (s, 1H), 2.75–2.55 (complex m, ABX pattern, 4H), 2.36 (s, 3H), 1.55 (s, 3H), 1.15 (t, J=8 Hz, 6H); MS(EI): [M+] 344; Anal. Calc. For $C_{24}H_{24}O_2$: C, 83.69; H, 7.02; N, 0.00. Found: C, 82.53; H, 7.11; N, 0.05.

EXAMPLE 70

(R)-2-[4-(9-Bromo-2-,3-dimethyl-naphtho[2,3-b]furan-4-yl)-2,6-diethyl-phenoxy]-3phenyl-propionic acid Step 1

Acetic acid 4-(9-bromo-2,3-dimethyl-naphtho[2,3-b]furan-4-yl)-2,6-diethyl-phenyl ester In a manner similar to the procedure of Example 49, Step 3 there was obtained from 4-(2,3-dimethyl-naphtho[2,3-b]furan-4-yl)-2,6diethyl-phenol (1.75 g, 5.1 mmol), acetic anhydride (0.62 mL, 6.6 mmol), and pyridine (10.2 mL) a solid (2.23 g), which was used without further purification.

In a manner similar to the procedure of Example 49, Step4 there was obtained from acetic acid 4-(2,3-dimethyl-naphtho[2,3-b]furan-4-yl)-2,6-diethyl-phenyl ester (2.23 g 5.8 mmol), ferric chloride (247 mg, 0.29 mmol), bromine (0.34 mL, 6.4 mmol), and methylene chloride (58 mL) the title compound as a solid (0.29 g, 10%): NMR (DMSO-d6): δ8.26 (d, J=8 Hz, 1H), 7.64 (ddd, J=1, 7, 8 Hz, 1H), 7.59 (d, J=9 Hz, 1H), 7.48 (ddd, J=1, 7, 8 Hz, 1H), 7.16 (s, 2H), 2.54 and 2.53 (two overlapping quartets, J=7 Hz, 4H), 2.44 (s, 3H), 2.42 (s, 3H), 1.54 (s, 3H), 1.14 (t, J=7 Hz, 6H); MS(EI): [M+], 1 bromine isotope pattern, 464/466.

Step 2

4-(9-Bromo-2,3-dimethyl-naphtho[2,3-b]furan-4-yl)-2,6-diethyl-phenol

In a manner similar to the procedure of Example 49, Step 5 there was obtained from acetic acid 4-(9-bromo-2,3-dimethyl-naphtho[2,3-b]furan-4-yl)-2,6-diethyl-phenyl ester (0.29 g, 0.62 mmol), aqueous potassium hydroxide (0.75 mL of a 1 N solution, 0.75 mmol), tetrahydrofuran (8.9 mL), and enough methanol to create a homogeneous solution the title compound as a solid (0.26 g, 100%): NMR (DMSO-d6): δ8.36 (s, 1H), 8.21 (d, J=8 Hz, 1H), 7.63 (d, J=8 Hz, 1H), 7.59 (ddd, J=1, 7, 8 Hz, 1H), 7.41 (ddd, J=1, 7, 8 Hz, 1H), 6.91 (s, 2H), 2.69 and 2.62 (two overlapping quartets, J=7 Hz, 4H), 2.41 (s, 3H), 1.55 (s, 3H), 1.14 (t, J=7 Hz, 6H); MS(EI): [M+], 1 bromine isotope pattern, 422/424.

Step 3

(2R)-2-[4-(9-Bromo-2,3-dimethyl-naphtho[2,3-b]furan-4-yl)-2,6-diethyl-phenoxy]-3-phenyl-propionic acid In a manner similar to the procedure of Example 49, Step 6 there was obtained from 4-(9-bromo-2,3-dimethyl-naphtho[2,3-b]furan-4-yl)-2,6-diethyl-phenol (0.26 g, 0.64 mmol), (S)-2-hydroxy-3-phenylpropionic acid, methyl ester (1.38 g, 7.66 mmol), triphenylphosphine (1.98 g, 7.55 mmol), diethylazodicarboxylate (1.2 mL, 7.62 mmol), and anhydrous benzene (0.85 mL) at 100° for 36 h a solid (0.15 g, 39%), which was used without further purification.

In a manner similar to the procedure of Example 49, Step 7 there was obtained from (2R)-2-[4-(9-bromo-2,3-dimethyl-naphtho[2,3-b]furan-4-yl)-2,6-diethyl-phenoxy]-3-phenyl-propionic acid methyl ester (0.15 g, 0.25 mmol), aqueous potassium hydroxide (0.98 mL of a 1 N solution, 0.98 mmol), tetrahydrofuran (2.5 mL), and enough methanol to create a homogeneous solution the title compound as a white solid (0.1 g, 71%): NMR (DMSO-d6): δ12.95 (br s, 1H), 8.23 (d, J=8 Hz, 1H), 7.66 (m, 1H), 7.64–7.53 (m, 2H), 7.43–7.30 (m, 5H), 7.02 (s, 2H), 4.61 (t, J=7 Hz, 1H), 3.25 (d, J=7 Hz, 2H), 2.82–2.52 (complex m, ABX pattern, 4H), 2.41 (s, 3H), 1.49 (s, 3H), 1.11 and 1.10 (two overlapping triplets, J=7 Hz, 6H); MS(-ESI): [M–H], 1 bromine isotope pattern, 569/571; Anal. Calc. for $C_{33}H_{31}BrO_4$: C, 69.35; H, 5.47; N, 0.00. Found: C, 69.93; H, 5.84; N, 0.19; Analytical HPLC indicates a major component (98.3%).

EXAMPLE 71

(R)-2-[2-Cyclopentyl-4-(2-,3-dimethyl-naphtho[2,3-b]thiophen-4-yl)-phenoxy]-propionic acid Step 1

(2R)-2-[2-Cyclopentyl-4-(2-,3-dimethyl-naphtho[2,3-b]thiophen-4-yl)-phenoxy]-propionic acid methyl ester In a manner similar to the procedure of Example 49, Step 6 there was obtained from 2-cyclopentyl-4-(2,3-dimethylnaphtho[2,3-b]thiophen-4-yl)-phenol (0.80 g, 2.2 mmol), methyl (S)-(–)-lactate (0.24 mL, 3.3 mmol), triphenylphosphine (0.84 g, 3.2 mmol), diethylazodicarboxylate (0.51 mL, 3.2 mmol), and anhydrous benzene (5 mL) at 90° the title compound as a white solid (0.67 g, 68%): mp 65–66° C.; NMR (DMSO-d 6): δ8.46 (s, 1H), 7.96 (d, J=8 Hz, 1H), 7.50–7.30 (m, 3H), 7.14 (m, 1H), 7.09 and 7.08 (two dd, J=2, 8 Hz, atroph isomers, 1H), 6.95 and 6.92 (two d, J=8 Hz, atroph isomers, 1H), 5.14 and 5.11 (two quartets, J=7 Hz, atroph isomers, 1H), 3.75 and 3.70 (two s, atroph isomers, 3H), 3.43 (m, 1H), 2.41 (s, 3H), 2.00 (m, 2H), 1.77–1.50 (m containing a doublet (J=7 Hz) at δ1.61 and a singlet at δ1.57, 12H); MS(EI): [M+], 458; Anal. Calc. for C29H30O3S: C, 75.95; H, 6.59; N, 0.00. Found: C, 74.93; H, 6.55, N, –0.09.

Step 2

(2R)-2-[2-Cyclopentyl-4-(2-,3-dimethyl-naphtho[2,3-b]thiophen-4-yl)-phenoxy]-propionic acid In a manner similar to the procedure of Example 49, Step 7 there was obtained from (2R)-2-[2-cyclopentyl-4-(2,3-dimethyl-naphtho[2,3-b]thiophen-4-yl)-phenoxy]-propionic acid methyl ester (0.60 g, 1.3 mmol), aqueous potassium hydroxide (1.98 mL of a 1 N solution, 1.98 mmol), tetrahydrofuran (9 mL), and methanol (3 mL) the title compound as a white solid (0.55 g, 95%): Opt. Rot. [a]25/D=+7.95° (10.068 mg/mL, MeOH); NMR (DMSO-d6): δ13.02 (br s, 1H), 8.46 (s, 1H), 7.96 (d, J=8 Hz, 1H), 7.50–7.30 (m, 3H), 7.13 and 7.12 (two doublets, J=2 Hz, atroph isomers, 1H), 7.11 and 7.09 (two dd, J=2, 8 Hz, atroph isomers, 1H), 6.93 and 6.91 (two doublets, J=8 Hz, atroph isomers, 1H), 4.95 (q, J=7 Hz, 1H), 3.44 (m, 1H), 2.41 (s, 3H), 2.00 (m, 2H), 1.79–1.50 (m containing a doublet (J=7 Hz) at δ1.60 and a singlet at δ1.58, 12H); MS(EI): [M+], 444; Anal. Calc. for C28H28O3S: C, 75.64; H, 6.35, N, 0.00. Found: C, 74.10; H, 6.32, N, –0.09; Analytical HPLC indicates a major component (99.99%).

EXAMPLE 72

(R)-2-[4-(9-Bromo-2-,3-dimethyl-naphtho[2,3-b]thiophen-4-yl)-2-cyclopentyl-phenoxy]-propionic acid In a manner similar to the procedure of Example 49, Step 6 there was obtained from 2-cyclopentyl-4-(9-bromo-2,3-dimethyl-naphtho[2,3-b]thiophen-4-yl)-phenol (0.37 g, 0.99 mmol), methyl (S)-(–)-lactate (0.75 mL, 7.9 mmol), triphenylphosphine (2.1 g, 8.0 mmol), diethylazodicarboxylate (1.23 mL, 7.8 mmol), and anhydrous benzene (1.0 mL) at 90° for 18 h the title compound as a solid (0.20 g, 28%), which was used without further purification.

In a manner similar to the procedure of Example 49, Step 7 there was obtained from (2R)-2-[4-(9-bromo-2,3-dimethyl-naphtho[2,3-b]thiophen-4-yl)-2-cyclopentyl-phenoxy]-propionic acid methyl ester (0.20 g, 0.37 mmol), aqueous potassium hydroxide (0.74 mL of a 1 N solution, 0.74 mmol), tetrahydrofuran (3.7 mL), and enough methanol to create a homogeneous solution the title compound as an off-white solid (0.18 g, 95%): NMR (DMSO-d6): δ13.00 (br s, 1H), 8.18 (d, J=8 Hz, 1H), 7.63 (m, 1H), 7.50–7.40 (m, 2H), 7.14 and 7.13 (two doublets, J=2 Hz, atroph isomers, 1H), 7.10 and 7.09 (two dd, J=2,8 Hz, atroph isomers, 1H), 6.93 and 6.91 (two doublets, J=8 Hz, atroph isomers, 1H), 4.94 (q, J=7 Hz, 1H), 3.41 (m, 1H), 2.42 (s, 3H), 1.98 (m, 2H), 1.78–1.46 (m containing two doublets at δ1.59 and 1.58 (J=7 Hz, atroph isomers) and a singlet at δ1.54, 12H); MS(–ESI): [M–H], 1 bromine isotope pattern, 521/523; Anal. Calc. for C28H27BrO3S: C, 64.24; H, 5.20; N, 0.00. Found: C, 64.11; H, 5.52; N, 0.10.

EXAMPLE 73

4-[4-(9-Bromo-2-,3-dimethyl-naphtho[2,3-b]thiophen-4-yl)-2-cyclopentyl-phenoxy]-butyric acid Step 1

4-[4-(9-Bromo-2-,3-dimethyl-naphtho[2,3-b]thiophen-4-yl)-2-cyclopentyl-phenoxy]-butyric acid methyl ester A solution of 2-cyclopentyl-4-(9-bromo-2,3-dimethyl-naphtho[2,3-b]thiophen-4-yl)-phenol (0.30 g, 0.81 mmol), 4-bromobutyric acid, methyl ester (1.5 mL, 13.0 mmol), 60% sodium hydride (0.09 g, 2.3 mmol), potassium carbonate (1.0 g, 7.2 mmol), and anhydrous benzene (2 mL) was heated at 100° for 36 h. Purification by chromatography with hexanes/ethyl acetate gave the title compound as a solid (0.23 g, 52%): NMR (DMSO-d6): δ8.18 (d, J=8 Hz, 1H), 7.62 (ddd, J=2,6,8 Hz, 1H), 7.50–7.41 (m, 2H), 7.16–7.04 (m, 3H), 4.11 (m, 2H), 3.63 (s, 3H), 3.31 (quint, J=8 Hz, 1H), 2.57 (t, J=7 Hz, 2H), 2.42 (s, 3H), 2.07 (quintet, J=7 Hz, 2H), 1.95 (m, 2H), 1.74–1.45 (m containing a singlet at δ1.56, 9H); MS(EI): [M+], 1 bromine isotope pattern, 550/552.

Step 2

4-[4-(9-Bromo-2-,3-dimethyl-naphtho[2,3-b]thiophen-4-yl)-2-cyclopentyl-phenoxy]-butyric acid In a manner similar to the procedure of Example 49, Step 7 there was obtained from 4-[4-(9-bromo-2-,3-dimethyl-naphtho[2,3-b]thiophen-4-yl)-2-cyclopentyl-phenoxy]-butyric acid methyl ester (0.23 g, 0.42 mmol), aqueous potassium hydroxide (1.66 mL of a 1 N solution, 1.66 mmol), tetrahydrofuran (9.2 mL), and enough methanol to create a homogeneous solution the title compound as an off-white solid (0.22 g, 100%): NMR (DMSO-d6): δ12.15 (br s, 1H), 8.18 (d, J=8 Hz, 1H), 7.62 (ddd, J=2,6,8 Hz, 1H), 7.51–7.41 (m, 2H), 7.14–7.05 (m, 3H), 4.10 (m, 2H), 3.37 (m, 1H), 2.48 (t, J=7 Hz, 1H), 2.41 (s, 3H), 2.04 (quintet, J=7 Hz, 2H), 1.96 (m, 2H), 1.72–1.44 (m containing a singlet at δ1.56, 9H); MS(–ESI): [M–H]⁻, 1 bromine isotope pattern, 535/537; Anal. Calc. for C29H29BrO3S: C, 64.80; H, 5.44; N, 0.00. Found: C, 64.20; H, 5.50; N, 0.03.

EXAMPLE 74

2-Cyclopentyl-4-(2-,3-dimethyl-naphtho[2,3-b]furan-4-yl)-phenol

In a manner similar to the procedure of Example 49, Step 1 there was obtained from 3-cyclopentyl-p-anisic acid (10 g, 45.4 mmol, RN-59216-82-9); oxalyl chloride (4.4 mL, 50.4 mmol), N,N-dimethylformamide (2 drops), 2,3-dimethyl-5-benzylfuran (10.1 g, 54.2 mmol), tin(IV) chloride (5.8 mL, 49.6 mmol), and anhydrous methylene chloride (183 mL) an oil (18.8 g), which was used without further purification.

In a manner similar to the procedure of Example 49, Step 2 there was obtained from (2-benzyl-4,5-dimethyl-furan-3-yl)-(3-cyclopentyl-4-methoxy-phenyl)-methanone (18.8 g, 48.4 mmol), boron tribromide (34.8 mL, 368 mmol), and methylene chloride (167 mL) at 50–55° for 2 h the title compound as a light tan solid (1.56 g, 9.6%): (DMSO-d6): δ9.46 (s, 1H), 7.96 (d, J=8 Hz, 1H), 7.90 (s, 1H), 7.54 (d, J=8 Hz, 1H), 7.39 (ddd, J=1, 7, 8 Hz, 1H), 7.29 (ddd, J=1, 7, 8 Hz, 1H), 7.04 (d, J=2 Hz, 1H), 6.97 (dd, J=2, 8 Hz, 2H), 6.91

(d, J=8 Hz, 1H), 3.38–3.26 (m, 1H), 2.36 (s, 3H), 1.96 (m, 2H), 1.74–1.44 (m containing a singlet at δ1.55, 9H); MS(EI): [M+] 356; Anal. Calc. for C25H24O2: C, 84.24; H, 6.79; N, 0.00. Found: C, 83.48; H, 6.71; N, 0.04.

EXAMPLE 75

Acetic acid 2-cyclopentyl-4-(2-,3-dimethyl-naphtho[2,3-b]furan-4-yl)-phenyl ester In a manner similar to the procedure of Example 49, Step 3 there was obtained from 2-cyclopentyl-4-(2,3-dimethyl-naphtho[2,3-b]furan-4-yl)-phenol (4.81 g, 13.5 mmol), acetic anhydride (1.60 mL, 17.0 mmol), pyridine (27 mL), and methylene chloride (27 mL) a residue, which was chromatographed with hexane/ethyl acetate to give the title compound as a solid (0.92 g, 17%): NMR (DMSO-d6): δ8.00 (d, J=8 Hz, 1H), 7.97 (s, 1H), 7.42 (ddd, J=1, 7, 8 Hz, 1H), 7.34 (ddd, J=1, 7, 8 Hz, 1H), 7.30 (d, J=2 Hz, 1H), 7.22 (dd, J=2, 8 Hz, 1H), 7.19 (d, J=8 Hz, 1H), 3.14 (m, 1H), 2.37 (s, 3H), 2.36 (s, 3H), 1.96 (m, 2H), 1.74–1.44 (m containing a singlet at δ1.52, 9H); MS(+ESI): [M+H]+399; Anal. Calc. for C27H26O3: C, 81.38; H, 6.58; N, 0.00. Found: C, 80.76; H, 6.65; N, 0.05. 5.24; N, 0.03.

EXAMPLE 76

(R)-2-[4-(2-,3-Dimethyl-naphtho[2,3-b]thiophen-4-yl)-2-ethyl-phenoxy]-3-phenyl-propionic acid In a manner similar to the procedure of Example 49, Step 6 there was obtained from 2-ethyl-4-(2,3-dimethyl-naphtho[2,3-b]thiophen-4-yl)-phenol (1.47 g, 4.42 mmol), (S)-2-hydroxy-3-phenylpropionic acid, methyl ester (4.78 g, 26.5 mmol), triphenylphosphine (6.96 g, 26.5 mmol), diethylazodicarboxylate (4.18 mL, 26.5 mmol), and anhydrous benzene (8.8 mL) a solid (0.16 g), which was used without further purification.

In a manner similar to the procedure of Example 49, Step 7 there was obtained from (R)-2-[4-(2-,3-dimethyl-naphtho[2,3-b]thiophen-4-yl)-2-ethyl-phenoxy]-3-phenyl-propionic acid methyl ester (0.16 g, 0.32 mmol), aqueous potassium hydroxide (0.65 mL of a 1 N solution, 0.65 mmol), tetrahydrofuran (3.2 mL), and enough methanol to create a homogeneous solution the title compound as a yellow foam (0.10 g, 63%): NMR (DMSO-d6): δ13.11 (br s, 1H), 8.43 (d, J=2 Hz, 1H), 7.93 (dd, J=3, 8 Hz, 1H), 7.48–7.20 (m, 8H), 7.10–7.00 (m, 2H), 6.86 (dd, J=4, 9 Hz, 1H), 5.08 and 5.04 (two dd, J=4, 8 Hz, atroph isomers, 1H), 3.42 (m, ABX pattern, 2H), 2.75–2.52 (complex m, ABX pattern, atroph isomers, 2H), 2.38 (s, 3H), 1.56 and 1.54 (two s, atroph isomers, 3H), 1.08 and 1.06 (two t, J=7 Hz, 3H); MS(EI): [M+], 480; Anal. Calc. for C31H28O3S: C, 77.47; H, 5.87; N, 0.00. Found: C, 74.55; H, 5.87, N, 0.20.

EXAMPLE 77

(R)-2-[4-(9-Bromo-2-,3-dimethyl-naphtho[2,3-b]thiophen-4-yl)-2-ethyl-phenoxy]-3-phenyl-propionic acid Step 1

Acetic acid 4-(2,3-dimethyl-naphtho[2,3-b]thiophen-4-yl)-2-ethyl-phenyl ester

In a manner similar to the procedure of Example 49, Step 3 there was obtained from 2-ethyl-4-(2,3-dimethyl-naphtho[2.3-b]thiophen-4-yl)-phenol (1.4 g, 4.2 mmol), acetic anhydride (0.52 mL, 5.5 mmol), and pyridine (8.4 mL) a residue, which was chromatographed with hexane/ethyl acetate to give the title compound as a solid (1.62 g, >100%): NMR (DMSO-d6): δ8.49 (s, 1H), 7.97 (d, J=9 Hz, 1H), 7.50–7.43 (m, 1H), 7.40–7.35 (m, 2H), 7.27 (s, 1H), 7.21 (s, 2H), 2.57 (two overlapping quartets, J=8 Hz, 2H), 2.40 (s, 3H), 2.37 (s, 3H), 1.58 (s, 3H), 1.13 (t, J=8 Hz, 3H); MS(EI): [M+] 374; Anal. Calc. for C24H22O2S: C, 76.97; H, 5.92; N, 0.00. Found: C, 75.72; H, 5.92; N, 0.03.

Step 2

Acetic acid 4-(9-bromo-2,3-dimethyl-naphtho[2,3-b]thiophen-4-yl)-2-ethyl-phenyl ester In a manner similar to the procedure of Example 49, Step 4 there was obtained from acetic acid 4-(2,3-dimethyl-naphtho[2,3-b]thiophen-4-yl)-2-ethyl-phenyl ester (1.53 g, 4.1 mmol), ferric chloride (41 mg, 0.22 mmol), bromine (0.23 mL, 4.5 mmol), and methylene chloride (35 mL) the title compound as a solid (0.48 g, 26%): NMR (DMSO-d6): δ8.21 (d, J=9 Hz, 1H), 7.65 (ddd, J=2, 6, 8 Hz, 1H), 7.57–7.40 (m, 2H), 7.30 (s, 1H), 7.23 (s, 2H), 2.56 (two overlapping quartets, J=8 Hz, 2H), 2.43 (s, 3H), 2.37 (s, 3H), 1.56 (s, 3H), 1.13 (t, J=8 Hz, 3H).

Step 3

4-(9-Bromo-2,3-dimethyl-naphtho[2,3-b]thiophen-4-yl)-2-ethyl-phenol

In a manner similar to the procedure of Example 49, Step 5 there was obtained from acetic acid 4-(9-bromo-2,3-dimethyl-naphtho[2,3-b]thiophen-4-yl)-2-ethyl-phenyl ester (1.5 g, 3.3 mmol), aqueous potassium hydroxide (4.0 mL of a 1 N solution, 4.0 mmol), tetrahydrofuran (55 mL), and methanol (37 mL) the title compound as a green foam (1.4 g, >100%): NMR (DMSO-d6): δ9.55 (s, 1H), 8.16 (d, J=9 Hz, 1H), 7.62 (ddd, J=1, 7, 8 Hz, 1H), 7.54 (d, J=8 Hz, 1H), 7.44 (ddd, J=1, 7, 8 Hz, 1H), 7.05–6.87 (m, 3H), 2.60 (complex m, ABX pattern, 2H), 2.41 (s, 3H), 1.59 (s, 3H), 1.13 (t, J=8 Hz, 3H).

Step 4

(2R)-2-[4-(9-Bromo-2,3-dimethyl-naphtho[2,3-b]thiophen-4-yl)-2-ethyl-phenoxy]3-phenyl-propionic acid methyl ester In a manner similar to the procedure of Example 49, Step 6 there was obtained from 4-(9-bromo-2,3-dimethyl-naphtho[2,3-b]thiophen-4-yl)-2-ethyl-phenol (0.45 g, 1.16 mmol), (S)-2-hydroxy-3-phenylpropionic acid, methyl ester (0.31 g, 1.72 mmol), triphenylphosphine (0.45 g, 1.72 mmol), diethylazodicarboxylate (0.27 mL, 1.71 mmol), and anhydrous benzene (5 mL) at 90° for 18 h the title compound as a glassy residue (0.22 g, 33%): NMR (DMSO-d6): δ8.22 (d, J=9 Hz, 1H), 7.66 (ddd, J=3, 6, 8 Hz, 1H), 7.59–7.22 (m, 7H), 7.20–7.02 (m, 2H), 6.92 (dd, J=2, 8 Hz, 1H), 5.31 (m, 1H), 3.74 and 3.70 (two s, atroph isomers, 3H), 3.32 (m, 2H), 2.64 (complex m, 2H), 2.45(s, 3H), 1.55 (s, 3H), 1.12 and 1.10 (two t, J=7 Hz, atroph isomers, 3H).

Step 5

(2R)-2-[4-(9-Bromo-2,3-dimethyl-naphtho[2,3-b]thiophen-4-yl)-2-ethyl-phenoxy]-3-phenyl-propionic acid In a manner similar to the procedure of Example 49, Step 7 there was obtained from (2R)-2-[4-(9-bromo-2,3-dimethyl-naphtho[2,3-b]thiophen-4-yl)-2-ethyl-phenoxy]-3-phenyl-propionic acid methyl ester (0.22 g, 0.38 mmol), aqueous potassium hydroxide (0.46 mL of a 1 N solution, 0.46 mmol), tetrahydrofuran (15 mL), and methanol (5 mL) the title compound as a white solid (0.19 g, 90%): Opt. Rot. [a]25/D=+1.55° (8.396 mg/mL, MeOH); NMR (DMSO-d6): δ13.15 (br s, 1H), 8.17 (dd, J=4, 9 Hz, 1H), 7.66–7.58 (m, 1H), 7.50–7.21 (m, 7H), 7.11–7.04 (m, 2H), 6.88 (dd, J=4, 9 Hz, 1H), 5.09 and 5.06 (two dd, J=4, 8 Hz, atroph isomers, 1H), 3.24 (complex m, ABX pattern, 2H), 2.66 and 2.56 (two overlapping doublet of quartets, ABX pattern, atroph isomers, 2H), 2.42 and 2.40 (two s, atroph isomers, 3H), 1.53 and 1.52 (two s, atroph isomers, 3H), 1.08 and 1.06 (two t, J=8 Hz, atroph isomers, 3H); MS(EI): [M+], 1 bromine isotope pattern, 558/560; Anal. Calc. for C31H27BrO3S: C, 66.54; H, 4.86; N, 0.00. Found: C, 66.91; H, 5.28; N, −0.07.

EXAMPLE 78

2-Bromo-4-(2-,3-dimethyl-naphtho[2,3-b]furan-4-yl)-6-ethyl-phenol

In a manner similar to the procedure of Example 49, Step 1 there was obtained from 3-bromo-5-ethyl-p-anisic acid (4.95 g, 19.1 mmol), oxalyl chloride (1.8 mL, 20.6 mmol), N,N-dimethylformamide (2 drops), 2,3-dimethyl-5-benzylfuran (4.3 g, 23.1 mmol), tin(IV) chloride (2.5 mL, 21.4 mmol), and anhydrous methylene chloride (72 mL) an oil (7.85 g), which was used without further purification.

In a manner similar to the procedure of Example 49, Step 2 there was obtained from (2-benzyl-4,5-dimethyl-furan-3-yl)-(3-bromo-5-ethyl-4-methoxy-phenyl)-methanone (7.85 g, 18.4 mmol), boron tribromide (13.2 mL, 14.0 mmol), and methylene chloride (63 mL) at 50° for 2 h the title compound as a white solid (0.85 g, 12%): (DMSO-d6): δ9.17 (s, 1H), 7.99 (d, J=8 Hz, 1H), 7.95 (s, 1H), 7.52 (d, J=8 Hz, 1H), 7.42 (ddd, J=1, 7, 8 Hz, 1H), 7.37–7.30 (m, 2H), 7.10 (d, J=2 Hz, 1H), 2.80–2.60 (complex m, ABX pattern, 2H), 2.37 (s, 3H), 1.59 (s, 3H), 1.15 (t, J=8 Hz, 3H); MS(EI): [M+], 1 bromine isotope pattern, 394/396; Anal. Calc. for C22H19BrO2: C, 66.85; H, 4.84; N, 0.00. Found: C, 67.07; H, 4.85; N, 0.05.

EXAMPLE 79

(R)-2-[2-Bromo-4-(2-,3-dimethyl-naphtho[2,3-b] furan-4-yl)-6-ethyl-phenoxy]-3-phenyl-propionic acid Step 1

(2R)-2-[2-Bromo-4-(2,3-dimethyl-naphtho[2,3-b] furan-4-yl)-6-ethyl-phenoxy]-3-phenyl-propionic acid methyl ester In a manner similar to the procedure of Example 49, Step 6 there was obtained from 2-bromo-4-(2,3-dimethyl-naphtho[2,3-b]furan-4-yl)-6-ethyl-phenol (0.30 g, 0.76 mmol), (S)-2-hydroxy-3-phenylpropionic acid, methyl ester (0.54 g, 3.0 mmol), triphenylphosphine (0.80 g, 3.1 mmol), diethylazodicarboxylate (0.48 mL, 3.0 mmol), and anhydrous benzene (1.0 mL) at 100° for 12 h the title compound as a solid (0.37 g, 88%): NMR (DMSO-d6): δ8.02 (d, J=8 Hz, 1H), 7.99 (s, 1H), 7.54–7.22 (m, 10H), 5.08 and 5.02 (two dd, J=6, 8 Hz, atroph isomers, 3H), 3.60 and 3.57 (two s, atroph isomers, 3H), 3.47–3.30 (m, 2H), 2.80–2.52 (complex m, ABX pattern, atroph isomers, 2H), 2.40 and 2.39 (two s, atroph isomers, 3H), 1.58 and 1.53 (two s, atroph isomers, 3H), 1.12 and 1.10 (two t, J=8 Hz, atroph isomers, 3H); MS(EI): [M+], 1 bromine isotope pattern, 556/558.

Step 2

(2R)-2-[2-Bromo-4-(2,3-dimethyl-naphtho[2,3-b] furan-4-yl)-6-ethyl-phenoxy]-3-phenyl-propionic acid In a manner similar to the procedure of Example 49, Step 7 there was obtained from (2R)-2-[2-bromo-4-(2,3-dimethyl-naphtho[2,3-b]furan-4-yl)-6-ethyl-phenoxy]-3-phenyl-propionic acid methyl ester (0.34 g, 0.61 mmol), aqueous potassium hydroxide (1.2 mL of a 1 N solution, 1.2 mmol), tetrahydrofuran (6.0 mL), and enough methanol to create a homogeneous solution the title compound as a white foam (0.31 g, 94%): NMR (DMSO-d6): δ8.01 (d, J=8 Hz, 1H), 7.97 (d, J=2 Hz, 1H), 7.48 (d, J=9 Hz, 2H), 7.46–7.22 (m, 9H), 7.20 (dd, J=2,6 Hz, 1H), 5.03 (m, 1H), 3.35 (m, 2H), 2.94–2.55 (complex m, ABX pattern, 2H), 2.38 and 2.36 (two s, atroph isomers, 3H), 1.56 and 1.51 (two s, atroph isomers, 3H), 1.11 and 1.10 (two t, J=7 Hz, atroph isomers, 3H); MS(EI): [M+], 1 bromine isotope pattern, 542/544; Anal. Calc. for C31H27BrO4: C, 68.51; H, 5.01; N, 0.00. Found: C, 68.22; H, 5.42; N, 0.10.

EXAMPLE 80

4-[2-Bromo-4-(2,3-dimethyl-naphtho[2,3-b]furan-4yl)-6-ethyl-phenoxy]-butyric acid Step 1

4-[2-Bromo-4-(2,3-dimethyl-naphtho[2,3-b]furan-4-yl)-6-ethyl-phenoxy]-butyric acid methyl ester A solution of 2-bromo-4-(2,3-dimethyl-naphtho[2,3-b] furan-4-yl)-6-ethyl-phenol (0.30 g, 0.76 mmol), 60% sodium hydride (33 mg, 0.83 mmol), 4-bromobutyric acid, methyl ester (0.44 mL, 3.82 mmol), and anhydrous benzene (1.0 mL) was heated at 100° for 6 h. A second portion of 4-bromobutyric acid methyl ester (0.45 mL, 3.91 mmol) and potassium carbonate (0.5 g, 3.62 mmol) was added and the reaction mixture was heated at 100° for 6 h. The crude reaction mixture was chromatographed with hexane/ethyl acetate to give the title compound as a solid (0.31 g, 82%): NMR (DMSO-d6): δ8.00 (d, J=8 Hz, 1H), 7.98 (s, 1H), 7.48 (d, J=8 Hz, 1H), 7.46 (d, J=2 Hz, 1H), 7.43 (ddd, J=1, 7, 8 Hz, 1H), 7.35 (ddd, J=1, 7, 8 Hz, 1H), 7.26 (d, J=2 Hz, 1H), 4.03 (dd, J=6, 9 Hz, 1H), 3.98 (dd, J=6, 9 Hz, 1H), 3.63 (s, 3H), 2.74 (d of quartets, J=7, 15 Hz, 1H), 2.69 (d of quartets, J=7, 15 Hz, 1H), 2.62 (t, J=7 Hz, 2H), 2.38 (s, 3H), 2.09 (quintet, J=7 Hz, 2H), 1.56 (s, 3H), 1.18 (t, J=7 Hz 3H); MS(EI): [M+], 1 bromine isotope pattern, 494/496.

Step 2

4-[2-Bromo-4-(2,3-dimethyl-naphtho[2,3-b]furan-4-yl)-6-ethyl-phenoxy]-butyric acid In a manner similar to the procedure of Example 49, Step 7 there was obtained from 4-[2-bromo-4-(2,3-dimethyl-naphtho[2,3-b]furan-4-yl)-6-ethyl-phenoxy]-butyric acid methyl ester (0.31 g, 0.63 mmol), aqueous potassium hydroxide (1.25 mL of a 1 N solution, 1.25 mmol), tetrahydrofuran (6.3 mL), and enough methanol to create a homogeneous solution the title compound as a white foam (0.26 g, 87%): NMR (DMSO-d6): δ12.15 (br s, 1H), 8.01 (d, J=8 Hz, 1H), 7.98 (s, 1H), 7.48 (d, J=8 Hz, 1H), 7.46 (d, J=2 Hz, 1H), 7.42 (ddd, J=1, 7, 8 Hz, 1H), 7.35 (ddd, J=1, 7, 8 Hz, 1H), 7.26 (d, J=2 Hz, 1H), 4.04 (dd, J=6, 9 Hz, 1H), 3.98 (dd, J=6, 9 Hz, 1H), 2.74 (d of quartets, J=7, 15 Hz, 1H), 2.71 (d of quartets, J=7, 15 Hz, 1H), 2.53 (t, J=7 Hz, 2H), 2.38 (s, 3H), 2.06 (quintet, J=7 Hz, 2H), 1.56 (s, 3H), 1.19 (t, J=7 Hz, 3H); MS(−ESI): [M−H]⁻, 1 bromine isotope pattern, 479/481; Anal. Calc. for C26H25BrO4: C, 64.87; H, 5.23; N, 0.00. Found: C, 64.94; H, 5.34; N, 0.08.

EXAMPLE 81

4-[2-Bromo-4-(2,3-dimethyl-naphtho[2,3-b]furan-4-yl)-6-ethyl-phenoxy]-butyramide 0.4 hydrate A solution of 4-[2-bromo-4-(2,3-dimethyl-naphtho[2,3-b] furan-4-yl)-6-ethyl-phenoxy]-butyric acid (60 mg, 0.12 mmol), oxalyl chloride (10.8 μL, 0.12 mmol), N,N-dimethylformamide (2.0 μL), and methylene chloride (1.0 mL) was stirred at room temperature. After 2.5 h a saturated solution of ammonia in acetonitrile (5 mL) was added and the resulting mixture was stirred at room temperature for 2 days. Concentration under reduced pressure gave a residue, which was suspended in 3% ethanol in water (31 mL) and stirred at room temperature for 18 h. The slurry was filtered, washed well with water, and air dried to give the title compound as an off-white solid (52.6 mg, 88%): NMR (DMSO-d6): δ8.00 (d, J=8 Hz, 1H), 7.98 (s, 1H), 7.49 (d, J=8 Hz, 1H), 7.45 (d, J=2 Hz, 1H), 7.43 (ddd, J=1, 7, 8 Hz, 1H), 7.35 (ddd overlapping with a br s, J=1, 7, 8 Hz, 2H), 7.25 (d, J=2 Hz, 1H), 6.79 (br s, 1H), 4.01 (dd, J=6, 9 Hz, 1H), 3.96 (dd, J=6, 9 Hz, 1H), 2.75 (d of quartets, J=7, 15 Hz, 1H), 2.71 (d of quartets, J=7, 15 Hz, 1H), 2.38 (s, 3H), 2.35 (t, J=7 Hz, 2H), 2.04 (quintet, J=7 Hz, 2H), 1.56 (s, 3H), 1.19 (t, J=7 Hz, 3H); MS(+ESI): [M+H]+, 1 bromine isotope pattern, 480/482; Anal. Calc. for C26H26BrNO3Y0.4H2O: C, 64.04; H, 5.54; N, 2.87. Found: C, 64.01; H, 5.43; N, 2.89.

EXAMPLE 82

4-(2,3-Dimethyl-naphtho[2,3-b]furan-4-yl)-2-ethyl-phenol

Step 1

(2-Benzyl-4,5-dimethyl-furan-3-yl)-(4-methoxy-3-ethyl-phenyl)-methanone

In a manner similar to the procedure of Example 49, Step 1 there was obtained from 3-ethyl-p-anisic acid (5.0 g, 27.7 mmol), oxalyl chloride (2.7 mL, 31.0 mmol), N,N-dimethylformamide (2 drops), 2,3-dimethyl-5-benzylfuran (6.2 g, 33.3 mmol), tin(IV) chloride (3.6 mL, 30.8 mmol), and anhydrous methylene chloride (177 mL) the title compound as an oil (7.24 g, 75%): (DMSO-d6): δ7.61 (dd, J=2, 8 Hz, 1H), 7.54 (d, J=2 Hz, 1H), 7.28–7.13 (m, 3H), 7.09–7.03 (m, 3H), 3.86 (s, 3H), 3.82 (s, 2H), 2.55 (q, J=7 Hz, 2H), 2.16 (s, 3H), 1.78 (s, 3H), 1.08 (t, J=7 Hz, 3H).

Step 2

4-(2,3-Dimethyl-naphtho[2,3-b]furan-4-yl)-2-ethyl-phenol

In a manner similar to the procedure of Example 49, Step 2 there was obtained from (2-benzyl-4,5-dimethyl-furan-3-yl)-(4-methoxy-3-ethyl-phenyl)-methanone (7.0 g, 20.1 mmol), boron tribromide (14.4 mL, 152.3 mmol), and methylene chloride (69 mL) the title compound as an off-white solid (0.61 g, 9.6%): (DMSO-d6): δ9.45 (s, 1H), 7.97 (d, J=8 Hz, 1H), 7.90 (s, 1H), 7.55 (d, J=8 Hz, 1H), 7.39 (ddd, J=1, 7, 8 Hz, 1H), 7.29 (ddd, J=1, 7, 8 Hz, 1H), 7.02 (d, J=2 Hz, 1H), 6.98 (dd, J=2, 8 Hz, 1H), 6.91 (d, J=8 Hz, 1H), 2.63 (d of quartets, J=7, 14 Hz, 1H), 2.58 (d of quartets, J=7, 14 Hz, 1H), 2.36 (s, 3H), 1.56 (s, 3H), 1.14 (t, J=7 Hz, 3H); MS(EI): [M+] 316.

EXAMPLE 83

(R)-2-[4-(9-Bromo-2-,3-dimethyl-naphtho[2,3-b]thiophen-4-yl)-2-propyl-phenoxy]-3-phenyl-propionic acid Step 1

(2-Benzyl-4,5-dimethyl-thiophen-3yl)-(4-methoxy-3-propyl-phenyl)-methanone

In a manner similar to the procedure of Example 49, Step 1 there was obtained from 3-propyl-p-anisic acid (3.0 g, 15.4 mmol), oxalyl chloride (1.48 mL, 17.0 mmol), N,N-dimethylformamide (2 drops), 2,3-dimethyl-5-benzylthiophene (3.75 g, 18.5 mmol), tin(IV) chloride (1.99 mL, 17.0 mmol), and anhydrous methylene chloride (99 mL) the title compound as an oil (2.11 g, 38%): (DMSO-d6): δ7.58 (dd, J=2, 8 Hz, 1H), 7.53 (d, J=2 Hz, 1H), 7.25–7.11 (m, 3H), 7.10–7.03 (m, 3H), 3.86 (s, 3H), 3.84 (s, 2H), 2.54 (t, J=7 Hz, 2H), 2.26 (s, 3H), 1.81 (s, 3H), 1.51 (sextet, J=7 Hz, 2H), 0.87 (t, J=7 Hz, 3H); MS(EI): [M+] 378.

Step 2

4-(2,3-Dimethyl-naphtho[2,3-b]thiophen-4yl)-2-propyl-phenol

In a manner similar to the procedure of Example 49, Step 2 there was obtained from (2-benzyl-4,5-dimethyl-thiophen-3-yl)-(4-methoxy-3-propyl-phenyl)-methanone (2.70 g, 7.1 mmol), boron tribromide (5.12 mL, 54.2 mmol), and methylene chloride (24.5 mL) the title compound as a solid (1.77 g, 71%): (DMSO-d6): δ 9.44 (s, 1H), 8.42 (s, 1H), 7.93 (d, J=8 Hz, 1H), 7.50–7.25 (m, 3H), 7.05–6.88 (m, 3H), 2.61 (m, 1H), 2.52 (m, 1H), 2.39 (s, 3H), 1.70–1.50 (m containing a singlet at δ1.63, 5H), 0.88 (t, J=7 Hz, 3H); MS(EI): [M+] 346.

Step 3

Acetic acid 4-(2,3-dimethyl-naphtho[2,3-b]thiophen-4-yl)-2-propyl-phenyl ester

In a manner similar to the procedure of Example 49, Step 3 there was obtained from 4-(2,3-dimethyl-naphtho[2,3-b]thiophen-4-yl)-2-propyl-phenol (1.3 g, 3.8 mmol), acetic anhydride (0.46 mL, 4.9 mmol), and pyridine (7.5 mL) a residue, which was chromatographed with hexane/ethyl acetate to give the title compound as a solid (0.81 g, 56%): NMR (DMSO-d6): δ8.50 (s, 1H), 7.98 (d, J=9 Hz, 1H), 7.51–7.44 (m, 1H), 7.40–7.36 (m, 2H), 7.26 (s, 1H), 7.23 (s, 2H), 2.55 (m, 2H), 2.42 (s, 3H), 2.38 (s, 3H), 1.64–1.53 (m containing a singlet δ1.61, 5H), 0.88 (t, J=7 Hz, 3H); MS(EI): [M+] 388.

Step 4

Acetic acid 4-(9-bromo-2,3-dimethyl-naphtho[2,3-b]thiophen-4-yl)-2-propyl-phenyl ester In a manner similar to the procedure of Example 49, Step 4 there was obtained from acetic acid 4-(2,3-dimethyl-naphtho[2,3-b]thiophen-4-yl)-2-propyl-phenyl ester (0.80 g, 2.1 mmol), ferric chloride (16.7 mg, 0.10 mmol), bromine (0.12 mL, 2.3 mmol), and methylene chloride (21 mL) the title compound as a solid (0.38 g, 39%): NMR (DMSO-d6): δ8.20 (d, J=9 Hz, 1H), 7.65 (ddd, J=1, 6, 8 Hz, 1H), 7.48 (ddd, J=1, 6, 8 Hz, 1H), 7.43 (d, J=8 Hz, 1H), 7.28 (s, 1H), 7.23 (s, 2H), 2.53 (m, 2H), 2.43 (s, 3H), 2.36 (s, 3H), 1.63–1.50 (m containing a singlet at δ1.57, 5H), 0.86 (t, J=7 Hz, 3H); MS(EI): [M+], 1 bromine isotope pattern, 466/468.

Step 5

(2R)-2-[4-(9-Bromo-2,3-dimethyl-naphtho[2,3-b]thiophen-4-yl)-2-propyl-phenoxy]-3-phenyl-propionic acid In a manner similar to the procedure of Example 49, Step 5 there was obtained from acetic acid 4-(9-bromo-2,3-dimethyl-naphtho[2,3-b]thiophen-4-yl)-2-propyl-phenyl ester (0.36 g, 0.77 mmol), aqueous potassium hydroxide (0.92 mL of a 1 N solution, 0.92 mmol), tetrahydrofuran (11.4 mL), and methanol (7.6 mL) a solid, 4-(9-bromo-2,3-dimethyl-naphtho[2,3-b]thiophen-4-yl)-2-propyl-phenol (0.62 g), which was used without further purification.

In a manner similar to the procedure of Example 49, Step 6 there was obtained from 4-(9-bromo-2,3-dimethyl-naphtho[2,3-b]thiophen-4-yl)-2-propyl-phenol (0.77 mmol), (S)-2-hydroxy-3-phenylpropionic acid, methyl ester (1.12 g, 6.2 mmol), triphenylphosphine (1.60 g, 6.1 mmol), diethylazodicarboxylate (0.96 mL, 6.1 mmol), and anhydrous benzene (2.5 mL) at 85° for 3 days a solid, (2R)-2-[4-(9-bromo-2,3-dimethyl-naphtho[2,3-b]thiophen-4-yl)-2-propyl-phenoxy]-3-phenyl-propionic acid methyl ester (0.23 g), which was used without further purification.

In a manner similar to the procedure of Example 49, Step 7 there was obtained from (2R)-2-[4-(9-bromo-2,3-dimethyl-naphtho[2,3-b]thiophen-4-yl)-2-propyl-phenoxy]-3-phenyl-propionic acid methyl ester (0.23 g, 0.39 mmol), aqueous potassium hydroxide (0.93 mL of a 1 N solution, 0.93 mmol), tetrahydrofuran (4.6 mL), and enough methanol to create a homogeneous solution the title compound as a yellow foam (0.17 g, 74%): NMR (DMSO-d6): $\delta$13.15 (br s, 1H), 8.18 (d, J=3, 9 Hz, 1H), 7.67–7.59 (m, 1H), 7.50–7.23 (m, 7H), 7.52–7.40 (m, 2H), 6.88 (dd, J=5, 8 Hz, 1H), 5.15–5.02 (m, 1H), 3.24 (m, 2H), 2.73–2.53 (m, 2H), 2.42 (s, 3H), 1.60–1.40 (m containing two singlets at $\delta$1.56 and 1.54, atroph isomers, 5H), 0.87 and 0.85 (two t, J=7 Hz, atroph isomers, 3H); MS(EI): [M+], 1 bromine isotope pattern, 572/574.

EXAMPLE 84

[9-Bromo-4-(4-methoxy-3,5-dimethylphenyl)-3-methylnaphtho[2,3-b]thien-2-yl]methyl acetate A solution of 4-(9-bromo-2,3-dimethyl-naphtho[2,3-b]thiophen-4-yl)-2,6-dimethyl-anisole (2.0 g, 4.7 mmol), sulfuryl chloride (0.42 mL, 5.3 mmol), diisopropylethylamine (0.90 mL, 5.2 mmol), and anhydrous methylene chloride (24 mL) was stirred at 0° C. for approximately 2 h. The crude reaction mixture was then diluted with diethyl ether, washed twice with water, once with brine, and then dried (Na2SO4). Concentration under reduced pressure gave a residue, which was immediately treated with sodium acetate (1.2 g, 14.6 mmol) and N,N-dimethylformamide (16.8 mL). After 24 h the reaction mixture was diluted with diethyl ether, washed three times with water, once with brine, and then dried (Na2SO4). Concentration under reduced pressure gave a residue, which was chromatographed with hexane/ethyl acetate to give the title compound as a yellow foam (0.36 g, 27%): (DMSO-d6): $\delta$8.41 (s, 1H), 8.21 (d, J=9 Hz, 1H), 7.68 (ddd, J=2, 6, 8 Hz, 1H), 7.57–7.45 (m, 2H), 7.05 (s, 2H), 3.78 (s, 3H), 2.30 (s, 6H), 2.08 (s, 3H), 1.68 (s, 3H); MS(EI): [M+], 1 bromine isotope pattern, 482/484; Anal. Calc. for C25H23BrO3S: C, 62.11; H, 4.80; N, 0.00. Found: C, 61.86; H, 4.75; N, 0.04.

EXAMPLE 85

4-(9-Bromo-2,3-dimethyl-naphtho[2,3-b]thien-4-yl)-2-methyl-phenyl acetate

Step 1

Acetic acid 4-(2,3-dimethyl-naphtho[2,3-b]thiophen-4-yl)-2-methyl-phenyl ester

In a manner similar to the procedure of Example 49, Step 1 there was obtained from 3-methyl-p-anisic acid (10 g, 60.2 mmol), oxalyl chloride (5.77 mL, 66.1 mmol), N,N-dimethylformamide (2 drops), 2,3-dimethyl-5-benzylthiophene (14.6 g, 72.2 mmol), tin(IV) chloride (7.75 mL, 66.2 mmol), and anhydrous methylene chloride (300 mL) an oil (24.4 g), which was used without further purification.

In a manner similar to the procedure of Example 49, Step 2 there was obtained from (2-benzyl-4,5-dmethyl-thiophen-3-yl)-(4-methoxy-3-methyl-phenyl)-methanone (24.4 g), boron tribromide (17.1 mL, 180.9 mmol), and methylene chloride (120 mL) a residue. This residue was treated with acetic anhydride (7.4 mL, 78.4 mmol), pyridine (58 mL), and methylene chloride (400 mL) in a manner similar to the procedure of Example 49, Step 3. The usual work up gave the title compound as a solid (9.83 g, 45.5%): NMR (DMSO-d6): $\delta$8.48 (s, 1H), 7.97 (d, J=8 Hz, 1H), 7.50–7.33 (m, 3H), 7.27 (s, 1H), 7.21 (s, 2H), 2.40 (s, 3H), 2.36 (s, 3H), 2.19 (s, 3H), 1.58 (s, 3H); MS(+APCI): [M+H] 361.

Step 2

4-(9-Bromo-2,3-dimethyl-naphtho[2,3-b]thien4-yl)-2-methyl-phenyl acetate

In a manner similar to the procedure of Example 49, Step 4 there was obtained from acetic acid 4-(2,3-dimethyl-naphtho[2,3-b]thiophen-4yl)-2-methyl-phenyl ester (5.0 g, 13.9 mmol), ferric chloride (0.11 g, 0.68 mmol), bromine (14.3 mL of a 1.07 M solution in carbon tetrachloride, 15.3 mmol), and methylene chloride (63 mL) the title compound as a solid (5.44 g, 90.7%): NMR (DMSO-d6): $\delta$8.20 (d, J=9 Hz, 1H), 7.65 (ddd, J=2, 6, 8 Hz, 1H), 7.52–7.42 (m, 2H), 7.30 (s, 1H), 7.23 (s, 2H), 2.43 (s, 3H), 2.36 (s, 3H), 2.20 (s, 3H). 1.56 (s, 3H); MS(EI): [M+], 1 bromine isotope pattern, 438/440; Anal. Calc. for C23H19BrO2S: C, 62.87; H, 4.36; N, 0.00. Found: C, 62.27; H, 3.99; N, 0.10.

EXAMPLE 86

Acetic acid 4-(9-bromo-2-diethylaminomethyl-3-methyl-naphtho[2,3-b]thiophen-4-yl)-2,6-dimethyl-phenyl ester Step 1

Acetic acid 4-(9-bromo-2-bromomethyl-3-methyl-naphtho[2,3-b]thiophen-4-yl)-2,6-dimethyl-phenyl ester In a manner similar to the procedure of Example 49, Step 4 there was obtained from acetic acid 4-(2-diethylaminomethyl-3-methyl-naphtho[2,3-b]thiophen-4-yl)-2,6-dimethyl-phenyl ester (10.0 g, 26.7 mmol), ferric chloride (0.23 g, 1.42 mmol), bromine (1.51 mL in methylene chloride (38 mL), 29.4 mmol), and methylene chloride (231 mL) acetic acid 4-(9-bromo-2,3-dimethyl-naphtho[2,3-b]thiophen-4-yl)-2,6-dimethyl-phenyl ester (6.68 g, 55%) and the title compound as a yellow solid (1.60 g): NMR (DMSO-d6): $\delta$8.28 (m, 1H), 7.62–7.56 (m, 2H), 7.41–7.37 (m, 1H), 7.06 (s, 2H), 4.70 (s, 2H), 2.42 (s, 3H), 2.24 (s, 6H), 1.72 (s, 3H); MS(EI): [M+], 2 bromine isotope pattern, 530/532/534; Anal. Calc. for C24H20Br2O2S: C, 54.15; H, 3.79; N, 0.00. Found: C, 53.81; H, 3.61; N, 0.10.

Step 2

Acetic acid 4-(9-bromo-2-diethylaminomethyl-3-methyl-naphtho[2,3-b]thiophen-4-yl)-2,6-dimethyl-phenyl ester Acetic acid 4-(9-bromo-2-bromomethyl-3-methyl-naphtho[2,3-b]thiophen-4-yl)-2,6-dimethyl-phenyl ester (1.21 g, 2.27 mmol) was treated with diethylamine (0.71 mL, 6.82 mmol), potassium carbonate (0.94 g, 6.82 mmol), and N,N-dimethylformamide (12.1 mL). After 1 h at room temperature the reaction mixture was poured in water (250 mL), filtered, and rinsed well with water. Air drying gave the title compound as a yellow solid (1.13 g, 94.5%): NMR (DMSO-d6): δ8.19 (d, 1H), 7.66–7.61 (m, 1H), 7.47 (d, 2 H), 7.13 (s, 2H), 3.73 (s, 2H), 2.58–2.52 (q, 4H), 2.40 (s, 3H), 2.16 (s, 6H), 1.61 (s, 3H), 1.02 (t, 6H); MS(EI): [M+], 1 bromine isotope pattern, 523/525; Anal. Calc. for C28H30BrNO2S: C, 64.12; H, 5.77; N, 2.67. Found: C, 63.30, H, 5.67; N, 2.55.

EXAMPLE 87

2-[4-(9-Bromo-2-diethylaminomethyl-3-methyl-naphtho[2,3-b]thiophen-4-yl)-2,6-dimethyl-phenoxy]-3-phenyl-propionic acid Step 1

4-(9-Bromo-2-diethylaminomethyl-3-methyl-naphtho[2,3-b]thiophen-4-yl)-2,6-dimethyl-phenol In a manner similar to the procedure of Example 49, Step 5 there was obtained from acetic acid 4-(9-bromo-2-diethylaminomethyl-3-methyl-naphtho[2,3-b]thiophen4-yl)-2,6-dimethyl-phenyl ester (1.13 g, 2.15 mmol), aqueous potassium hydroxide (2.58 mL of a 1 N solution, 2.58 mmol), tetrahydrofuran (28 mL), and methanol (19 mL) the title compound as a yellow solid (1.0 g, 961%): NMR (DMSO-d6): δ8.47 (s, 1H), 8.17 (d, 1H), 7.64–7.59 (m, 1H), 7.55–7.45 (m, 1H), 7.45–7.39 (m, 1H), 6.90 (s, 2H), 3.72 (s, 2H), 2.60–2.50 (m, 4H), 2.23 (s, 6H), 1.64 (s, 3H), 1.01 (m, 6H).

Step 2

(2R)-2-[4-(9-Bromo-2-diethylaminomethyl-3-methyl-naphtho[2,3-b]thiophen-4-yl)-2,6-dimethyl-phenoxy]-3-phenyl-propionic acid methyl ester In a manner similar to the procedure of Example 49, Step 6 there was obtained from 4-(9-bromo-2-diethylaminomethyl-3-methyl-naphtho[2,3-b]thiophen-4-yl)-2,6-dimethyl-phenol (0.90 g, 1.87 mmol), (S)-2-hydroxy-3-phenylpropionic acid, methyl ester (0.67 g, 3.73 mmol), triphenylphosphine (0.98 g, 3.73 mmol), diethylazodicarboxylate (0.59 mL, 3.73 mmol), and anhydrous benzene (10 mL) at 87° C. for 6 h gave the title compound as a solid (0.46 g, 38%): NMR (DMSO-d6): δ8.19 (d, 1H), 7.66–7.61 (m, 1H), 7.47–7.45 (m, 2H), 7.34 (d, 4H), 7.32–7.26 (m, 1H), 7.00 (d, 2H), 4.80 (t, 1H), 3.74 (s, 2H), 3.58 (s, 3H), 3.36–3.25 (m, 2H), 2.55 (q, 4H), 2.24 (s, 3H), 2.19 (s, 3H), 1.59 (s, 3H), 1.03 (t, 6H); MS(+ESI): [M+H]+, 1 bromine isotope pattern, 644/646; Anal. Calc. for C36H38BrNO3S: C, 67.07 H, 5.94; N, 2.17. Found: C, 66.73; H, 5.93; N, 2.15.

Step 3

(2R)-2-[4-(9-Bromo-2-diethylaminomethyl-3-methyl-naphtho[2,3-b]thiophen-4yl)-2,6-dimethyl-phenoxy]-3-phenyl-propionic acid In a manner similar to the procedure of Example 49, Step 7 there was obtained from (2R)-2-[4-(9-bromo-2-diethylaminomethyl-3-methyl-naphtho[2,3-b]thiophen-4-yl)- 2,6-dimethyl-phenoxy]-3-phenyl-propionic acid methyl ester (0.35 g, 0.98 mmol), aqueous potassium hydroxide (1.95 mL of a 1 N solution, 1.95 mmol), tetrahydrofuran (9 mL), and methanol (3 mL) the title compound as a solid (0.35 g, >100%): NMR (DMSO-d6): δ12.90 (br s, 1H), 8.19 (d, 1H), 7.66–7.61 (m, 1H), 7.50–7.43 (m, 2H), 7.37–7.31 (m, 4H), 7.28–7.24 (m, 1H), 7.00 (s, 2H), 4.72 (t, 1H), 3.74 (s, 2H), 3.38–3.25 (m, 2H), 2.60–2.53(q, 4H), 2.26 (s, 3H), 2.23 (s, 3H), 1.60 (s, 3H), 1.02 (t, 6H); MS(-ESI): [M$^{-H}$]−, 1 bromine isotope pattern, 628/630; Anal. Calc. for C35H36BrNO3S: C, 66.66; H, 5.75; N, 2.22. Found: C, 66.95; H, 5.99; N, 2.26.

EXAMPLE 88

(2R)-2-[4-(9-Bromo-2-diethylaminomethyl-3-methyl-naphtho[2,3-b]thiophen-4-yl)-2,6-diisopropyl-phenoxy]-3-phenyl-propionic acid This compound was prepared in a manner similar to Example 87 using appropriate starting materials to afford the title compound as a yellow solid: (DMSO-d6): δ13.00 (br s, 1H), 8.18 (d, 1H), 7.63–7.60 (m, 1H), 7.46–7.44 (m, 2H), 7.36–7.24 (m, 5H), 7.06 (s, 2H), 4.46 (t, 1H), 3.71 (s, 2H), 3.38–3.34 (m, 2H), 3.25 (d, 2H), 2.54 (q, 4H), 1.52 (s, 3H), 1.13 (d, 6H), 1.06 (d, 6H), 1.00 (t, 6H); MS(-ESI): [M−H]−, 1 bromine isotope pattern, 684/686; Anal. Calc. for C39H44BrNO3S: C, 68.21; H, 6.46; N, 2.04. Found: C, 68.04; H, 6.52; N, 1.92; Analytical HPLC indicates a major component (97.4%).

What is claimed is:

1. A compound of formula I having the structure

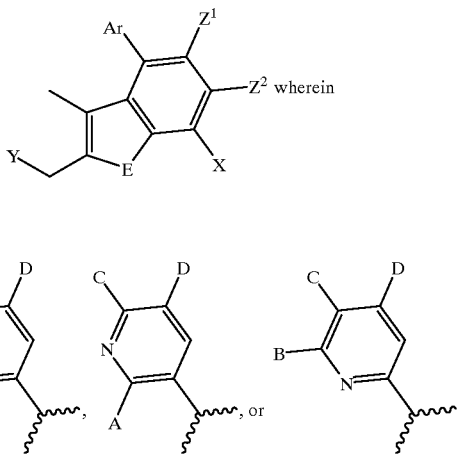

(I)

wherein

Ar is

A is hydrogen, halogen, or OH;

B and D are each, independently, hydrogen, halogen, CN, alkyl of 1–6 carbon atoms, aryl, aralkyl of 6–12 carbon atoms, hydroxyalkyl of 1–6 carbon atoms, hydroxyalkyl of 6–12 carbon atoms, cycloalkyl of 3–8 carbon atoms, nitro, amino, —NR$^1$R$^{1a}$, —NR$^1$COR$^{1a}$, —NR$^1$CO$_2$R$^{1a}$, cycloalkylamino of 3–8 carbon atoms, morpholino, furan-2-yl, furan-3-yl, thiophen-2-yl, thiophen-3-yl, —COR$^{1b}$ or OR;

R is hydrogen, alkyl of 1–6 carbon atoms, —COR$^1$, —(CH$_2$)$_n$CO$_2$R$^1$, —CH(R$^{1a}$)CO$_2$R$^1$, —SO$_2$R$^1$, —(CH$_2$)$_m$CH(OH)CO$_2$R$^1$, —(CH$_2$)$_m$COCO$_2$R$^1$, —(CH$_2$)$_m$CH=CHCO$_2$R$^1$, or —(CH$_2$)$_m$O(CH$_2$)$_o$CO$_2$R$^1$;

R$^1$ is hydrogen, alkyl of 1–6 carbon atoms, aralkyl of 6–12 carbon atoms, aryl, or CH$_2$CO$_2$R$^{1'}$;

R$^{1'}$ is hydrogen or alkyl of 1–6 carbon atoms

E is S, SO, SO$_2$, or O;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyalkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, —$OCH_2CO_2R^{2b}$ or —$COR^{2c}$;

Y is hydrogen, halogen, alkyl of 1–6 carbon atoms, aryl, aralkyl of 6–12 carbon atoms, hydroxyalkyl of 1–6 carbon atoms, hydroxyalkyl of 6–12 carbon atoms, —$OR^3$, $SR^3$, $NR^3R^{3a}$, —$COR^{3b}$, morpholine or piperidine;

$R^{1a}$, $R^2$, $R^{2a}$, $R^3$, $R^{3a}$ are each, independently, hydrogen, alkyl of 1–6 carbon atoms, aralkyl of 6–12 carbon atoms, or aryl;

$R^{1b}$ is alkyl of 1–6 carbon atoms or aryl;

$R^{2b}$ is hydrogen, alkyl of 1–6 carbon atoms;

$R^{2c}$ and $R^{3b}$ are each, independently, alkyl of 1–6 carbon atoms, aryl, or aralkyl of 6–12 carbon atoms;

C is hydrogen, halogen or $OR^4$;

$R^4$ is hydrogen, alkyl of 1–6 carbon atoms, —$CH(R_5)W$, —$C(CH_3)_2CO_2R^6$, 5-thiazolidine-2,4-dione, —$CH(R^7)(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_pCH=CHCO_2R^6$, or —$(CH2)_pO(CH_2)_qCO_2R^6$;

$R^5$ is hydrogen, alkyl of 1–6 carbon atoms, aralkyl of 6–12 carbon atoms, aryl, —$CH_2(1H$-imidazol-4-yl), —$CH_2(3$-1H-indolyl), —$CH_2CH_2(1,3$-dioxo-1,3-dihydro-isoindol-2-yl), —$CH_2CH_2(1$-oxo-1,3-dihydro-isoindol-2-yl), —$CH_2(3$-pyridyl), —$CH_2CO_2H$, or —$(CH_2)_nG$;

G is $NR^{6a}R^{7a}$, $NR^{6a}COR^{7a}$,

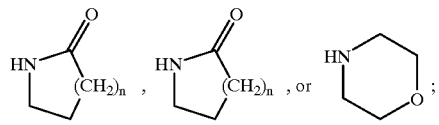

W is $CO_2R^6$, $CONH_2$, $CONHOH$, $CN$, $CONH(CH_2)_2CN$, 5-tetrazole, —$PO_3(R^6)_2$, —$CH_2OH$, —$CONR^{6b}CHR^{7b}$, —$CH_2NR^{6b}CHR^{7b}CO_2R^6$; —$CH_2OCHR^{7b}CO_2R^6$—$CH_2Br$, or —$CONR^{6b}CHR^{7b}CO_2R^6$;

$R^6$, $R^{6a}$, $R^7$, $R^{7a}$ are each, independently, is hydrogen, alkyl of 1–6 carbon atoms, or aryl; $R^{6b}$ is hydrogen or —$COR^{6c}$;

$R^{6c}$ is alkyl of 1–6 carbon atoms or aryl;

$R^{7b}$ is hydrogen, alkyl of 1–6 carbon atoms, or hydroxyalkyl of 1–6 carbon atoms;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —$CH=CR^9$—$CR^{10}=CR^{11}$—;

$R^8$ is hydrogen, alkyl of 1–6 carbon atoms, or aryl;

$R^9$, $R^{10}$, and $R^{11}$ are each, independently, hydrogen, alkyl of 1–6 carbon atoms, aryl, halogen, hydroxy, or alkoxy of 1–6 carbon atoms;

m is 1 to 4;
n is 1 or 2;
p is 1 to 4;
q is 1 to 4;
with the proviso that when E is O, Y is hydrogen, Ar is

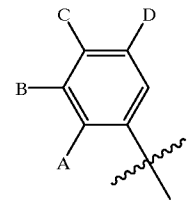

and A, B, C, and D are hydrogen,
then $Z^1$, $Z^2$, and X are not all hydrogen,
or a pharmaceutically acceptable salt thereof.

2. The compound according to claim 1, wherein

Ar is 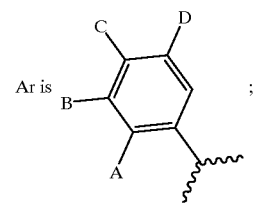

A is hydrogen or halogen
B and D are each, independently, hydrogen, halogen, CN, alkyl of 1–6 carbon atoms, aryl, aralkyl of 6–12 carbon atoms, branched alkyl, cycloalkyl of 3–8 carbon atoms, nitro or OR;

R is hydrogen or alkyl of 1–6 carbon atoms;

E is S, or O;

X is hydrogen, halogen, alkyl of 1–6 carbon atoms, CN, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino, morpholino, alkylsulfanyl of 1–6 carbon atoms, arylsulfanyl, pyridylsulfanyl, or 2-N,N-dimethylaminoethylsulfanyl;

$R^1$, $R^{1a}$, $R^2$, $R^{2a}$, $R^3$, and $R^{3a}$ are each, independently, hydrogen, alkyl of 1–6 carbon atoms, aralkyl of 6–12 carbon atoms, or aryl;

Y is hydrogen, halogen, $OR^3$, $SR^3$, $NR^3R^{3a}$, or morpholine;

C is hydrogen, halogen, or $OR^4$;

$R^4$ is hydrogen, alkyl of 1–6 carbon atoms, —$CH(R^5)W$, —$C(CH_3)_2CO_2R^6$, 5-thiazolidine-2,4-dione, —$CH(R^7)(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_pCH=CHCO_2R^6$, —$(CH_2)_pO(CH_2)_qCO_2R^6$;

$R^5$ is hydrogen, alkyl of 1–6 carbon atoms, aralkyl of 6–12 carbon atoms, aryl, —$CH_2(1H$-imidazol-4-yl), —$CH_2(3$-1H-indolyl), —$CH_2CH_2(1,3$-dioxo-1,3-dihydro-isoindol-2-yl), —$CH_2CH_2(1$-oxo-1,3-dihydro-isoindol-2-yl), or —$CH_2(3$-pyridyl);

W is $CO_2R^6$, —$CONH_2$, —$CONHOH$, 5-tetrazole, or —$CONR^{6b}CHR^{7b}CO_2R^6$;

$R^6$, $R^{6a}$, $R^{6b}$, $R^7$, $R^{7a}$, and $R^{7b}$ are each, independently, hydrogen, alkyl of 1–6 carbon atoms, or aryl;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —NR$^1$R$^{1a}$, —NR$^1$COR$^{1a}$, cycloalkylamino of 3–8 carbon atoms, morpholino, or OR$^8$, or Z$^1$ and Z$^2$ may be taken together as a diene unit having the formula —CH═CR$^9$—CR$^{10}$═CH—;

R$^9$ and R$^{10}$ are each, independently, hydrogen, or alkyl of 1–6 carbon atoms;

p is 1 to 4;

q is 1 to 4;

or a pharmaceutically acceptable salt thereof.

3. The compound according to claim 2, wherein

A is hydrogen;

B and D are each, independently, halogen, alkyl of 1–6 carbon atoms, aryl, aralkyl of 6–12 carbon atoms, or cycloalkyl of 3–8 carbon atoms;

E is S or O;

X is hydrogen, halogen, alkyl of 1–6 carbon atoms, perfluoroalkyl of 1–6 carbon atoms, CN, alkoxy of 1–6 carbon atoms, aryloxy, arylalkoxy of 6–12 carbon atoms, arylsulfanyl;

Y is hydrogen, —NR$^1$R$^2$, or morpholine;

R$^1$ and R$^2$ are each, independently, hydrogen or alkyl of 1–6 carbon atoms, aralkyl of 6–12 carbon atoms, or aryl;

C is OR$^4$;

R$^4$ is hydrogen, alkyl of 1–6 carbon atoms, —CH(R$^5$)W, or 5-thiazolidine-2,4-dione;

R$^5$ is hydrogen, alkyl of 1–6 carbon atoms, aralkyl of 6–12 carbon atoms, aryl, —CH$_2$(3-1H-indolyl), —CH$_2$CH$_2$(1,3-dioxo-1,3-dihydro-isoindol-2-yl), or —CH$_2$CH$_2$(1-oxo-1,3-dihydro-isoindol-2-yl);

W is —CO$_2$R$^6$, —CONH$_2$, —CONHOH, 5-tetrazole, —PO$_3$(R$^6$)$_2$, or —CONR$^6$CHR$^6$CO$_2$R$^6$;

R$^6$ is hydrogen or alkyl of 1–6 carbon atoms;

Z$^1$ and Z$^2$ are taken together as a diene unit having the formula —CH═CH—H═CH—;

or a pharmaceutically acceptable salt thereof.

4. The compound of claim 1, which is (R)-2-[2,6-dibromo-4-(9-bromo-2,3-dimethyl-naphtho[2,3-b]thiophen-4-yl)-phenoxy]-3-phenyl-propionic acid or a pharmaceutically acceptable salt thereof.

5. The compound of claim 1, which is (R)-2-[2-bromo-4-(9-bromo-2,3-dimethyl-naphtho[2,3-b]thiophen-4-yl)-6-ethyl-phenoxy]-3-phenyl-propionic acid or a pharmaceutically acceptable salt thereof.

6. The compound of claim 1, which is (R)-2-[4-(9-bromo-2,3-dimethyl-naphtho[2,3-b]thiophen-4-yl)-2,6-dimethyl-phenoxy]-3-phenyl-propionic acid or a pharmaceutically acceptable salt thereof.

7. The compound of claim 1, which is (R)-2-[4-(9-bromo-2,3-dimethyl-naphtho[2,3-b]thiophen-4-yl)-2-fluoro-phenoxy]-3-phenyl-propionic acid or a pharmaceutically acceptable salt thereof.

8. The compound of claim 1, which is [4-(9-bromo-2,3-dimethyl-naphtho[2,3-b]thiophen-4-yl)-2,6-diisopropyl-phenoxy]-acetic acid or a pharmaceutically acceptable salt thereof.

9. The compound of claim 1, which is (R)-2-[2-bromo-4-(9-bromo-2,3-dimethyl-naphtho[2,3-b]thiophen-4-yl)-6sec-butyl-phenoxy]-3-phenyl-propionic acid or a pharmaceutically acceptable salt thereof.

10. The compound of claim 1, which is (R)-2-[2-bromo-4-(9-bromo-2,3-dimethyl-naphtho[2,3-b]thiophen-4-yl)-6-isopropyl-phenoxy]-3-phenyl-propionic acid or a pharmaceutically acceptable salt thereof.

11. The compound of claim 1, which is (R)-2-[2-bromo-4-(9-bromo-2,3-dimethyl-naphtho[2,3-b]thiophen-4-yl)-2-cyclopentyl-phenoxy]-3-phenyl-propionic acid or a pharmaceutically acceptable salt thereof.

12. The compound of claim 1, which is (R)-2-[4-(9-bromo-2,3-dimethyl-naphtho[2,3-b]thiophen-4-yl)-6-isopropyl-phenoxy]-3-phenyl-propionic acid or a pharmaceutically acceptable salt thereof.

13. The compound of claim 1, which is (R)-2-[4-(9-bromo-2,3-dimethyl-naphtho[2,3-b]thiophen-4-yl)-2-cyclopentyl-phenoxy]-3-phenyl-propionic acid or a pharmaceutically acceptable salt thereof.

14. The compound of claim 1, which is (R)-2-[2,6-dibromo-4-(2,3-dimethyl-9-phenylsulfanyl-naphtho[2,3-b]thiophen-4-yl)-phenoxy]-3-phenyl-propionic acid or a pharmaceutically acceptable salt thereof.

15. The compound of claim 1, which is (R)-2-[2,6-dibromo-4-(9-bromo-2,3-dimethyl-naphtho[2,3-b]thiophen-4-yl)-phenoxy]-4-phenyl-butyric acid or a pharmaceutically acceptable salt thereof.

16. The compound of claim 1, which is (S)-2-[2,6-dibromo-4-(9-bromo-2,3-dimethyl-naphtho[2,3-b]thiophen-4-yl)-phenoxy]-4-phenyl-butyric acid or a pharmaceutically acceptable salt thereof.

17. The compound of claim 1, which is 2-[2,6-dibromo-4-(9-bromo-3-methyl-2-morpholin-4-ylmethyl-naphtho[2,3-b]thiophen-4-yl)-phenoxy]-3-phenyl-propionic acid or a pharmaceutically acceptable salt thereof.

18. The compound of claim 1, which is (R)-2-[2,6-dibromo-4-(2,3-dimethyl-9-phenylsulfanyl-naphtho[2,3-b]thiophen-4-yl)-phenoxy]-propionic acid or a pharmaceutically acceptable salt thereof.

19. The compound of claim 1, which is [2-bromo-4-(9-bromo-2,3-dimethyl-naphtho[2,3-b]thiophen-4-yl)-2-nitrophenoxy]-3-phenyl-propionic acid or a pharmaceutically acceptable salt thereof.

20. The compound of claim 1, which is 2,6-dibromo-4-(9-bromo-2,3-dimethyl-naphtho[2,3-b]thiophen-4yl)-phenol or a pharmaceutically acceptable salt thereof.

21. The compound of claim 1, which is 2-bromo-4-(9-bromo-2,3-dimethyl-naphtho[2,3-b]thiophen-4-yl)-6-nitrophenol or a pharmaceutically acceptable salt thereof.

22. The compound of claim 1, which is (R)-2-[2,6-dibromo-4-(9-bromo-2-diethylaminomethyl-3-methyl-naphtho[2,3-b]thiophen-4-yl)-phenoxy]-3-phenyl-propionic acid or a pharmaceutically acceptable salt thereof.

23. The compound of claim 1, which is (R)-2-[2,6-dibromo-4-(2,3-dimethyl-naphtho[2,3-b]furan-4-yl)-phenoxy]-3-phenyl-propionic acid or a pharmaceutically acceptable salt thereof.

24. The compound of claim 1, which is (2R)-2-[4-9-bromo-2,3-dimethyl-naphtho[2,3-b]thiophen-4-yl)-2,6-diisopropyl-phenoxy]-3-phenyl-propionic acid.

25. The compound of claim 1, which is (R)-2-[4-(9-bromo-2,3-dimethyl-naphtho[2,3-b]thiophen-4-yl)-2,6-diethyl-phenoxy]-3-phenyl-propionic acid.

26. The compound of claim 1, which is {(2R)-2-[4-(9-bromo-2,3-dimethyl-naphtho[2,3-b]thiophen-4-yl)-2,6-dimethyl-phenoxy]-3-phenyl-propionylamino}-acetic acid.

27. The compound of claim 1, which is {(2R)-2-[4-(9-bromo-2,3-dimethyl-naphtho[2,3-b]thiophen-4-yl)-2,6-diethyl-phenoxy]-3-phenyl-propionylamino}-acetic acid.

28. The compound of claim 1, which is (2R)-2-[4-(9-Bromo-2,3-dimethyl-naphtho[2,3-b]thiophen-4-yl)-phenoxy]-3-phenyl-propionic acid or a pharmaceutically acceptable salt thereof.

29. The compound of claim 1, which is (2S)-2-[4-(9-Bromo-2,3-dimethyl-naphtho[2,3-b]thiophen-4-yl)-2,6-dimethyl-phenoxy]-3-phenyl-propionic acid or a pharmaceutically acceptable salt thereof.

30. The compound of claim 1, which is {(2R)-2-[4-(2,3-Dimethyl-naphtho[2,3-b]thiophen-4-yl)-2,6-diethyl-phenoxy]-3-phenyl-propionylamino}-acetic acid or a pharmaceutically acceptable salt thereof.

31. The compound of claim 1, which is (R)-2-[4-(9-Bromo-2,3-dimethyl-naphtho[2,3-b]furan-4-yl)-2,6-diethyl-phenoxy]-3-phenyl-propionic acid or a pharmaceutically acceptable salt thereof.

32. The compound of claim 1, which is (R)-2-[2-Cyclopentyl-4-(2-,3-dimethyl-naphtho[2,3-b]thiophen-4-yl)-phenoxy]-propionic acid or a pharmaceutically acceptable salt thereof.

33. The compound of claim 1, which is (R)-2-[4-(9-Bromo-2,3-dimethyl-naphtho[2,3-b]thiophen-4-yl)-2-cyclopentyl-phenoxy]-propionic acid or a pharmaceutically acceptable salt thereof.

34. The compound of claim 1, which is (R)-2-[4-(2-,3-Dimethyl-naphtho[2,3-b]thiophen-4-yl)-2-ethyl-phenoxy]-3-phenyl-propionic acid or a pharmaceutically acceptable salt thereof.

35. The compound of claim 1, which is 2-Bromo-4-(2,3-dimethyl-naphtho[2,3-b]furan-4-yl)-6-ethyl-phenol or a pharmaceutically acceptable salt thereof.

36. The compound of claim 1, which is (R)-2-[2-Bromo-4-(2,3-dimethyl-naphtho[2,3-b]furan-4-yl)-6-ethyl-phenoxy]-3-phenyl-propionic acid or a pharmaceutically acceptable salt thereof.

37. The compound of claim 1, which is (R)-2-[4-(9-Bromo-2,3-dimethyl-naphtho[2,3-b]thiophen-4-yl)-2-propyl-phenoxy]-3-phenyl-propionic acid or a pharmaceutically acceptable salt thereof.

38. The compound of claim 1, which is (2R)-2-[4-(9-Bromo-2-diethylaminomethyl-3-methyl-naphtho[2,3-b]thiophen-4-yl)-2,6-diisopropyl-phenoxy]-3-phenyl-propionic acid or a pharmaceutically acceptable salt thereof.

39. The compound of claim 1, which is 4-(2,3-dimethyl-naphtho[2,3-b]thiophen-4-yl-phenol; 4-(9-bromo-2,3-dimethyl-naphtho[2,3-b]thiophen-4-yl)-phenol; 4-(2,3-dimethyl-9-phenylsulfanyl-naphtho[2,3-b]thiophen-4-yl)-phenol; 2,6-dibromo-4-(2,3-dimethyl-9-phenylsulfanyl-naphtho[2,3-b]thiophen-4-yl)-phenol; 4-(9-bromo-3-methyl-2-morpholin-4-yl)methyl-naphtho[2,3-b]thiophen-4-yl)-phenol; 4-(9-bromo-2-diethylaminomethyl-3-methyl-naphtho[2,3-b]thiophen-4-yl)-acetate; 4-(9-bromo-2-diethylaminomethyl-3-methyl-naphtho[2,3-b]thiophen-4-yl)-phenol; 2,6-dibromo-4-(9-bromo-2-diethylaminomethyl-3-methyl-naphtho[2,3-b]thiophen-4-yl)-phenol; 2,6-dibromo-4-(9-bromo-3-methyl-2-morpholin-4-ylmethyl-naphtho[2,3-b]thiophen-4-yl)-phenol; 4-(9-bromo-2,3-dimethyl-naphtho[2,3-b]thiophen-4-yl)-2-nitro-phenol; 2-amino-4-(9-bromo-2,3-dimethyl-naphtho[2,3-b]thiophen-4-yl)-phenol; 2-amino-6-bromo-4-(9-bromo-2,3-dimethyl-naphtho[2,3-b]thiophen-4-yl)-phenol; [2-bromo-4-(9-bromo-2,3-dimethyl-naphtho[2,3-b]thiophen-4-yl)-2-nitro-phenoxy]-acetic acid; (R)-2-[2,6-dibromo-4-(9-bromo-2,3-dimethylnaptho[2,3-b]thien-4-yl)-phenoxy]-propanoic acid; 2-[2,6-dibromo-4-(9-bromo-3-methyl-2-morpholin-4-ylmethyl-naphtho[2,3-b]thiophen-4-yl)-phenoxy]-propionic acid; 2-bromo-4-(9-bromo-2,3-dimethyl-naphtho[2,3-b]thiophen-4-yl)-6-isopropyl-phenol; (R)-2-[4-(2,3-dimethyl-naphtho[2,3-b]thiophen-4-yl)-2-isopropyl-phenoxy]-3-phenyl-propionic acid; (R)-2-[2-cyclopentyl-4-(2,3-dimethyl-naphtho[2,3-b]thiophen-4-yl)-phenoxy]-3-phenyl-propionic acid; (R)-2-[4-(2,3-dimethyl-naphtho[2,3-b]thiophen-4-yl)-2,6-dimethyl-phenoxy]-3-phenyl-propionic acid; (R)-2-[4-(2,3-dimethyl-naphtho[2,3-b]thiophen-4-yl)-2,6-diisopropyl-phenoxy]-3-phenyl-propionic acid; (R)-2-[4-(2,3-dimethyl-naphtho[2,3-b]thiophen-4-yl)-2-fluoro-phenoxy]-3-phenyl-propionic acid; (R)-2-[4-(9-bromo-2,3-dimethyl-naphtho[2,3-b]thiophen-4-yl)-2-ethyl-phenoxy]-3-phenyl-propionic acid; 3-bromo-5-(9-bromo-2,3-dimethyl-naphtho[2,3-b]thiophen-4-yl)-2-methoxy-phenylamine; or [3-bromo-5-(9-bromo-2,3-dimethyl-naphtho[2,3-b]thiophen-4-yl)-2-methoxy-phenylamino]-acetic acid; (2R)-2-[4-(9-Bromo-2,3-dimethyl-1-oxo-1H-naphtho[2,3-b]thiophen-4-yl)-2,6-dimethyl-phenoxy]-3-phenyl-propionic acid; (R)-2-[4-(2-,3-Dimethyl-naphtho[2,3-b]thiophen-4-yl)-2,6-diethyl-phenoxy]-3-phenyl-propionic acid; 4-(2,3-Dimethyl-naphtho[2,3-b]furan-4-yl)-2,6-diethyl-phenol; 4-[4-(9-Bromo-2-,3-dimethyl-naphtho[2,3-b]thiophen-4-yl)-2-cyclopentyl-phenoxy]-butyric acid; 2-Cyclopentyl-4-(2-,3-dimethyl-naphtho[2,3-]furan-4-yl)-phenol; Acetic acid 2-cyclopentyl-4-(2-,3-dimethyl-naphtho[2,3-b]furan-4-yl)-phenyl ester; (R)-2-[4-(9-Bromo-2-,3-dimethyl-naphtho[2,3-b]thiophen-4-yl)-2-ethyl-phenoxy]-3-phenyl-propionic acid; 4-[2-Bromo-4-(2,3-dimethyl-naphtho[2,3-b]furan-4-yl)-6-ethyl-phenoxy]-butyric acid; 4-[2-Bromo-4-(2,3-dimethyl-naphtho[2,3-b]furan-4-yl)-6ethyl-phenoxy]-butyramide; 4-(2,3-Dimethyl-naphtho[2,3-b]furan-4-yl)-2-ethyl-phenol; [9-Bromo-4-(4-methoxy-3,5-dimethylphenyl)-3-methylnaphtho[2,3-b]thien-2-yl]methyl acetate; 4-(9-Bromo-2-,3-dimethyl-naphtho[2,3-b]thien-4-yl)-2-methyl-phenyl acetate; Acetic acid 4-(9-bromo-2-diethylaminomethyl-3-methyl-naphtho[2,3-b]thiophen-4-yl)-2,6-dimethyl-phenyl ester; 2-[4-(9-Bromo-2-diethylaminomethyl-3-methyl-naphtho[2,3-b]thiophen-4-yl)-2,6-dimethyl-phenoxy]-3-phenyl-propionic acid; or a pharmaceutically acceptable salt thereof.

40. The compound of claim 1, which is acetic acid 4-(2,3-dimethyl-naphtho[2,3-b]thiophen-4-yl)-phenyl ester; acetic acid 4-(9-bromo-2,3-dimethyl-naphtho[2,3-b]thiophen-4-yl)-phenyl ester; methanesulfonic acid 4-(2,3-dimethyl-naphtho[2,3-b]thiophen-4-yl)-phenyl ester; methanesulfonic acid 4-(9-iodo-2,3-dimethyl-naphtho[2,3-b]thiophen-4-yl)-phenyl ester; acetic acid 4-(9-bromo-2-chloromethyl-3-methyl-naphtho[2,3-b]thiophen-4-yl)-phenyl ester; (R)-2-[2,6-dibromo-4-(9-bromo-2,3-dimethyl-naphtho[2,3-b]thiophen-4-yl)-phenoxy]-3-phenyl-propionic acid methyl ester; [3-bromo-5-(9-bromo-2,3-dimethyl-naphtho[2,3-b]thiophen-4-yl)-2-hydroxy-phenyl]-carbamic acid tert-butyl ester; 9-bromo-4-(3-bromo-methoxy-5-nitro-phenyl)-2,3-dimethyl-naphtho[2,3-b]thiophene; or [3-bromo-5-(9-bromo-2,3-dimethyl-naphtho[2,3-b]thiophen-4-yl)-2-methoxy-phenylamino]-acetic acid methyl ester.

41. A method of treating metabolic disorders mediated by insulin resistance or hyperglycemia in a mammal in need thereof which comprises administering to said mammal, a compound of formula I having the structure

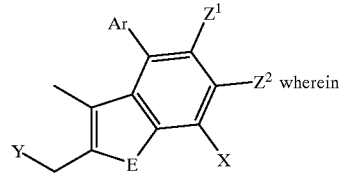

(I)

Ar is

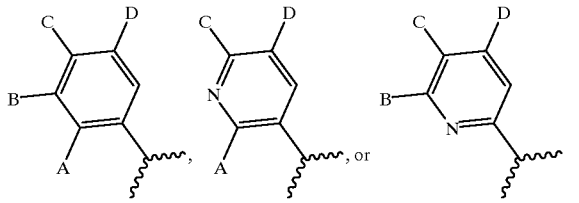

A is hydrogen, halogen, or OH;
B and D are each, independently, hydrogen, halogen, CN, alkyl of 1–6 carbon atoms, aryl, aralkyl of 6–12 carbon atoms, hydroxyalkyl of 1–6 carbon atoms, hydroxyalkyl of 6–12 carbon atoms, cycloalkyl of 3–8 carbon atoms, nitro, amino, —$NR^1R^{1a}$, —$NR^1COR^{1a}$, —$NR^1CO_2R^{1a}$, cycloalkylamino of 3–8 carbon atoms, morpholino, furan-2-yl, furan-3-yl, thiophen-2-yl, thiophen-3-yl, —$COR^{1b}$ or OR;
R is hydrogen, alkyl of 1–6 carbon atoms, —$COR^1$, —$(CH_2)_nCO_2R^1$, —$CH(R^{1a})CO_2R^1$, —$SO_2R^1$, —$(CH_2)_mCH(OH)CO_2R^1$, —$(CH_2)_mCOCO_2R^1$, —$(CH_2)_mCH=CHCO_2R^1$, or —$(CH_2)_mO(CH_2)_oCO_2R^1$;
$R^1$ is hydrogen, alkyl of 1–6 carbon atoms, aralkyl of 6–12 carbon atoms, aryl, or $CH_2CO_2R^1$;
$R^{1'}$ is hydrogen or alkyl of 1–6 carbon atoms
E is S, SO, $SO_2$, O, or $NR^{1c}$;
X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyalkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, —$OCH_2CO_2R^{2b}$ or —$COR^{2c}$;
Y is hydrogen, halogen, alkyl of 1–6 carbon atoms, aryl, aralkyl of 6–12 carbon atoms, hydroxyalkyl of 1–6 carbon atoms, hydroxyalkyl of 6–12 carbon atoms, —$OR^3$, $SR^3$, $NR^3R^{3a}$, —$COR^{3b}$, morpholine or piperidine;
$R^{1a}$, $R^{1c}$, $R^2$, $R^{2a}$, $R^3$, $R^{3a}$ are each, independently, hydrogen, alkyl of 1–6 carbon atoms, aralkyl of 6–12 carbon atoms, or aryl;
$R^{1b}$ is alkyl of 1–6 carbon atoms or aryl;
$R^{2b}$ is hydrogen, alkyl of 1–6 carbon atoms;
$R^{2c}$ and $R^{3b}$ are each, independently, alkyl of 1–6 carbon atoms, aryl, or aralkyl of 6–12 carbon atoms;
C is hydrogen, halogen or $OR^4$;
$R^4$ is hydrogen, alkyl of 1–6 carbon atoms, —$CH(R_5)W$, —$C(CH_3)_2CO_2R^6$, 5-thiazolidine-2,4-dione, —CH($R^7$)$(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_pCH=CHCO_2R^6$, or —$(CH_2)_pO(CH_2)_qCO_2R^6$;
$R^5$ is hydrogen, alkyl of 1–6 carbon atoms, aralkyl of 6–12 carbon atoms, aryl, —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), —$CH_2$(3-pyridyl), —$CH_2CO_2H$, or —$(CH_2)_nG$;
G is $NR^{6a}R^{7a}$, $NR^{6a}COR^{7a}$,

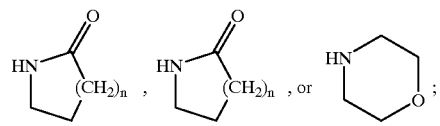

W is $CO_2R^6$, $CONH_2$, CONHOH, CN, $CONH(CH_2)_2CN$, 5-tetrazole, —$PO_3(R^6)_2$, —$CH_2OH$, —$CONR^{6b}CHR^{7b}$, —$CH_2NR^{6b}CHR^{7b}CO_2R^6$, —$CH_2OCHR^{7b}CO_2R^6$ or —$CH_2Br$, —$CONR^{6b}CHR^{7b}CO_2R^6$;
$R^6$, $R^{6a}$, $R^7$, $R^{7a}$ are each, independently, is hydrogen, alkyl of 1–6 carbon atoms, or aryl;
$R^{6b}$ is hydrogen or $COR^{6c}$;
$R^{6c}$ is alkyl of 1–6 carbon atoms or aryl;
$R^{7b}$ is hydrogen, alkyl of 1–6 carbon atoms, or hydroxyalkyl of 1–6 carbon atoms;
$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —CH=$CR^9$—$CR^{10}$=$CR^{11}$—;
$R^8$ is hydrogen, alkyl of 1–6 carbon atoms, or aryl;
$R^9$, $R^{10}$, and $R^{11}$ are each, independently, hydrogen, alkyl of 1–6 carbon atoms, aryl, halogen, hydroxy, or alkoxy of 1–6 carbon atoms
m is 1 to 4
n is 1 or 2;
p is 1 to 4;
q is 1 to 4;
or a pharmaceutically acceptable salt thereof.

42. A method of treating or inhibiting type II diabetes in a mammal in need thereof which comprises administering to said mammal, a compound of formula I having the structure

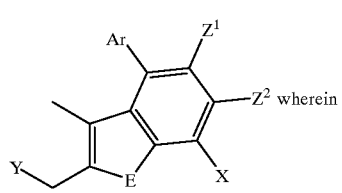

(I)

-continued

Ar is

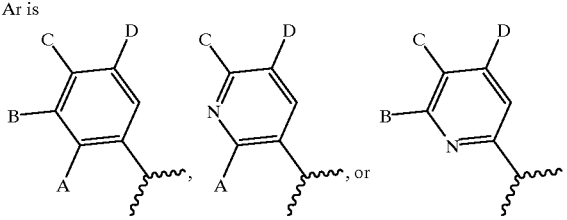

A is hydrogen, halogen, or OH;

B and D are each, independently, hydrogen, halogen, CN, alkyl of 1–6 carbon atoms, aryl, aralkyl of 6–12 carbon atoms, hydroxyalkyl of 1–6 carbon atoms, hydroxyalkyl of 6–12 carbon atoms, cycloalkyl of 3–8 carbon atoms, nitro, amino, —$NR^1R^{1a}$, —$NR^1COR^{1a}$, —$NR^1CO_2R^{1a}$, cycloalkylamino of 3–8 carbon atoms, morpholino, furan-2-yl, furan-3-yl, thiophen-2-yl, thiophen-3-yl, —$COR^{1b}$ or OR;

R is hydrogen, alkyl of 1–6 carbon atoms, —$COR^1$, —$(CH_2)_nCO_2R^1$, —$CH(R^{1a})CO_2R^1$, —$SO_2R^1$, —$(CH_2)_mCH(OH)CO_2R^1$, —$(CH_2)_mCOCO_2R^1$, —$(CH)_mCH=CHCO_2R^1$, or —$(CH_2)_mO(CH_2)_oCO_2R^1$;

$R^1$ is hydrogen, alkyl of 1–6 carbon atoms, aralkyl of 6–12 carbon atoms, aryl, or $CH_2CO_2R^{1'}$;

$R^{1'}$ is hydrogen or alkyl of 1–6 carbon atoms

E is S, SO, $SO_2$, O, or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyalkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, —$OCH_2CO_2R^{2b}$ or —$COR^{2c}$;

Y is hydrogen, halogen, alkyl of 1–6 carbon atoms, aryl, aralkyl of 6–12 carbon atoms, hydroxyalkyl of 1–6 carbon atoms, hydroxyalkyl of 6–12 carbon atoms, —$OR^3$, $SR^3$, $NR^3R^{3a}$, —$COR^{3b}$, morpholine or piperidine;

$R^{1a}$, $R^{1c}$, $R^2$, $R^{2a}$ $R^3$, $R^{3a}$ are each, independently, hydrogen, alkyl of 1–6 carbon atoms, aralkyl of 6–12 carbon atoms, or aryl;

$R^{1b}$ is alkyl of 1–6 carbon atoms or aryl;

$R^{2b}$ is hydrogen, alkyl of 1–6 carbon atoms;

$R^{2c}$ and $R^{3b}$ are each, independently, alkyl of 1–6 carbon atoms, aryl, or aralkyl of 6–12 carbon atoms;

C is hydrogen, halogen or $OR^4$;

$R^4$ is hydrogen, alkyl of 1–6 carbon atoms, —$CH(R_5)W$, —$C(CH_3)_2CO_2R^6$, 5-thiazolidine-2,4-dione, —$CH(R^7)(CH_2)_mCO_2R^6$, —$COR^6$, —$PO_3(R^6)_2$, —$SO_2R^6$, —$(CH_2)_pCH(OH)CO_2R^6$, —$(CH_2)_pCOCO_2R^6$, —$(CH_2)_pCH=CHCO_2R^6$, or —$(CH_2)_pO(CH_2)_qCO_2R^6$;

$R^5$ is hydrogen, alkyl of 1–6 carbon atoms, aralkyl of 6–12 carbon atoms, aryl, —$CH_2(1H\text{-imidazol-4-yl})$, —$CH_2(3\text{-}1H\text{-indolyl})$, —$CH_2CH_2(1,3\text{-dioxo-1,3-dihydro-isoindol-2-yl})$, —$CH_2CH_2(1\text{-oxo-1,3-dihydro-isoindol-2-yl})$, —$CH_2(3\text{-pyridyl})$, —$CH_2CO_2H$, or —$(CH_2)_nG$;

G is $NR^{6a}R^{7a}$, $NR^{6a}COR^{7a}$,

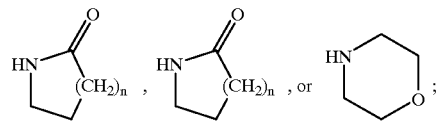

W is $CO_2R^6$, $CONH_2$, CONHOH, CN, $CONH(CH_2)_2CN$, 5-tetrazole, —$PO_3(R^6)_2$, —$CH_2OH$, —$CONR^{6b}CHR^{7b}$, —$CH_2NR^{6b}CHR^{7b}CO_2R^6$, —$CH_2OCHR^{7b}CO_2R^6$ —$CH_2Br$, or —$CONR^{6b}CHR^{7b}CO_2R^6$;

$R^6$, $R^{6a}$, $R^7$, $R^{7a}$ are each, independently, is hydrogen, alkyl of 1–6 carbon atoms, or aryl;

$R^{6b}$ is hydrogen or —$COR^{6c}$;

$R^{6c}$ is alkyl of 1–6 carbon atoms or aryl;

$R^{7b}$ is hydrogen, alkyl of 1–6 carbon atoms, or hydroxyalkyl of 1–6 carbon atoms;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —$NR^1R^{1a}$, —$NR^1COR^{1a}$, cycloalkylamino of 3–8 carbon atoms, morpholino, or $OR^8$, or $Z^1$ and $Z^2$ may be taken together as a diene unit having the formula —$CH=CR^9$—$CR^{10}=CR^{11}$—;

$R^8$ is hydrogen, alkyl of 1–6 carbon atoms, or aryl;

$R^9$, $R^{10}$, and $R^{11}$ are each, independently, hydrogen, alkyl of 1–6 carbon atoms, aryl, halogen, hydroxy, or alkoxy of 1–6 carbon atoms m is 1 to 4 n is 1 or 2;

p is 1 to 4;

q is 1 to 4;

or a pharmaceutically acceptable salt thereof.

43. A method of modulating glucose levels in a mammal in need thereof which comprises administering to said mammal, a compound of formula I having the structure

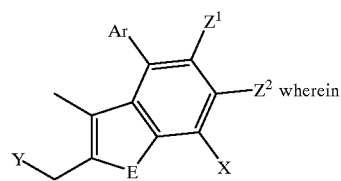
(I)

wherein

Ar is

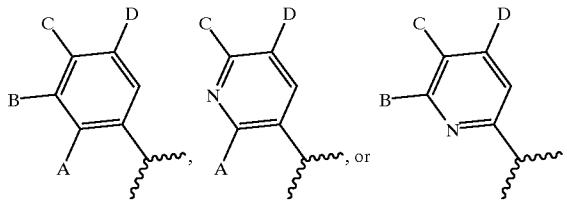

A is hydrogen, halogen, or OH;

B and D are each, independently, hydrogen, halogen, CN, alkyl of 1–6 carbon atoms, aryl, aralkyl of 6–12 carbon atoms, hydroxyalkyl of 1–6 carbon atoms, hydroxyalkyl of 6–12 carbon atoms, cycloalkyl of 3–8 carbon atoms, nitro, amino, $-NR^1R^{1a}$, $-NR^1COR^{1a}$, $-NR^1CO_2R^{1a}$, cycloalkylamino of 3–8 carbon atoms, morpholino, furan-2-yl, furan-3-yl, thiophen-2-yl, thiophen-3-yl, $-COR^{1b}$ or OR;

R is hydrogen, alkyl of 1–6 carbon atoms, $-COR^1$, $-(CH_2)_nCO_2R^1$, $-CH(R^{1a})CO_2R^1$, $-SO_2R^1$, $-(CH_2)_mCH(OH)CO_2R^1$, $-(CH_2)_mCOCO_2R^1$, $-(CH_2)_mCH=CHCO_2R^1$, or $-(CH_2)_mO(CH_2)_oC_2R^1$;

$R^1$ is hydrogen, alkyl of 1–6 carbon atoms, aralkyl of 6–12 carbon atoms, aryl, or $CH_2CO_2R^{1'}$;

$R^{1'}$ is hydrogen or alkyl of 1–6 carbon atoms

E is S, SO, $SO_2$, O, or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyalkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, $-OCH_2CO_2R^{2b}$ or $-COR^{2c}$;

Y is hydrogen, halogen, alkyl of 1–6 carbon atoms, aryl, aralkyl of 6–12 carbon atoms, hydroxyalkyl of 1–6 carbon atoms, hydroxyalkyl of 6–12 carbon atoms, $-OR^3$, $SR^3$, $NR^3R^{3a}$, $-COR^{3b}$, morpholine or piperidine;

$R^{1a}$, $R^{1c}$, $R^2$, $R^{2a}$ $R^3$, $R^{3a}$ are each, independently, hydrogen, alkyl of 1–6 carbon atoms, aralkyl of 6–12 carbon atoms, or aryl;

$R^{1b}$ is alkyl of 1–6 carbon atoms or aryl;

$R^{2b}$ is hydrogen, alkyl of 1–6 carbon atoms;

$R^{2c}$ and $R^{3b}$ are each, independently, alkyl of 1–6 carbon atoms, aryl, or aralkyl of 6–12 carbon atoms;

C is hydrogen, halogen or $OR^4$;

$R^4$ is hydrogen, alkyl of 1–6 carbon atoms, $-CH(R_5)W$, $-C(CH_3)_2CO_2R^6$, 5-thiazolidine-2,4-dione, $-CH(R^7)(CH_2)_mCO_2R^6$, $-COR^6$, $-PO_3(R^6)_2$, $-SO_2R^6$, $-(CH_2)_pCH(OH)CO_2R^6$, $-(CH_2)_pCOCO_2R^6$, $-(CH_2)_pCH=CHCO_2R^6$, or $-(CH2)_pO(CH_2)_qCO_2R^6$;

$R^5$ is hydrogen, alkyl of 1–6 carbon atoms, aralkyl of 6–12 carbon atoms, aryl, $-CH_2(1H-imidazol-4-yl)$, $-CH_2(3-1H-indolyl)$, $-CH_2CH_2(1,3-dioxo-1,3-dihydro-isoindol-2-yl)$, $-CH_2CH_2(1-oxo-1,3-dihydro-isoindol-2-yl)$, $-CH_2(3-pyridyl)$, $-CH_2CO_2H$, or $-(CH_2)_nG$;

G is $NR^{6a}R^{7a}$, $NR^{6a}COR^{7a}$,

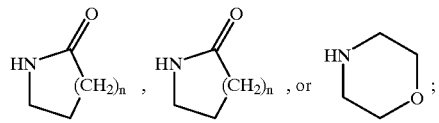

W is $CO_2R^6$, $CONH_2$, $CONHOH$, CN, $CONH(CH_2)_2CN$, 5-tetrazole, $-PO_3(R^6)_2$, $-CH_2H$, $-CONR^{6b}CHR^{7b}$, $-CH_2NR^{6b}CHR^{7b}CO_2R^6$, $-CH_2OCHR^{7b}CO_2R^6$ $-CH_2Br$, or $-CONR^{6b}CHR^{7b}CO_2R^6$;

$R^6$, $R^{6a}$, $R^7$, $R^{7a}$ are each, independently, is hydrogen, alkyl of 1–6 carbon atoms, or aryl;

$R^{6b}$ is hydrogen or $-COR^{6c}$;

$R^{6c}$ is alkyl of 1–6 carbon atoms or aryl;

$R^{7b}$ is hydrogen, alkyl of 1–6 carbon atoms, or hydroxyalkyl of 1–6 carbon atoms;

$Z^1$ and $Z^2$ are each, independently, hydrogen, halogen, CN, alkyl of 1–6 carbon atoms, aryl, aralkyl of 6–12 carbon atoms, cycloalkyl of 3–8 carbon atoms, nitro, amino, $-NR^1R^{1a}$, $-NR^1COR^{1a}$, cycloalkylamino of 3–8 carbon atoms, morpholino, or $OR^8$, or $Z^1$ and $Z^2$ may be taken together as a diene unit having the formula $-CH=CR^9-CR^{10}=CR^{11}$;

$R^8$ is hydrogen, alkyl of 1–6 carbon atoms, or aryl;

$R^9$, $R^{10}$, and $R^1$ are each, independently, hydrogen, alkyl of 1–6 carbon atoms, aryl, halogen, hydroxy, or alkoxy of 1–6 carbon atoms m is 1 to 4 n is 1 or 2;

p is 1 to 4;

q is 1 to 4;

or a pharmaceutically acceptable salt thereof.

44. A pharmaceutical composition which comprises a compound of formula I having the structure

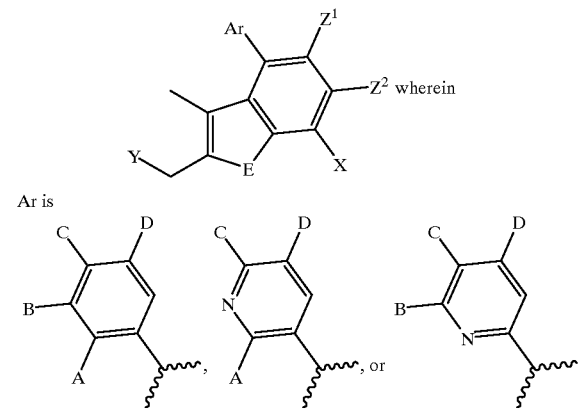

A is hydrogen, halogen, or OH;

B and D are each, independently, hydrogen, halogen, CN, alkyl of 1–6 carbon atoms, aryl, aralkyl of 6–12 carbon atoms, hydroxyalkyl of 1–6 carbon atoms, hydroxyalkyl of 6–12 carbon atoms, cycloalkyl of 3–8 carbon atoms, nitro, amino, $-NR^1R^{1a}$, $-NR^1COR^{1a}$, $-NR^1CO_2R^{1a}$, cycloalkylamino of 3–8 carbon atoms, morpholino, furan-2-yl, furan-3-yl, thiophen-2-yl, thiophen-3-yl, $-COR^{1b}$ or OR;

R is hydrogen, alkyl of 1–6 carbon atoms, $-COR^1$, $-(CH_2)_nCO_2R^1$, $-CH(R^{1a})CO_2R^1$, $-S_2R^1$, $-(CH_2)_mCH(OH)CO_2R^1$, $-(CH_2)_mCOCO_2R^1$, $-(CH_2)_mCH=CHCO_2R^1$, or $-(CH_2)_mO(CH_2)_oCO_2R^1$;

$R^1$ is hydrogen, alkyl of 1–6 carbon atoms, aralkyl of 6–12 carbon atoms, aryl, or $CH_2CO_2R^{1'}$;

$R^{1'}$ is hydrogen or alkyl of 1–6 carbon atoms

E is S, SO, $SO_2$, O or $NR^{1c}$;

X is hydrogen, halogen, alkyl of 1–6 carbon atoms, alkenyl of 2–7 carbon atoms, CN, aryl, aralkyl of 6–12 carbon atoms, hydroxyalkyl of 1–6 carbon atoms, hydroxyalkyl of 6–12 carbon atoms, perfluoroalkyl of 1–6 carbon atoms, alkoxy of 1–6 carbon atoms, aryloxy; arylalkoxy, nitro, amino, $NR^2R^{2a}$, $NR^2COR^{2a}$, cycloalkylamino of 3–8 carbon atoms, morpholino, alkylsulfanyl of 1–6 carbon atoms, arylsulfanyl, pyridylsulfanyl, 2-N,N-dimethylaminoethylsulfanyl, —OCH$_2$CO$_2$R$^{2b}$ or —COR$^{2c}$;

Y is hydrogen, halogen, alkyl of 1–6 carbon atoms, aryl, aralkyl of 6–12 carbon atoms, hydroxyalkyl of 1–6 carbon atoms, hydroxyalkyl of 6–12 carbon atoms, —OR$^3$, SR$^3$, NR$^3$R$^{3a}$, —COR$^{3b}$, morpholine or piperidine;

R$^{1a}$, R$^{1c}$, R$^2$, R$^{2a}$R$^3$, R$^{3a}$ are each, independently, hydrogen, alkyl of 1–6 carbon atoms, aralkyl of 6–12 carbon atoms, or aryl;

R$^{1b}$ is alkyl of 1–6 carbon atoms or aryl;

R$^{2b}$ is hydrogen, alkyl of 1–6 carbon atoms;

R$^{2c}$ and R$^{3b}$ are each, independently, alkyl of 1–6 carbon atoms, aryl, or aralkyl of 6–12 carbon atoms;

C is hydrogen, halogen or OR$^4$;

R$^4$ is hydrogen, alkyl of 1–6 carbon atoms, —CH(R$_5$)W, —C(CH$_3$)$_2$CO$_2$R$^6$, 5-thiazolidine-2,4-dione, —CH(R$^7$)(CH$_2$)$_m$CO$_2$R$^6$, —COR$^6$, —PO$_3$(R$^6$)$_2$, —SO$_2$R$^6$, —(CH$_2$)$_p$CH(OH)CO$_2$R$^6$, —(CH$_2$)$_p$COCO$_2$R$^6$, —(CH$_2$)$_p$CH=CHCO$_2$R$^6$, or —(CH2)$_p$O(CH$_2$)$_q$CO$_2$R$^6$;

R$^5$ is hydrogen, alkyl of 1–6 carbon atoms, aralkyl of 6–12 carbon atoms, aryl, —CH$_2$(1H-imidazol-4-yl), —CH$_2$(3-1H-indolyl), —CH$_2$CH$_2$(1,3-dioxo-1,3-dihydro-isoindol-2-yl), —CH$_2$CH$_2$(1-oxo-,1,3-dihydro-isoindol-2-yl), —CH$_2$(3-pyridyl), —CH$_2$CO$_2$H, or —(CH$_2$)$_n$G;

G is NR$^{6a}$R$^{7a}$, NR$^{6a}$COR$^{7a}$,

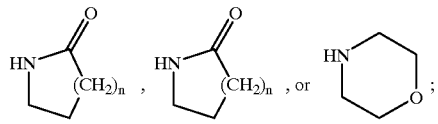

W is CO$_2$R$^6$, CONH$_2$, CONHOH, CN, CONH(CH$_2$)$_2$CN, 5-tetrazole, —PO$_3$(R$^6$)$_2$, —CH$_2$OH, —CONR$^{6b}$CHR$^{7b}$, —CH$_2$NR$^{6b}$CHR$^{7b}$CO$_2$R$^6$, —CH$_2$OCHR$^{7b}$CO$_2$R$^6$ —CH$_2$Br, or —CONR$^{6b}$CHR$^{7b}$CO$_2$R$^6$;

R$^6$, R$^{6a}$, R$^7$, R$^{7a}$ are each, independently, is hydrogen, alkyl of 1–6 carbon atoms, or aryl;

R$^{6b}$ is hydrogen or —COR$^{6c}$;

R$^{6c}$ is alkyl of 1–6 carbon atoms or aryl;

R$^{7b}$ is hydrogen, alkyl of 1–6 carbon atoms, or hydroxyalkyl of 1–6 carbon atoms;

Z$^1$ and Z$^2$ are each, independently, hydrogen, halogen, CN, alkyl of 1–6 carbon atoms, aryl, aralkyl of 6–12 carbon atoms, cycloalkyl of 3–8 carbon atoms, nitro, amino, —NR$^1$R$^{1a}$, —NR$^1$COR$^{1a}$, cycloalkylamino of 3–8 carbon atoms, morpholino, or OR$^8$, or Z$^1$ and Z$^2$ may be taken together as a diene unit having the formula —CH=CR$^9$—CR$^{10}$=CR$^{11}$;

R$^8$ is hydrogen, alkyl of 1–6 carbon atoms, or aryl;

R$^9$, R$^{10}$, and R$^{11}$ are each, independently, hydrogen, alkyl of 1–6 carbon atoms, aryl, halogen, hydroxy, or alkoxy of 1–6 carbon atoms m is to 4 n is 1 or 2;

p is 1 to 4;

q is to 4;

or a pharmaceutically acceptable salt thereof.

* * * * *